US010527631B2

(12) United States Patent
Antebi et al.

(10) Patent No.: US 10,527,631 B2
(45) Date of Patent: Jan. 7, 2020

(54) COMPOSITIONS AND METHODS FOR PROGRAMMABLE SENSING AND CONTROL THROUGH COMBINATORIAL MOLECULAR INTERACTIONS

(71) Applicant: CALIFORNIA INSTITUTE OF TECHNOLOGY, Pasadena, CA (US)

(72) Inventors: Yaron E. Antebi, Pasadena, CA (US); James Linton, Pasadena, CA (US); Michael Elowitz, Los Angeles, CA (US); Heidi Klumpe, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 15/847,909

(22) Filed: Dec. 19, 2017

(65) Prior Publication Data

US 2018/0172704 A1 Jun. 21, 2018

Related U.S. Application Data

(60) Provisional application No. 62/436,071, filed on Dec. 19, 2016.

(51) Int. Cl.
*G01N 33/68* (2006.01)
*G01N 33/569* (2006.01)
*C07K 14/71* (2006.01)
*G01N 33/566* (2006.01)

(52) U.S. Cl.
CPC ......... *G01N 33/6872* (2013.01); *C07K 14/71* (2013.01); *G01N 33/566* (2013.01); *G01N 33/56966* (2013.01); *A01K 2227/105* (2013.01); *G01N 2500/10* (2013.01)

(58) Field of Classification Search
CPC ............. G01N 33/6872; G01N 33/566; G01N 33/56966; G01N 2333/71; G01N 2333/51; G01N 2500/10
See application file for complete search history.

(56) References Cited

U.S. PATENT DOCUMENTS

| | | | | |
|---|---|---|---|---|
| 2011/0097799 A1* | 4/2011 | Stankewicz | .......... | C12N 5/0657 435/377 |
| 2011/0135710 A1* | 6/2011 | Sheikhnehjad | ........ | A61K 31/70 424/450 |
| 2014/0234964 A1* | 8/2014 | West | .................... | C12N 5/0655 435/377 |
| 2018/0153940 A1* | 6/2018 | Bloemen | .............. | C12N 5/0654 |

OTHER PUBLICATIONS

Thomson et al., Science. 1998;282:1145-1147 (Year: 1998).*
Herrera et al., BMC Cell Biol. Mar. 19, 2009;10:20 (Year: 2009).*
Daly, A.C. et al., Transforming Growth Factor Beta-Induced smad 1/5 Phosphorylation in Epithelial Cells in Medicated by Novel Receptor Comiexes and is Essential for Anchorage-Independent Growth, Molecular and Cellular Biology, Nov. 2008, vol. 28, No. 22, pp. 6889-6902.
Dyer, L.A. et al., The Role of BMPs in Endothelial Cell Function and Dysfunction, Trends Endocrinol Metab., Sep. 2014, vol. 25, No. 9, pp. 472-480.
Li, J., Bone Morphogenetic Proteins and Their Co-Receptor, Repulsive Guidance Molecules, Signaling Pathways in Human Cancers, Thesis submitted to Cardiff University for the degree of Doctor of Philosophy, Metastasis & Angiogenesis Research Group Cardiff University School of Medicine, Nov. 2010, 84 pages.
International Search Report and Written Opinion issued in corresponding International Application No. PCT/US2017/067446, dated May 4, 2018, 14 pages.

* cited by examiner

*Primary Examiner* — Daniel C Gamett
(74) *Attorney, Agent, or Firm* — Sheppard, Mullin, Richter & Hampton LLP

(57) ABSTRACT

Methods and compositions are provided for the selective activation of a BMP-dependent response in certain cell types. Methods include identifying a ligand or ligand combinations as well as cell receptor profiles that result in selectively activating a ligand-dependent response through interactions with ligand receptors on a first cell type that do not activate the ligand-dependent response in a second cell type.

9 Claims, 58 Drawing Sheets
(53 of 58 Drawing Sheet(s) Filed in Color)

3 out of 20 dimensions shown

Same receptor configuration
Different environments

Different receptor configuration
Same environment

Ligand Integration Modes

FIG. 4C
FIG. 4D
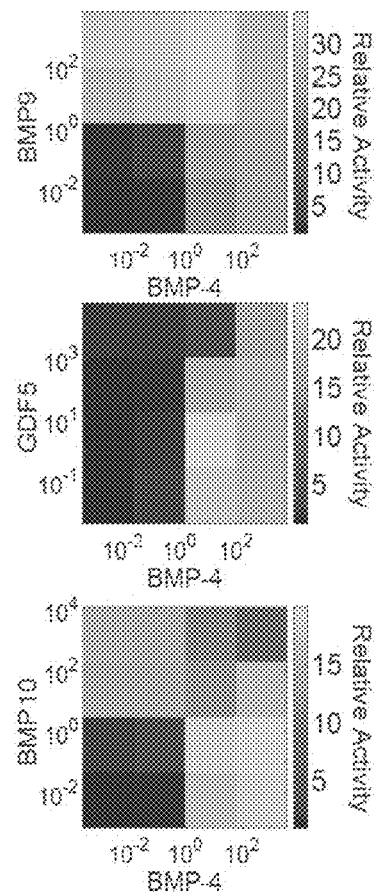
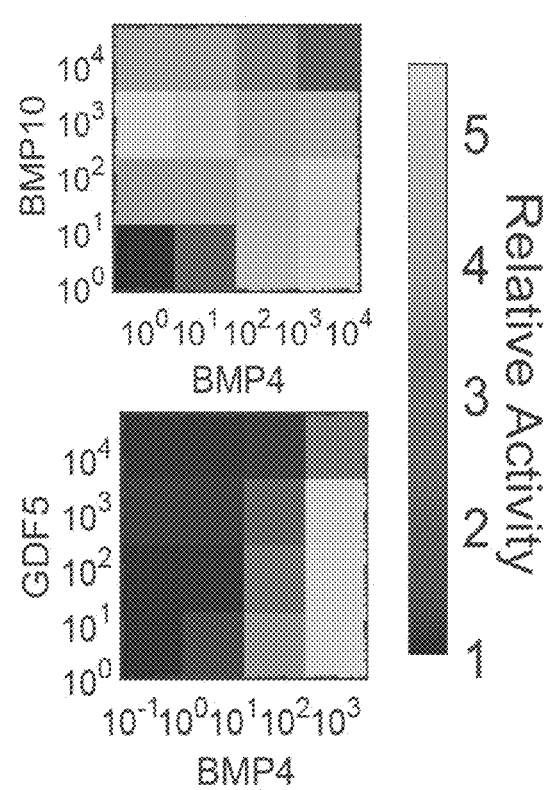

$$A_i + L_j \rightarrow D_{ij} \qquad D_{ij} = K_{ij}^D A_i L_j$$
$$D_{ij} + B_k \rightarrow T_{ijk} \qquad T_{ijk} = K_{ijk}^T D_{ij} B_k$$
$$S = \sum_{ijk} \varepsilon_{ijk} T_{ijk}$$

Affinities and receptor expression levels

Imbalance Detection

Balance Detection

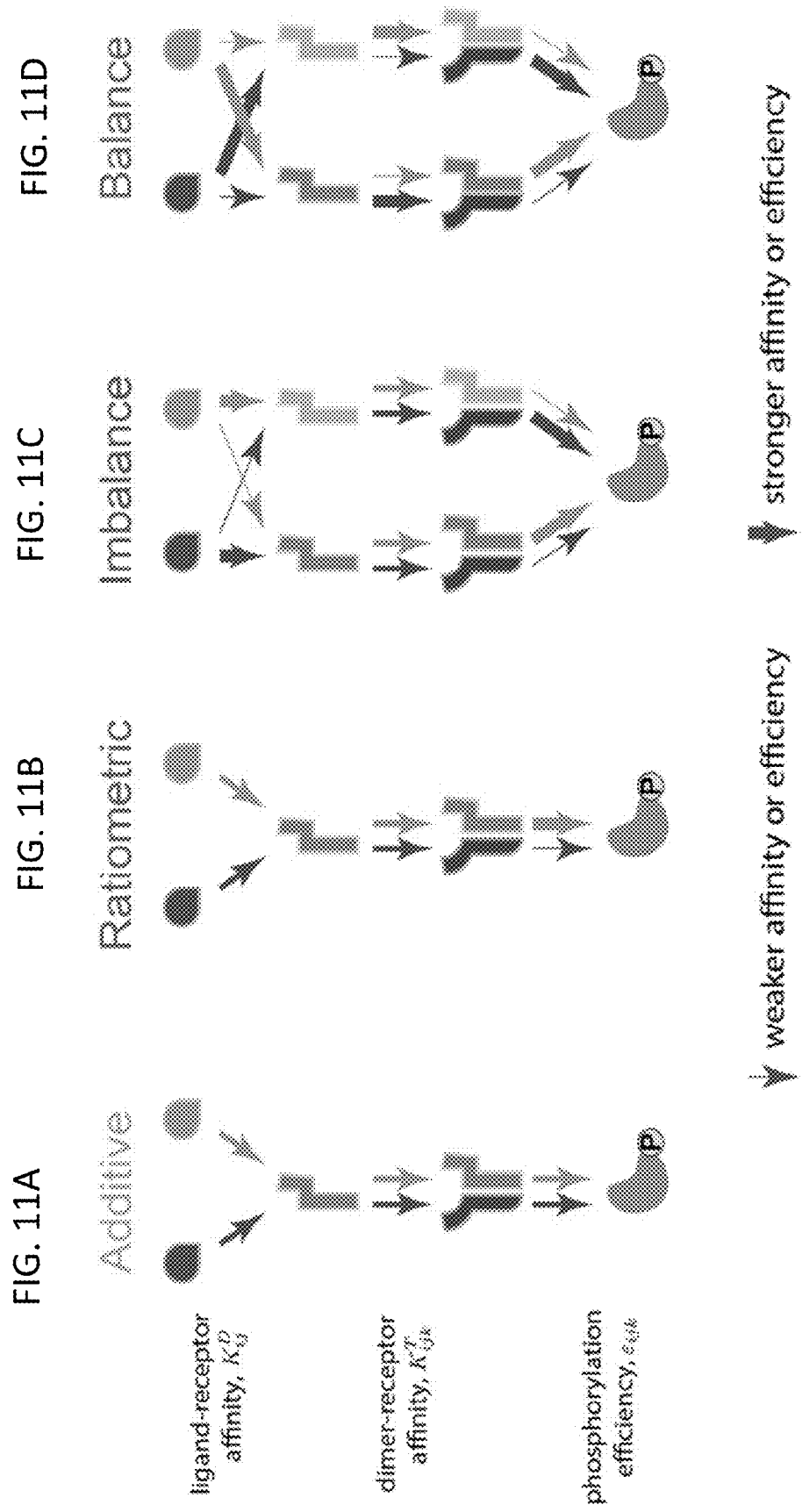

Pathway activation (simulation data)

Ligand 1 + Ligand 2

Pathway activation (simulation data)

Ligand 1 + Ligand 2

$$RLS = \frac{L_{weak}}{L_{strong}}$$

$$LIC = \frac{min}{L_{weak}} - \frac{L_{strong}}{max}$$

COMPOSITIONS AND METHODS FOR PROGRAMMABLE SENSING AND CONTROL THROUGH COMBINATORIAL MOLECULAR INTERACTIONS

CROSS-REFERENCE TO RELATED APPLICATION(S)

The present application claims priority to and the benefit of U.S. Provisional Application Ser. No. 62/436,071 filed on Dec. 19, 2016, the entire content of which is incorporated herein by reference.

STATEMENT REGARDING FEDERALLY SPONSORED RESEARCH OR DEVELOPMENT

This invention was made with government support under Grant No. GM079771 awarded by the National Institutes of Health and Grant No. EFRI1137269 awarded by the National Science Foundation. The government has certain rights in the invention.

BACKGROUND

Signaling pathways play central roles in nearly every tissue context and in many diseases, including cancer, making them major targets for drug development. Rational drug design approaches can successfully target specific pathway components, but still lack necessary cell type or cell context specificity, and therefore can lead to unwanted side effects.

For many of the intercellular signaling pathways such as Bone Morphogenetic Protein (BMP), Wnt, Notch, and JAK-STAT, rather than using a single ligand and receptor, these systems comprise multiple ligand and receptor variants that interact promiscuously with one another to combinatorially generate a large set of distinct signaling complexes. These complexes activate the same intracellular targets, and therefore appear to operate redundantly. The use of redundant ligands and receptors has been thought to offer regulatory flexibility or provide robustness to genetic variation. However, redundancy does not appear to provide a complete understanding of these pathways. Methods to more specifically manipulate signaling pathways are desirable in many applications, including cell-based therapeutics and directed cell differentiation.

SUMMARY

In some embodiments of the present disclosure, a method of inducing a bone morphogenetic protein (BMP)-dependent response in a cell includes a mouse mammary gland (NMuMG)-like BMP receptor profile, an embryonic stem cell (ESC)-like BMP receptor profile, an overexpressed BMPR1B NMuMG-like BMP receptor profile, or an overexpressed ALK1 NMuMG-like BMP receptor profile, wherein the method includes exposing the cells having the NMuMG-like BMP receptor profile to heterologous BMPs selected from BMP4, BMP9, BMP10, or a mixture of BMP4 and BMP9; exposing the cells comprising the ESC-like BMP receptor profile to heterologous BMPs selected from a mixture of BMP4 and BMP9; exposing the cells having the overexpressed BMPR1B NMuMG-like BMP receptor profile to heterologous BMPs selected from BMP4, BMP9, BMP10, GDF5, a mixture of BMP4 and BMP9, or a mixture of BMP4 and GDF5; or exposing the cells having the overexpressed ALK1 NMuMG-like BMP receptor profile to heterologous BMPs selected from BMP4, BMP9, BMP10, a mixture of BMP4 and BMP9, or a mixture of BMP4 and BMP10.

In some embodiments of the present disclosure, a composition for inducing a bone morphogenetic protein (BMP)-dependent response in a cell includes a mouse mammary gland (NMuMG)-like BMP receptor profile, an embryonic stem cell (ESC)-like BMP receptor profile, an overexpressed BMPR1B NMuMG-like BMP receptor profile, or an overexpressed ALK1 NMuMG-like BMP receptor profile, the composition including: a mixture of heterologous BMP4 homodimers and heterologous BMP9 homodimers for inducing the BMP-dependent response in the cell comprising the NMuMG-like BMP receptor profile or the ESC-like BMP receptor profile; a mixture of heterologous BMP4 homodimers and heterologous BMP9 homodimers or a mixture of heterologous BMP4 homodimers and heterologous GDF5 homodimers for inducing the BMP-dependent response in the cell having the overexpressed BMPR1B-like BMP receptor profile; or a mixture of heterologous BMP4 homodimers and heterologous BMP9 homodimers or a mixture of heterologous BMP4 homodimers and heterologous BMP10 homodimers for inducing the BMP-dependent response in the cell having the ALK1 NMuMG-like BMP receptor profile.

A method of identifying a combination of ligands that is capable of activating a first cell type by inducing a ligand-dependent response through interaction with ligand receptors on the first cell type, the combination of ligands selected from a plurality of ligands in a ligand-receptor signaling pathway, the combination of ligands comprising a first ligand and a second ligand, the method including: exposing the first cell type to a range of concentrations for each of the plurality of ligands; assaying for the ligand-dependent response in the first cell type over the range of concentrations for each of the plurality of ligands; quantifying the ligand-dependent response across a range of concentrations for each of the plurality of ligands; exposing the first cell type to each combination of ligands from the plurality of ligands; assaying for the ligand-dependent response in the first cell type for each combination of ligands; quantifying the ligand-dependent response for each combination of ligands; comparing the ligand-dependent response for each of the plurality of ligands to the ligand-dependent response for each combination of ligands; and identifying the combination of ligands that activate the first cell type by inducing an additive or synergistic ligand-dependent response.

The method of identifying a combination of ligands that is capable of activating a first cell type by inducing a ligand-dependent response through interaction with ligand receptors on the first cell type wherein quantifying the ligand-dependent response across the range of concentrations for each of the plurality of ligands includes identifying the minimal concentration for each of the plurality of ligands to induce a saturating ligand-dependent response, and wherein assaying for the ligand-dependent response in the first cell type for each combination of ligands includes assaying a plurality of mixtures of the combination of ligands, the plurality of mixtures includes increasing concentrations of the first ligand mixed with at least the minimum saturating concentration of the second ligand and increasing concentrations of the second ligand mixed with at least the minimum saturating concentration of the first ligand, the method further including: calculating a Relative Ligand Strength (RLS) and the Ligand Interference Coefficient (LIC) for each combination of ligands, the RLS being the ratio of the activation response of the more weakly interacting ligand ($L_{weak}$) to the activation response of the more strongly activating ligand ($L_{strong}$), represented by Equation B $$RLS = \frac{L_{weak}}{L_{strong}} \quad \text{(Equation B)}$$

and the LIC represented by Equation C $$LIC = \frac{\min}{L_{weak}} - \frac{L_{strong}}{\max} \quad \text{(Equation C)}$$

where
min is the minimum ligand-dependent response observed across the plurality of mixtures of the combination of ligands,
max is the maximum ligand-dependent response observed across the plurality of mixtures of the combination of ligands,
$L_{weak}$ is the activation response of the more weakly interacting ligand, and
$L_{strong}$ is the activation response of the more strongly interacting ligand,
wherein the combination of ligands having an RLS value of about 1 or greater and an LIC value of about 0 or greater activate the first cell type by inducing an additive or synergistic ligand-dependent response.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4C shows ligand matrices of measured pathway relative activity shown in blue, green, orange, or yellow as indicated in an independent BMP response element (BRE)-based sensor cell line (NMuMG D1 cell line) generated from NMuMG cells using a different integration technique (PiggyBAC method as disclosed herein), the results showing that exposure to the same BMP ligand pairs results in similar combined responses to the NMuMG reporter cells as shown in FIGS. 3C-3E, according to embodiments of the present invention.

FIG. 4D shows ligand matrices of measured pathway activities using ligands (BMP4, BMP10, and GDF5 as indicated) acquired from a different source (PeproTech®) in which similar responses to those acquired from R&D Systems® in FIGS. 3D-3E, according to embodiments of the present invention.

FIG. 11A is a schematic of a representative interaction when two ligands are equivalent (similar arrow thicknesses), they combine additively, where upper and middle arrow thicknesses indicate the affinities $K_{ij}^D$ and $K_{ijk}^T$, respectively, and lower arrow thicknesses indicate the phosphorylation rate of each signaling complex $\varepsilon_{ijk}$, according to embodiments of the present disclosure.

FIG. 11B is a schematic of a representative interaction when different ligands generate different levels of activity in complex with the same receptors (thin vs. thick bottom arrows), the less active ligand (blue) competitively inhibits the more active ligand (green), leading to ratiometric behavior, where upper and middle arrow thicknesses indicate the affinities $K_{ij}^D$ and $K_{ijk}^T$, respectively, and lower arrow thicknesses indicate the phosphorylation rate of each signaling complex $\varepsilon_{ijk}$, according to embodiments of the present disclosure.

FIG. 11C is a schematic of a representative interaction when imbalance detection regimes occur when affinity and activity parameters enable ligands to preferentially form less active complexes, where upper and middle arrow thicknesses indicate the affinities $K_{ij}^D$ and $K_{ijk}^T$, respectively, and lower arrow thicknesses indicate the phosphorylation rate of each signaling complex $\varepsilon_{ijk}$, according to embodiments of the present disclosure.

FIG. 11D is a schematic of a representative interaction when balance detection regimes occur when affinity and activity parameters enable ligands to preferentially form more active complexes, where upper and middle arrow thicknesses indicate the affinities $K_{ij}^D$ and $K_{ijk}^T$, respectively, and lower arrow thicknesses indicate the phosphorylation rate of each signaling complex $\varepsilon_{ijk}$, according to embodiments of the present disclosure.

DETAILED DESCRIPTION

Aspects of some embodiments of the present disclosure are based on the discovery of new methods to manipulate the behavior of signaling pathways through the use of the pathway's extracellular ligands and receptors. Signaling pathways are used to convert extracellular ligand concentrations into intracellular protein levels. Several of the intercellular signaling pathways have multiple ligand and receptor variants that interact promiscuously with one another to combinatorially generate a large set of distinct signaling complexes. The Bone Morphogenetic Protein (BMP) signaling pathway comprises multiple ligands and receptors that interact promiscuously with one another, and typically appear in combinations. As disclosed herein, and schematically shown in FIG. 1A, the BMP pathway processes multi-ligand inputs using a specific repertoire of computations, including additive, ratiometric sensing, balance detection and imbalance detection. These computations according to some embodiments of the present disclosure, operate on the relative levels of different ligands, and may arise directly from competitive receptor-ligand interactions. Furthermore, different cell types are capable of selecting different computations to perform on the same ligand combination through expression of alternative sets of receptor variants.

Figure 1A:
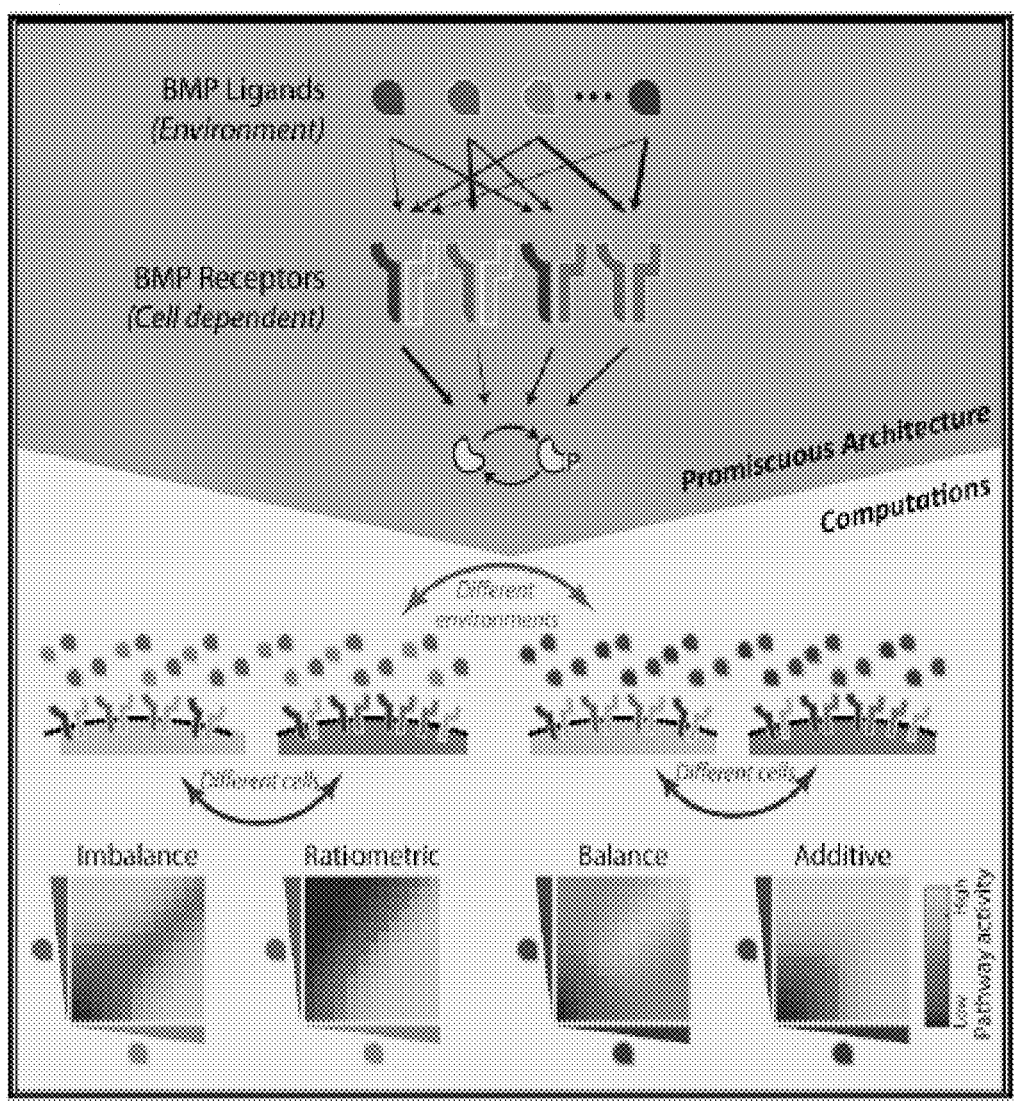
FIG. 1A is a schematic depicting how promiscuous receptor-ligand interactions can be analyzed in terms of multi-dimensional ligand and receptor spaces with t bone morphogenetic protein (BMP) ligand variants depicted by different colors (dark blue, light blue, light green, dark green) and distinct BMP receptors depicted by different colors (purple, yellow, pink, orange), according to embodiments of the present invention.
Figure 1B:
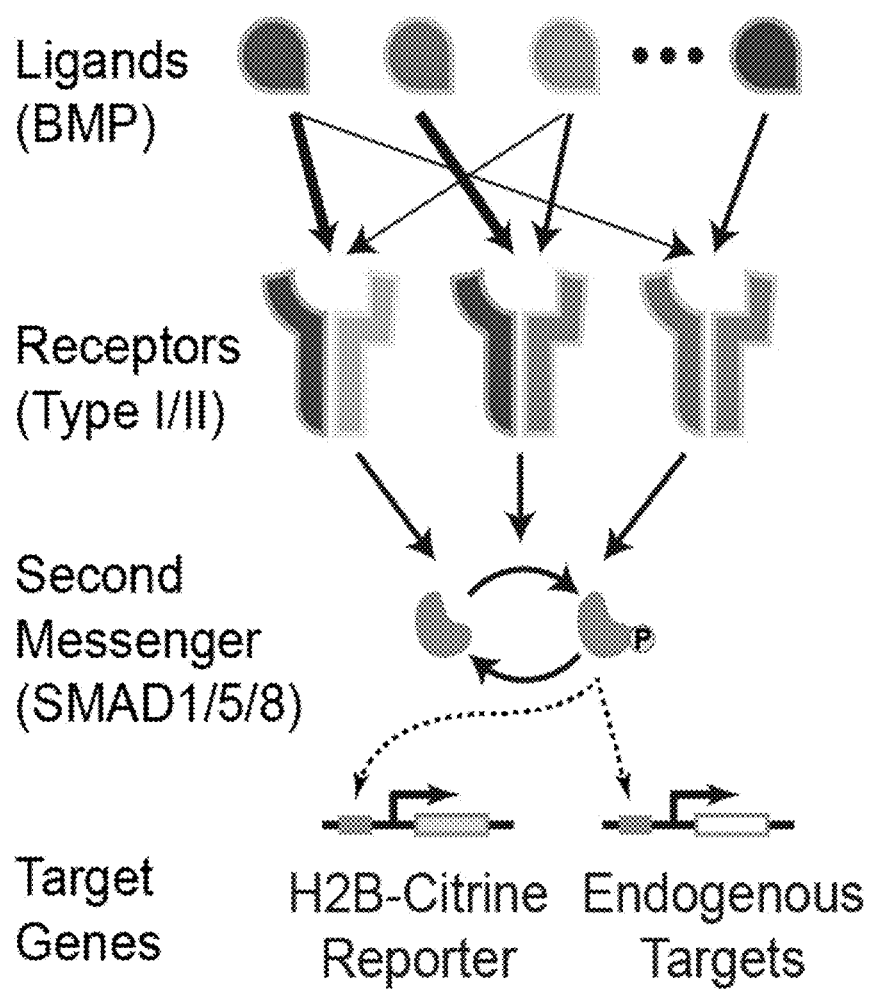
FIG. 1B depicts the BMP signaling pathway with multiple ligand variants (blue, green) interacting promiscuously with multiple distinct type I (orange, yellow)-type II (purple, pink) receptor heterodimers, where ligands interact with multiple receptor complexes (arrows), but all active signaling complexes phosphorylate the same second messenger, SMAD1/5/8 (indicated by the yellow P), and phosphorylated SMAD1/5/8 in complex with SMAD4 activates endogenous targets (white) and a stably integrated fluorescent reporter gene (e.g., H2B-Citrine) (yellow), according to embodiments of the present invention.

The BMP pathway is an example of a promiscuous receptor-ligand architecture as shown in FIG. 1A. In mammalian species, the BMP pathway includes more than 20 distinct BMP ligands, 4 type I receptors (BMPR1A, BMPR1B, ACVR1, and ALK1) and 3 type II receptors (BMPR2, ACVR2A, and ACVR2B). These components could interact in combination to form hundreds of distinct receptor-ligand signaling complexes, each composed of 2 type I and 2 type II receptors binding a dimeric ligand. Active signaling complexes phosphorylate SMAD1, 5 and 8 (SMAD1/5/8), which, together with SMAD4, translocate to the nucleus to regulate target gene expression.

As used herein, a "ligand-dependent response" refers to a molecular action in a cell caused by a ligand binding to a receptor on the cell. For example, a "BMP-dependent response" or a "BMP ligand-dependent response" may be used interchangeably to refer to a BMP protein binding to a BMP receptor. For example, BMP receptor activation by BMP ligand binding results in the phosphorylation of SMAD1/5/8. The phosphorylation of SMAD1/5/8 may be measured directly or by a downstream event such as the expression of gene targeted by phosphorylated SMAD1/5/8.

As used herein, "dynamic range," "range of dynamic concentrations," and "dynamic concentration range," each refer interchangeably to the range encompassing the minimal concentration of a ligand to induce a measurable ligand-dependent response to the minimal concentration of a ligand to induce a saturating ligand-dependent response.

With reference to FIGS. 1B-1E, the methods and compositions as disclosed herein for inducing a BMP ligand-dependent response were elucidated utilizing a BMP ligand-dependent fluorescent reporter assay that expresses a fluorescent reporter protein upon BMP ligand-receptor binding. By integrating the fluorescent reporter assay into different cell types having different BMP receptor profiles (i.e., different receptor configurations) and exposing these different cell types to different combinations of BMP ligands (i.e., different environments), methods and compositions were identified for selectively inducing a BMP ligand-dependent response. Moreover, analysis of the BMP ligand-dependent responses of combinations of ligands compared with responses from the corresponding single BMP ligands, resulted in one of four types of responses—imbalance, ratiometric, balance, and additive. In the context of certain cell types, the pairing of two BMP ligands may result in a specific response not observed for the individual BMP ligands.

In some embodiments of the present disclosure, methods and compositions are disclosed for inducing a bone morphogenetic protein (BMP)-dependent response in a cell. In some embodiments, the induction of the BMP-dependent response is selective for a specific cell type or specific cell subtype having a distinct set of BMP receptors. As used herein, a specific cell type has the same BMP receptors, and a specific cell subtype has at least one of the same BMP receptors.

With reference to FIGS. 2A-2H, 3A-3H, and 4A-4G, in some embodiments of the present disclosure, a method of inducing a bone morphogenetic protein (BMP)-dependent response in a mouse mammary gland (NMuMG) BMP receptor cell or a NMuMG-like BMP receptor cell includes exposing the NMuMG-like BMP receptor cell to the single heterologous BMP ligands of BMP4, BMP9, or BMP10 or to a mixture of heterologous BMP4 and BMP9. In some embodiments, a NMuMG-like BMP receptor cell expresses the same BMP receptor profile as the NMuMG cell. In some embodiments, as shown in the receptor expression graph of FIG. 12B, NIH3T3 cells express the same BMP receptors as NMuMG cells. In particular, the NMuMG BMP receptor cells and the NMuMG-like BMP receptor cells express the BMPR1A, BMPR2, and ACVR1 receptors. In some embodiments, expression of a BMP receptor refers to a receptor expression of at least 5 fragments per kilo million (FPKM) as measured by RNA sequencing.

In some embodiments of the present disclosure, the BMP4, BMP9, and BMP10 ligands are homodimers. In some embodiments of the present invention, the dynamic range for BMP4, BMP9, and BMP10 homodimer ligands for inducing a BMP-dependent response in NMuMG-like BMP receptor cells is from about 10 ng/ml to about 1,000 ng/ml. In other embodiments, a suitable concentration range for BMP4, BMP9, and/or BMP10 homodimers in NMuMG-like BMP receptor cells is selected from about 15 ng/ml to about 1,000 ng/ml, about 30 ng/ml to about 1,000 ng/ml, about 50 ng/ml to about 1,000 ng/ml, about 100 ng/ml to about 1,000 ng/ml, about 200 ng/ml to about 1,000 ng/ml, about 300 ng/ml to about 1,000 ng/ml, about 400 ng/ml to about 1,000 ng/ml, about 500 ng/ml to about 1,000 ng/ml, about 600 ng/ml to about 1,000 ng/ml, about 700 ng/ml to about 1,000 ng/ml, about 800 ng/ml to about 1,000 ng/ml, or about 900 ng/ml to about 1,000 ng/ml.

Figure 12A:
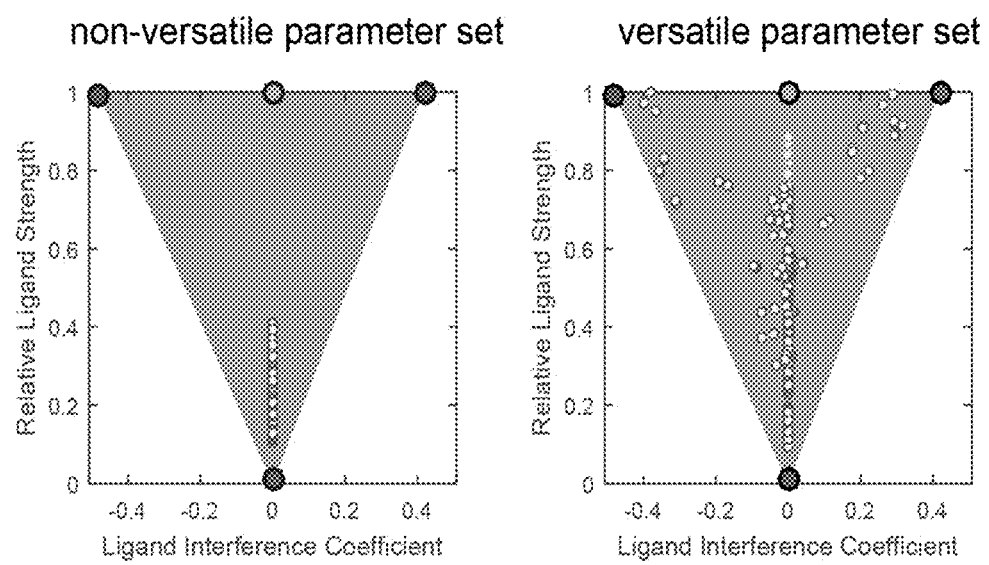
FIG. 12A is a graphical comparison of two simulated biochemical parameter sets, where for each set, multiple receptor expression profiles are plotted (individual dots), and dot color indicates the most similar archetype, for one parameter set (non-versatile, left), receptor expression only weakly affected computation, and for the other parameter set (versatile, right), variation in receptor expression generates the full range of possible computations, according to embodiments of the present disclosure.
Figure 12B:
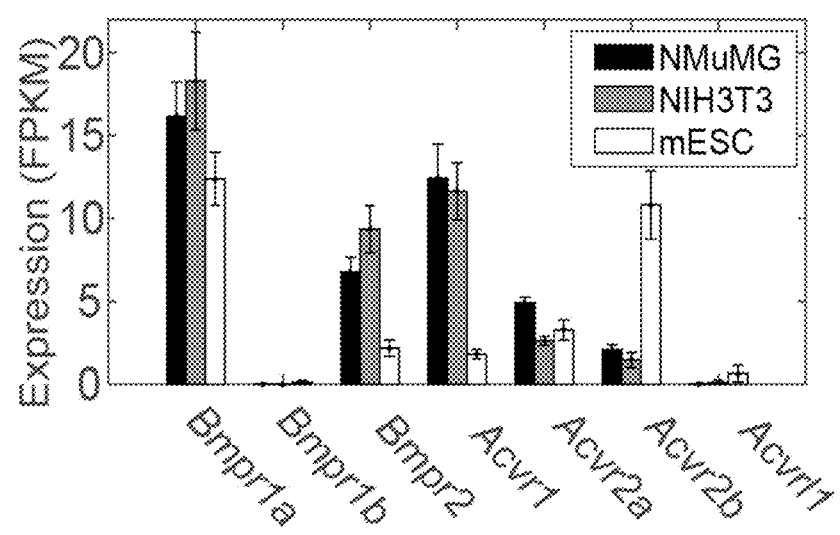
FIG. 12B is a graph showing BMP receptor expression profiles for three cell lines, as indicated where bars indicate expression levels of each receptor (FPKM), and error bars represent standard deviation of three independent biological replicates, according to embodiments of the present disclosure.

With reference to FIGS. 12A-12H and FIGS. 13A-13C, in some embodiments of the present disclosure, a method of inducing a bone morphogenetic protein (BMP)-dependent response in an embryonic stem cell (ESC) BMP receptor cell or an ESC-like BMP receptor cell includes exposing the ESC-like BMP receptor cell to a mixture of heterologous BMP4 and BMP9. In some embodiments, a ESC-like BMP receptor cell expresses the same BMP receptor profile as the ESC cell. In particular, as shown in FIG. 12B, the ESC BMP receptor cells and the ESC-like BMP receptor cells express the BMPR1A and ACVR2B receptors. In some embodiments, expression of a BMP receptor refers to a receptor expression of at least 5 fragments per kilo million (FPKM) as measured by RNA sequencing.

Figure 12E:
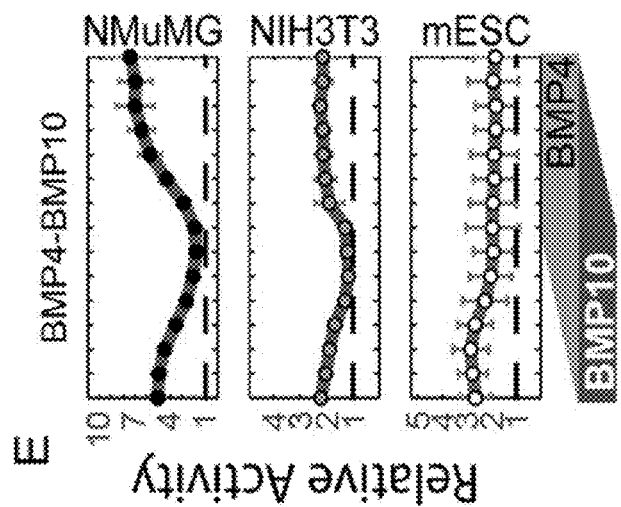
FIG. 12E shows computation correlates with receptor expression pattern for ligand pairs (BMP4-BMP10) in NMuMG cells, NIH3T3 cells, and mouse embryonic stem cells (mESC), where each column shows the response to the same pair of ligands for the indicated pair of ligands. Note the qualitative change in function between mESCs (bottom) and the other cell lines, and line colors refer to closest archetype as in FIG. 11C, according to embodiments of the present disclosure.
Figure 12D:
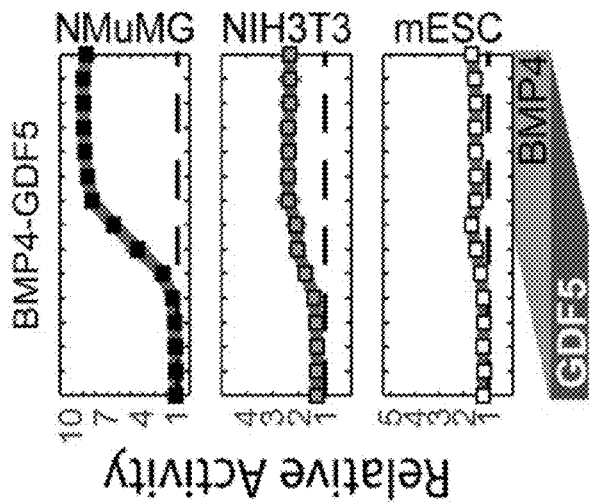
FIG. 12D shows computation correlates with receptor expression pattern for ligand pairs (BMP4-GDF5) in NMuMG cells, NIH3T3 cells, and mouse embryonic stem cells (mESC), with a significant qualitative change in function between mESCs and the other cell lines, and line colors refer to closest archetype as in FIGS. 11A-11E, according to embodiments of the present disclosure.
Figure 12C:
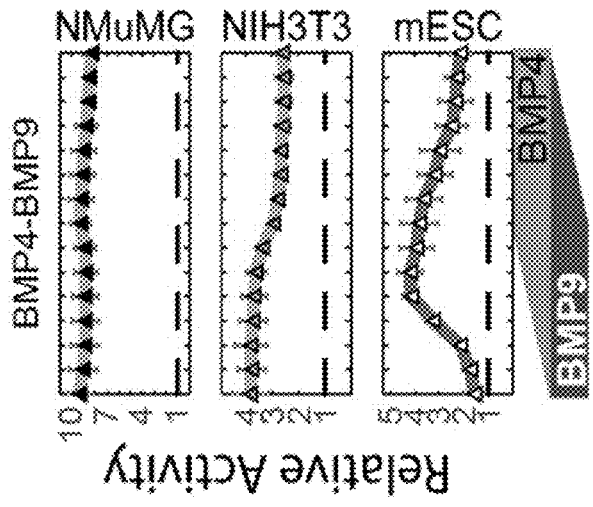
FIG. 12C shows computation correlates with receptor expression pattern for ligand pairs (BMP4-BMP9) in NMuMG cells, NIH3T3 cells, and mouse embryonic stem cells (mESC), with a significant qualitative change in function between mESCs and the other cell lines, and line colors refer to closest archetype as in FIGS. 11A-11E, according to embodiments of the present disclosure.

In some embodiments of the present disclosure, the mixture of BMP4 and BMP9 ligands are homodimers. With reference to FIG. 12C, the mixture of BMP4 and BMP9 show a balanced interaction in which their cooperative (e.g., synergistic) induction of a BMP-dependent response in ESC-like BMP receptor cells. The synergy of BMP4 and BMP9 in ESC-like BMP receptor cells occurs when the ratio of BMP4 to BMP9 is within the range of about 1.0:0.4 to about 1.0:100. Accordingly, a mixture of BMP4 and BMP9 in a ratio outside of this range, will not induce a BMP-dependent response in ESC-like BMP receptor cells, but will activate a BMP-dependent response in a NMuMG-like BMP receptor cells, the overexpressed BMPR1P NMuMG-like receptor cells, and the overexpressed ALK1 NMuMG-like receptor cells as disclosed herein.

In some embodiments of the present invention, the dynamic range for BMP4 and BMP9 homodimer ligands for inducing a BMP-dependent response in ESC-like BMP receptor cells is from about 10 ng/ml to about 1,000 ng/ml. In other embodiments, a suitable concentration range for BMP4 and BMP9 homodimers for inducing a BMP-dependent response in ESC-like BMP receptor cells is selected from about 15 ng/ml to about 1,000 ng/ml, about 30 ng/ml to about 1,000 ng/ml, about 50 ng/ml to about 1,000 ng/ml, about 100 ng/ml to about 1,000 ng/ml, about 200 ng/ml to about 1,000 ng/ml, about 300 ng/ml to about 1,000 ng/ml, about 400 ng/ml to about 1,000 ng/ml, about 500 ng/ml to about 1,000 ng/ml, about 600 ng/ml to about 1,000 ng/ml, about 700 ng/ml to about 1,000 ng/ml, about 800 ng/ml to about 1,000 ng/ml, or about 900 ng/ml to about 1,000 ng/ml.

With reference to FIGS. 12G, 12I-12J, and 13A, in some embodiments of the present disclosure, a method of inducing a bone morphogenetic protein (BMP)-dependent response in an overexpressed BMPR1B NMuMG BMP receptor cell or an overexpressed BMPR1B NMuMG-like BMP receptor cell includes exposing the overexpressed BMPR1B NMuMG-like BMP receptor cell to heterologous BMPs selected from BMP4, BMP9, BMP10, GDF5, a mixture of BMP4 and BMP9, or a mixture of BMP4 and GDF5. In some embodiments, the ALK1 NMuMG-like BMP cells may be in a population of different cell types, where inducing a BMP-dependent response in an overexpressed BMPR1B NMuMG-like BMP receptor cells includes exposing these cells to heterologous BMPs that do not induce a BMP-dependent response in another cell type in the population of different cell types, thereby selectively inducing the overexpressed BMPR1B NMuMG-like BMP receptor cells. For example, a mixture of BMP4 and GDF5 does not induce NMuMG-like BMP receptor cells, ESC-like BMP receptor cells, or the overexpressed ALK1 NMuMG-like BMP receptor cells.

In some embodiments, overexpressed BMPR1B NMuMG-like BMP receptor cell expresses the same BMP receptor profile as an overexpressed BMPR1B NMuMG BMP receptor cell. In particular, the overexpressed BMPR1B NMuMG BMP receptor cells and the overexpressed BMPR1B NMuMG-like BMP receptor cells are genetically modified to express the BMPR1B receptors in a cell that does not express native BMPR1B. Overexpression of BMPR1B may include high levels of receptor expression, but overexpression also refers to engineered expression of a BMP receptor in a cell that does not otherwise express the BMP receptor. Accordingly, expression and overexpression of a BMP receptor refers to receptor expression of at least 5 fragments per kilo million (FPKM) as measured by RNA sequencing.

In some embodiments of the present disclosure, the BMP4, BMP9, BMP10, and GDF5 ligands are homodimers. In some embodiments of the present invention, the dynamic range for BMP4, BMP9, BMP10, and GDF5 homodimer ligands for inducing a BMP-dependent response in overexpressed BMPR1B NMuMG-like BMP receptor cells is from about 10 ng/ml to about 1,000 ng/ml. In other embodiments, a suitable concentration range for BMP4, BMP9, BMP10, and/or GDF5 homodimers in overexpressed BMPR1B NMuMG-like BMP receptor cells is selected from about 15 ng/ml to about 1,000 ng/ml, about 30 ng/ml to about 1,000 ng/ml, about 50 ng/ml to about 1,000 ng/ml, about 100 ng/ml to about 1,000 ng/ml, about 200 ng/ml to about 1,000 ng/ml, about 300 ng/ml to about 1,000 ng/ml, about 400 ng/ml to about 1,000 ng/ml, about 500 ng/ml to about 1,000 ng/ml, about 600 ng/ml to about 1,000 ng/ml, about 700 ng/ml to about 1,000 ng/ml, about 800 ng/ml to about 1,000 ng/ml, or about 900 ng/ml to about 1,000 ng/ml.

With reference to FIGS. 12H-12J and 13A in some embodiments of the present disclosure, a method of inducing a bone morphogenetic protein (BMP)-dependent response in an overexpressed ALK1 NMuMG BMP receptor cell or an overexpressed ALK1 NMuMG-like BMP receptor cell includes exposing the overexpressed ALK1 NMuMG-like BMP receptor to heterologous BMPs selected from BMP4, BMP9, and BMP10, a mixture of BMP4 and BMP9, or a mixture of BMP4 and BMP10. In some embodiments, the ALK1 NMuMG-like BMP cells may be in a population of different cell types, where inducing a BMP-dependent response in an overexpressed ALK1 NMuMG-like BMP receptor cells includes exposing these cells to heterologous BMPs that do not induce a BMP-dependent response in another cell type of the population of different cell types, thereby selectively inducing the overexpressed ALK1 NMuMG-like BMP cells. For example, a mixture of BMP4 and BMP10 does not induce NMuMG-like BMP receptor cells, ESC-like BMP receptor cells, or the overexpressed BMPR1B NMuMG-like BMP receptor cells.

In some embodiments, overexpressed ALK1 NMuMG-like BMP receptor cell expresses the same BMP receptor profile as an overexpressed ALK1 NMuMG BMP receptor cell. In particular, the overexpressed BMPR1B ALK1 BMP receptor cell and the overexpressed ALK1 NMuMG-like BMP receptor cell are genetically modified to express the ALK1 receptors in a cell that does not express native ALK1. Overexpression of ALK1 may include high levels of receptor expression, but overexpression also refers to engineered expression of a BMP receptor in a cell that does not otherwise express the BMP receptor. Accordingly, expression and overexpression of a BMP receptor refers to receptor expression of at least 5 fragments per kilo million (FPKM) as measured by RNA sequencing.

In some embodiments of the present disclosure, the BMP4, BMP9, and BMP10 ligands are homodimers. In some embodiments of the present invention, the dynamic range for BMP4, BMP9, and BMP10 homodimer ligands for inducing a BMP-dependent response in overexpressed ALK1 NMuMG-like BMP receptor cells is from about 10 ng/ml to about 1,000 ng/ml. In other embodiments, a suitable concentration range for BMP4, BMP9, and/or BMP10 homodimers in overexpressed ALK1 NMuMG-like BMP receptor cells is selected from about 15 ng/ml to about 1,000 ng/ml, about 30 ng/ml to about 1,000 ng/ml, about 50 ng/ml to about 1,000 ng/ml, about 100 ng/ml to about 1,000 ng/ml, about 200 ng/ml to about 1,000 ng/ml, about 300 ng/ml to about 1,000 ng/ml, about 400 ng/ml to about 1,000 ng/ml, about 500 ng/ml to about 1,000 ng/ml, about 600 ng/ml to about 1,000 ng/ml, about 700 ng/ml to about 1,000 ng/ml, about 800 ng/ml to about 1,000 ng/ml, or about 900 ng/ml to about 1,000 ng/ml.

Methods for Combinatorial Specificity

In some embodiments of the present disclosure, combinations of BMPs activate distinct cell types more specifically than single BMPs. Single BMPs tend to nonspecifically activate all cells that express any of the many BMP receptors that can activate the pathway. However, a mixture of the single BMPs will not necessarily activate the pathway to the same extent in all cell types, particularly in cases where the BMPs effectively antagonize each other. As such, to compose a combination of BMPs that selectively activate a tissue or cell type of interest, one must know how that target cell type responds to single BMPs and to BMP combinations, and how that profile of responses is different from other cell types.

Because predicting how BMPs behave in combinations is difficult to predict, the full profile of cell responses to BMPs must be measured directly. Accordingly, in some embodiments of the present disclosure, a given cell type is exposed to many possible combinations of BMP ligand pairs to quantify and characterize a BMP-dependent cellular response for that cell type. Even without understanding the precise molecular details of how each BMP uniquely binds the available BMP receptors, one can observe subtle differences in the cellular response to BMP combinations.

In some embodiments of the present disclosure, determining the combinations of BMPs that could selectively activate a given cell type requires a full map of responses to many different BMP combinations.

In some embodiments of the present disclosure, exposing cells to a range of concentrations for a BMP ligand reveals the dynamic range of that ligand. This is the range defined by the minimal concentration to induce a measurable pathway response and the minimal concentration to induce a nearly saturating response, as defined more specifically below.

A cell's response to increasing concentration of BMP ligands should fit the following Hill function:

$$R(C) = R_0 \frac{1}{1 + \left(\frac{C}{K_d}\right)^n} + B, \quad \text{(Equation A)}$$

where R is the cellular response as a function of C, the concentration of BMP ligand. B is the background response in the absence of any ligand (i.e. C=0), and $R_0+B$ is the response as C→∞, or the response at saturating concentrations of ligand. $K_d$ is the effective affinity and the concentration at which the response is halfway between background and saturating levels (i.e. $B+R_0/2$), while n is the Hill coefficient. In principle, $R_0$, $K_d$, and n are all ligand-specific parameters. In some embodiments, the dynamic range might be the concentrations that induce responses equal to $B+0.05 R_0$ and $B+0.95 R_0$.

In some embodiments of the present disclosure, a single ligand pair is characterized by measuring responses at every point on a grid of logarithmically spaced points in the domain of the dynamic ranges of the two ligands. However, for large numbers of pairs, obtaining enough measurements for a high resolution grid (e.g. more than nine measurements per BMP pair), is not feasible. Accordingly, in some embodiments, each ligand pair combination is mixed in concentrations following a set of minimally informative measurements.

Figure 15B:
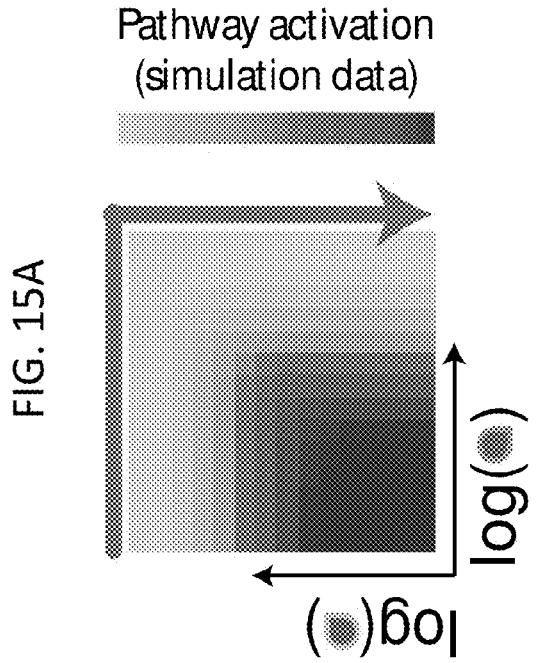
FIG. 15B is a graph of ligand activation where red shows the response to Ligand 1 only, blue shows the response to the Ligand 2 only, and purple shows the response to the mixture of ligands, and each response was simulated at the same input concentrations indicated by the purple arrow in FIG. 15A.
Figure 15B:
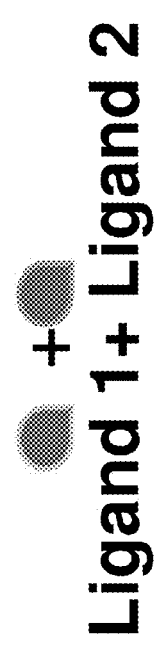
Figure 15A:
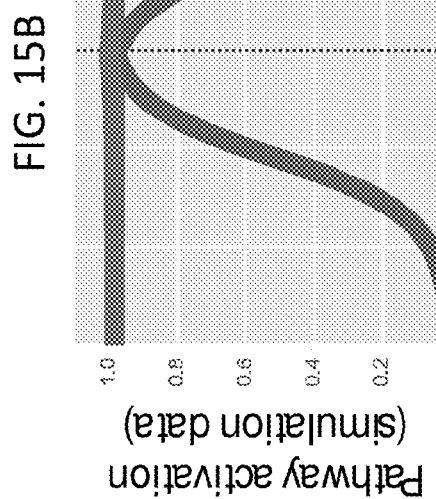
FIG. 15A is shows simulated responses to two ligands plotted in log-log space and the same pairwise relationship can be summarized by measuring only the rim defined by the purple arrow.
Figure 15A:
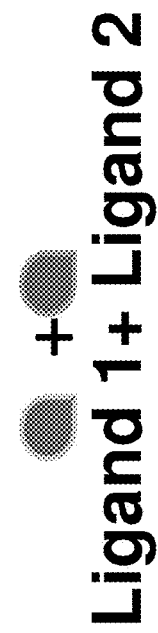

For the analysis outlined in the following section, the responses to each pair were characterized using the outermost rim as shown in FIG. 15A.

BMP pairs that selectively activate the cell type being studied will not activate other cells exposed to the same BMP pair. Therefore, the pairwise profile generated in the study must be compared to responses to BMP pairs in cells that should not be activated. As was arbitrarily defined in the case of the dynamic range, a threshold (e.g. $B+0.05R_0$) can define what levels of activation indicate that the pathway is off and that it is on. Our goal is to find a BMP input condition that activates the cell type of interest and does not activate (or minimally activates) other cell types. One systematic approach for classifying BMP responses is outlined below.

Figures 16A, 16B:
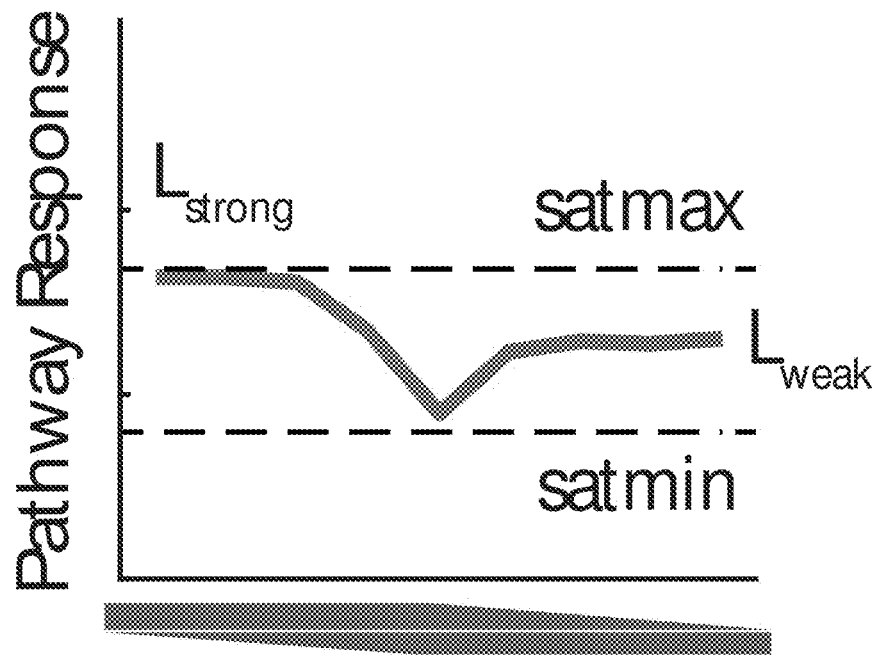
FIG. 16A is a graph showing the pathway response activity of a combination of two ligands.
FIG. 16B shows the calculation of the RLS and LIC computations, according to embodiments of the present disclosure.
Figure 17:
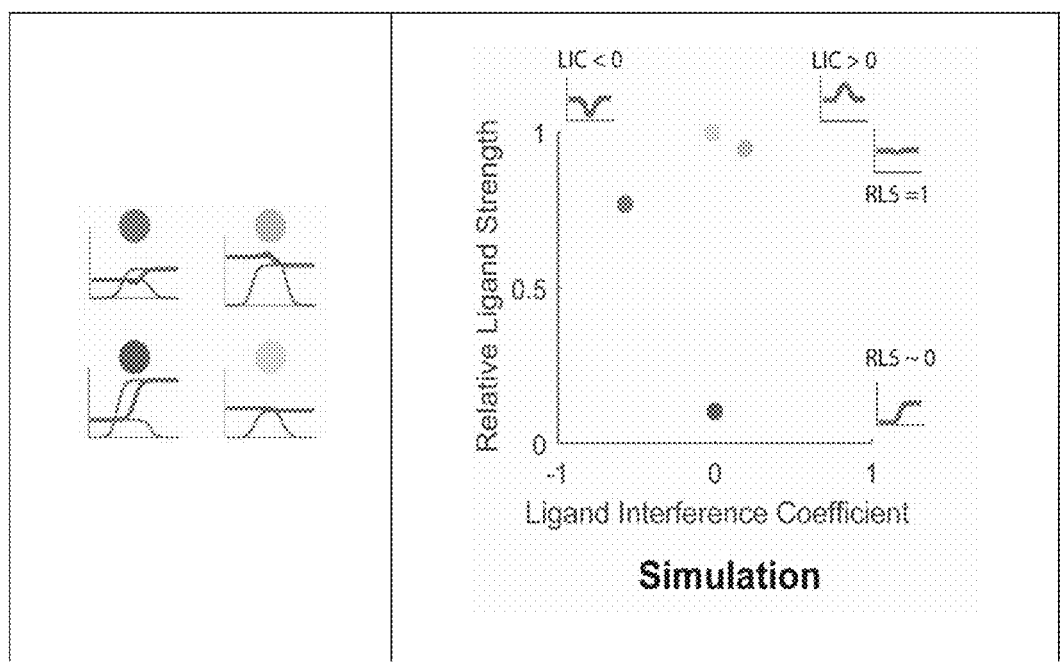
FIG. 17 shows simulation data for the 4 types of ligand activation.

Simulations of responses to BMP pairs generate a range of response curves shown in FIG. 17 whose shape and similarity can be summarized by two parameters RLS and LIC, as shown in FIGS. 16A-16B. RLS (Relative Ligand Strength) is the ratio of the extent of activation of the more weakly activating ligand to the more strongly activating. LIC (Ligand Interference Coefficient) captures the extent of synergy and antagonism between the two pairs.

Figure 18A:
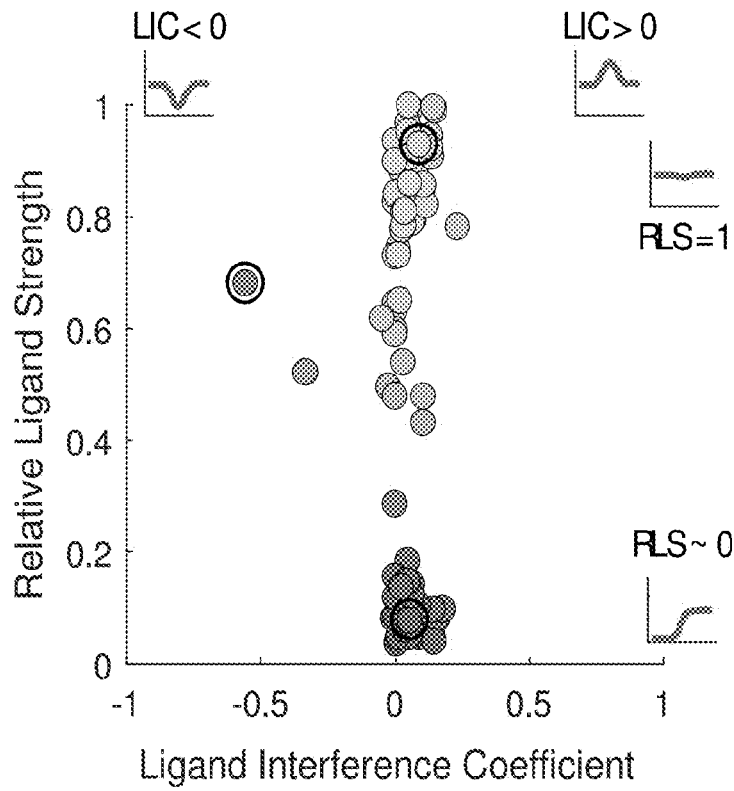
FIG. 18A is graph plotting the RLS versus the LIC of two BMP pairs in NMuMG cells.

Responses to all pairs can be plotted in the RLS v. LIC space (FIG. 18A), effectively classifying all the observed behaviors. Here, we plot responses in NMuMG, a mouse epithelial cell line, to all possible pairs of the following list of BMPs: BMP2, BMP4, BMP5, BMP6, BMP7, BMP8, BMP9, BMP10, GDF5, GDF6, GDF7, BMP2/6, BMP2/7, and BMP4/7.

Figure 18B:
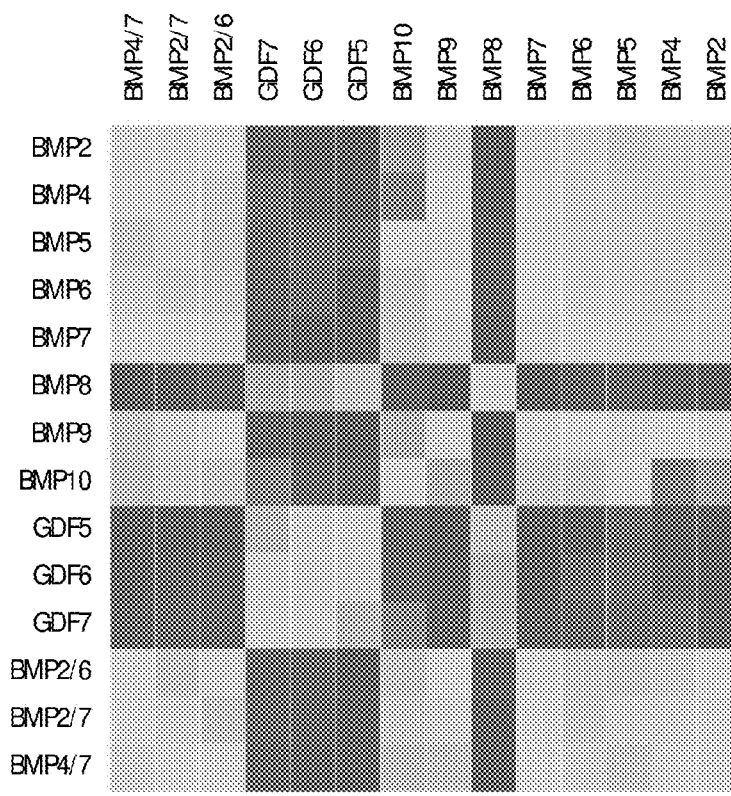
FIG. 18B plots the activity of the two BMP pairs of FIG. 18A in two dimensional space, according to embodiments of the present disclosure.

Already, this plot can serve as an effective summary of how each BMP pair activates the cell type being studied. This "pairwise behavior" plot (FIG. 18B) indicates, indirectly, how BMPs activate, or do not activate, this cell type. Comparing this pairwise behavior plot to a similar plot for a different cell type would reveal which BMP pairs are "specific" to each cell type. Responses to BMP pairs that are antagonistic in all other cell types (i.e. red or blue response types), but synergistic or additive in the cell type of interest (i.e. yellow or green response types) are good candidates for combinatorial specificity. This would be apparent as a yellow or green square, in the map for the target cell type, in the same location as blue or red squares in the maps for all other cell types that should not be activated.

The following Examples are presented for illustrative purposes only, and do not limit the scope or content of the present application.

EXAMPLES

Example 1

Combining theoretical and experimental approaches, the BMP pathway perceives ligand combinations through a specific family of multi-dimensional response profiles. These profiles allow the pathway to perceive relative, in addition to absolute, levels of multiple ligands. Mathematical modeling further reveals that these response profiles can arise from an interplay between receptor-ligand binding affinities and the quantitative activity of each complex. The former determine what complexes are formed, while the latter determine how the activities of those complexes combine to establish overall pathway activity. The response profiles differ qualitatively and quantitatively depending on the expression levels of the different receptor variants. As a result, different cell types, with distinct receptor expression profiles, may respond to distinct features in the multidimensional space of ligand concentrations. Together, these results establish a general framework for analyzing the BMP signaling pathway and reveal a more general design principle for biological signaling systems containing promiscuous receptor-ligand interactions.

Figure 1C:
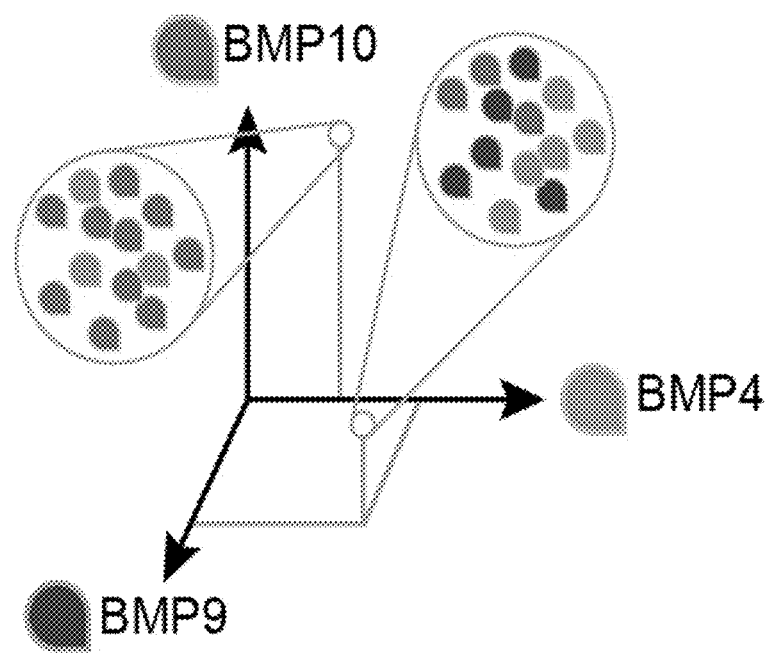
FIG. 1C shows how cellular environments and expression levels can be represented as points in multi-dimensional spaces where ligand concentration space of BMP4 (light green), BMP9 (dark green), and BMP10 (light blue)) represents the possible local environments of cells, where only these 3 ligands are plotted for simplicity, but the full space includes dimensions for each ligand species with zoomed circles indicating examples of two environments with distinct concentrations of ligands, according to embodiments of the present invention.
Figure 1D:
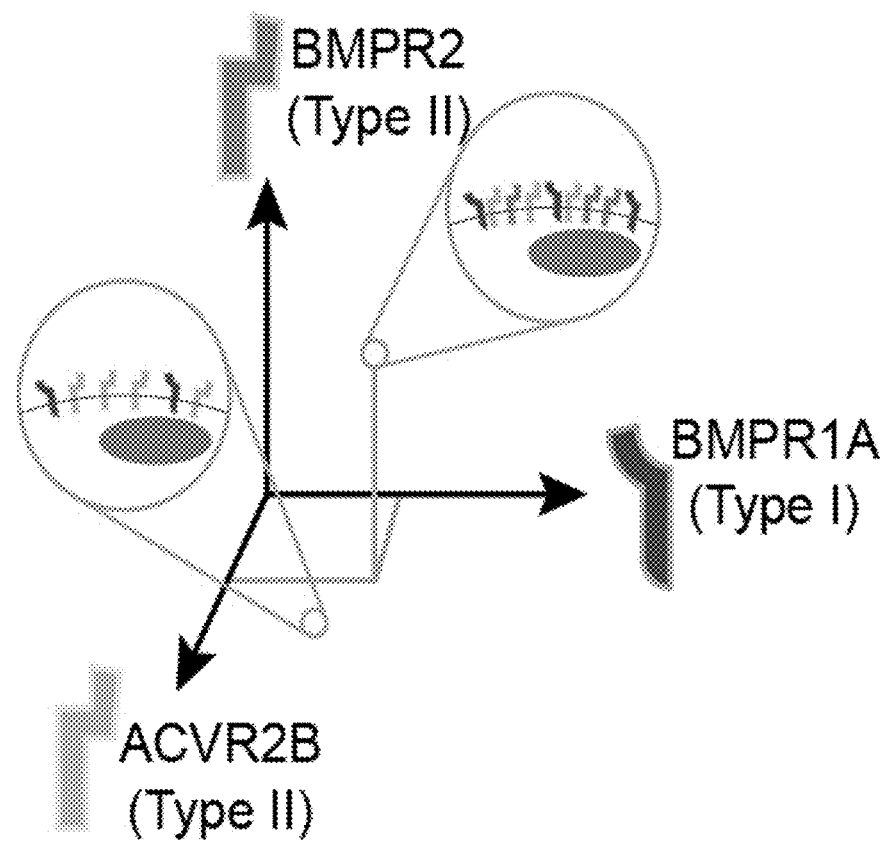
FIG. 1D shows how cellular environments and expression levels can be represented as points in multi-dimensional spaces where receptor space represents the space of possible receptor expression profiles with 3 of 7 dimensions shown—BMPR2 (orange), ACVR2B (yellow), and BMPR1A (purple)—with two example cell types with distinct receptor expression profiles indicated by small circles at the respective loci and in the magnified circles, according to embodiments of the present invention.
Figure 1E:
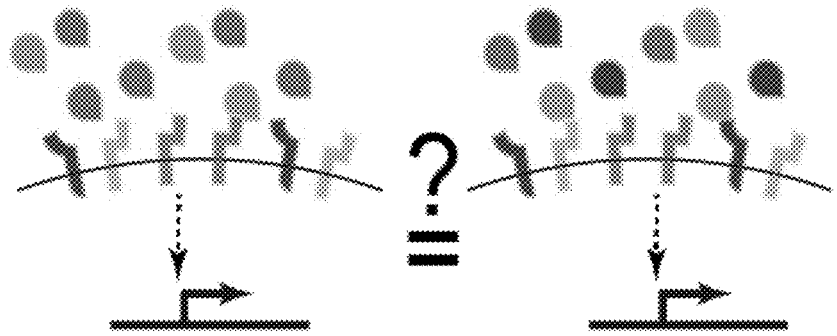
FIG. 1E is a schematic representing the question of how multiple ligands combine to determine pathway activity in a given cell type, according to embodiments of the present invention.
Figure 1F:
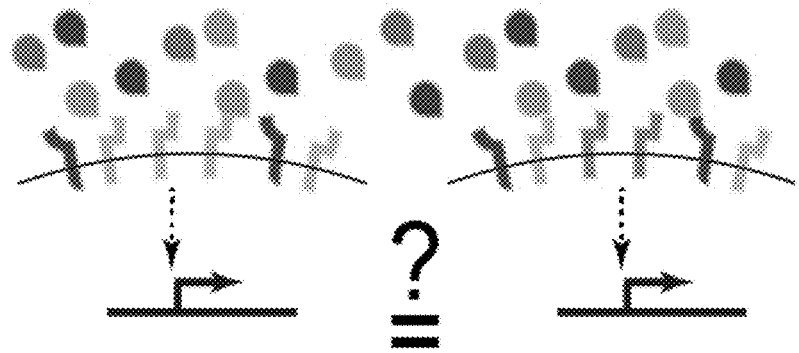
FIG. 1F is a schematic representing the question of how different cell types respond to the same ligand combination, according to embodiments of the present invention.

In order to analyze the way in which the BMP pathway uses multiple receptor variants to integrate signals from multiple dimeric ligand species, it is useful to consider two multi-dimensional spaces. Cellular environments, specified by the concentrations of each of the dimeric ligand species, can be represented as points in a multi-dimensional 'ligand space' (FIG. 1C). Similarly, individual cell types typically co-express multiple type I and type II receptors and can therefore be represented as points in a 7-dimensional 'receptor space' specified by the individual expression levels of each receptor (FIG. 1D). (This space is, more precisely, the combination of a 3-dimensional space for the type I receptors, and a 4-dimensional space for the type II receptors). Not every point in ligand or receptor space may be realized biologically, and other secreted and intracellular factors further modulate BMP signaling in specific contexts. Nevertheless, understanding signal processing by the BMP pathway requires determining how multiple ligands combine, or integrate, to control the pathway activity in a cell with a given receptor configuration (FIG. 1E), and whether distinct cells, expressing specific combinations of receptors, can integrate the same ligands in qualitatively different ways (FIG. 1F).

BMP ligands exhibit combinatorial effects. In order to address these questions experimentally, the dependence of BMP pathway activity on individual ligands and ligand combinations was measured. Ligand monomers form covalent homodimers and heterodimers with distinct activities. Here, we focused on mixtures of distinct homodimeric ligands, which have been shown to produce non-additive responses in some systems. Mixtures of heterodimeric ligands could be analyzed similarly.

Figure 2A:
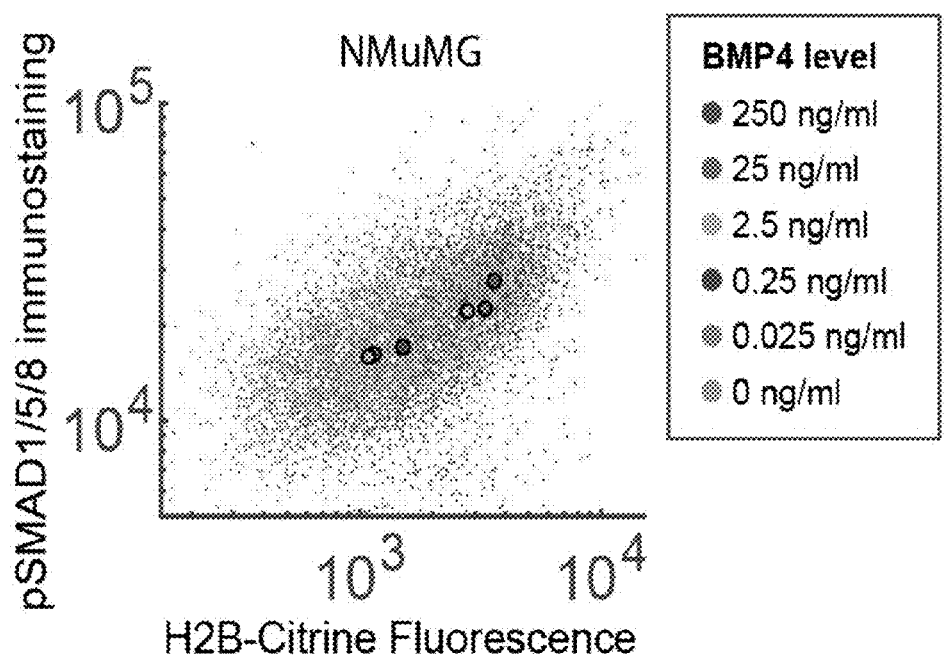
FIG. 2A is a graph of NMuMG BMP reporter cells analyzed by flow cytometry for both reporter H2B-Citrine expression (x-axis), and immunostaining of phosphorylated SMAD1/5/8 (y-axis) after treatment (e.g., stimulation) with different concentrations of BMP4 (from 0 ng/ml up to 250 ng/ml represented by variously colored dots as indicated), with a strong correlation both within (scatter) and between (larger circles) ligand concentrations, according to embodiments of the present invention.
Figure 2B:
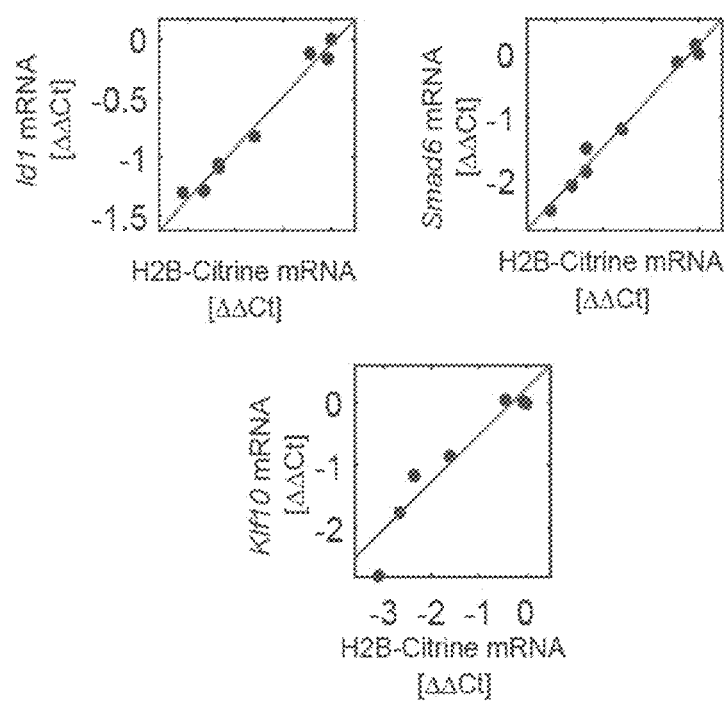
FIG. 2B is three graphs of qualitative reverse transcriptase PCR (qRT-PCR) measurements of expression levels of three endogenous BMP-responsive genes (Id1, Smad6, and Klf10), as indicated, showing a correlation of mRNA expression of these endogenous BMP-responsive genes with H2B-Citrine reporter expression, according to embodiments of the present invention.
Figure 2C:
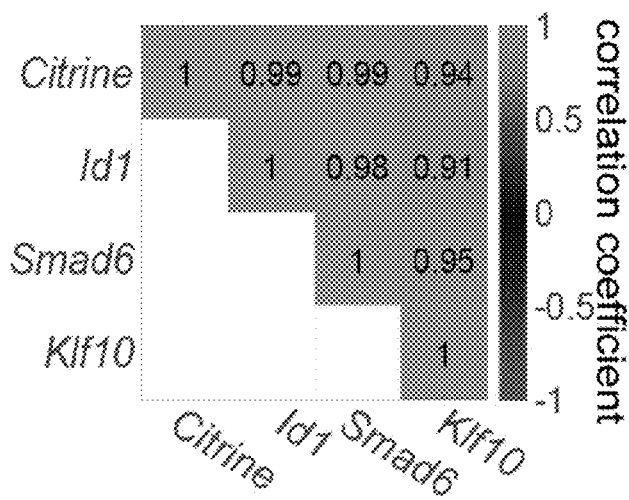
FIG. 2C shows qRT-PCR correlation coefficients for each pair of target genes shown in FIG. 5B, according to embodiments of the present invention.
Figure 2D:
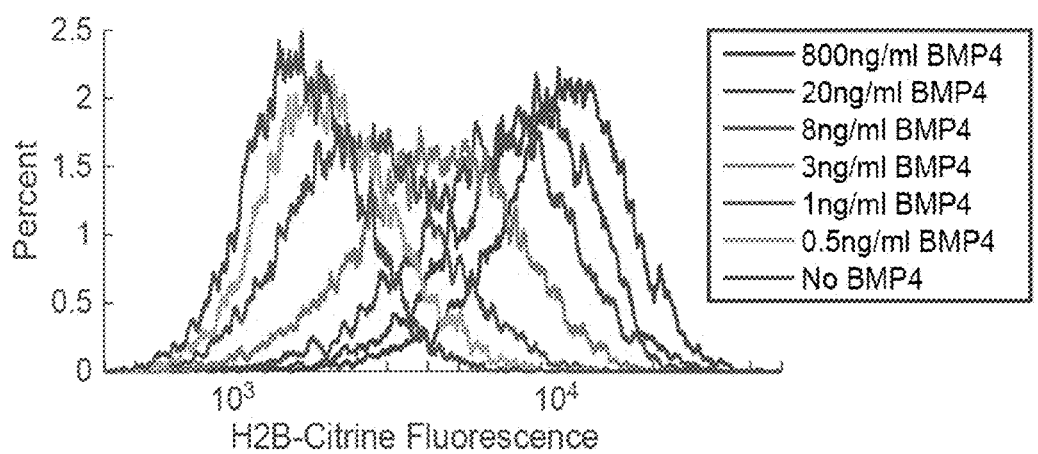
FIG. 2D is a graph showing unimodal distributions of reporter H2B-Citrine expression levels at 24 hours after stimulation of NMuMG BMP reporter cells across the indicated range of BMP4 concentrations represented by distinctly colored lines as indicated, according to embodiments of the present invention.
Figure 2E:
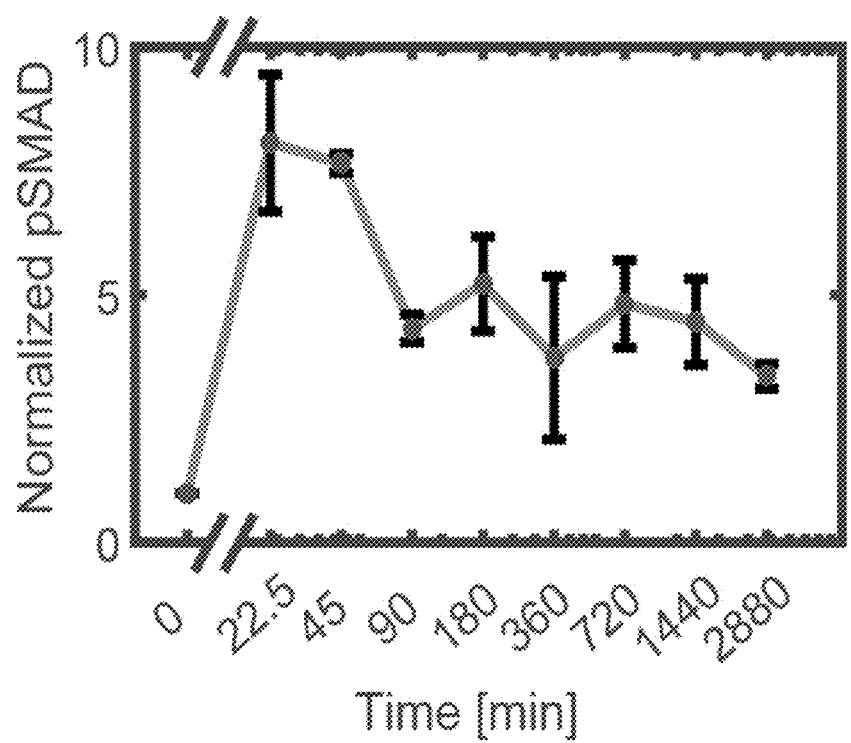
FIG. 2E is a graph measuring the normalized amount of phosphorylated SMAD1/5/8 in NMuMG BMP reporter cells when measured using immunoblotting at time-points up to 48 hours (2880 minutes) after BMP addition where after a short transient of a few hours, phosphorylated SMAD1/5/8 levels remained constant, with the plot showing mean and standard deviation (error bars) of 3 independent repeats, according to embodiments of the present invention.
Figure 2F:
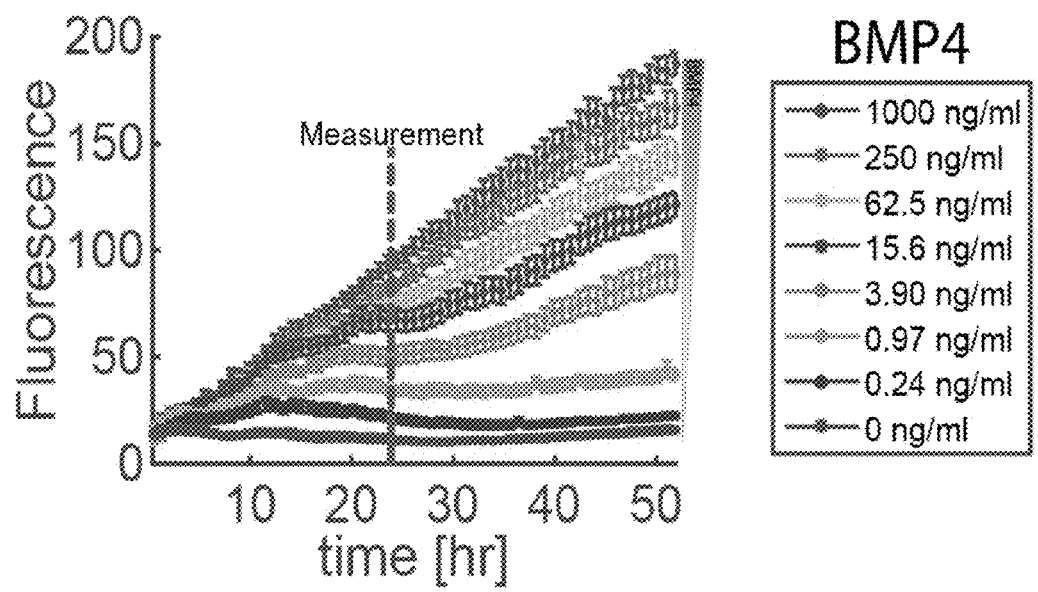
FIG. 2F is two graphs each measuring fluorescence over time in NMuMG BMP reporter cells that were exposed to different concentrations of BMP4 (top graph) (from 0 ng/ml up to 1000 ng/ml represented by variously colored dots as indicated) or BMP10 (bottom graph) (from 0 ng/ml up to 3000 ng/ml represented by variously colored dots as indicated) for which fluorescence was monitored using time-lapse microscopy over more than 48 hours, increases in mean fluorescence per cell occurred in most conditions, and the vertical dashed line indicates the 24 hour time point, according to embodiments of the present invention.
Figure 2F:
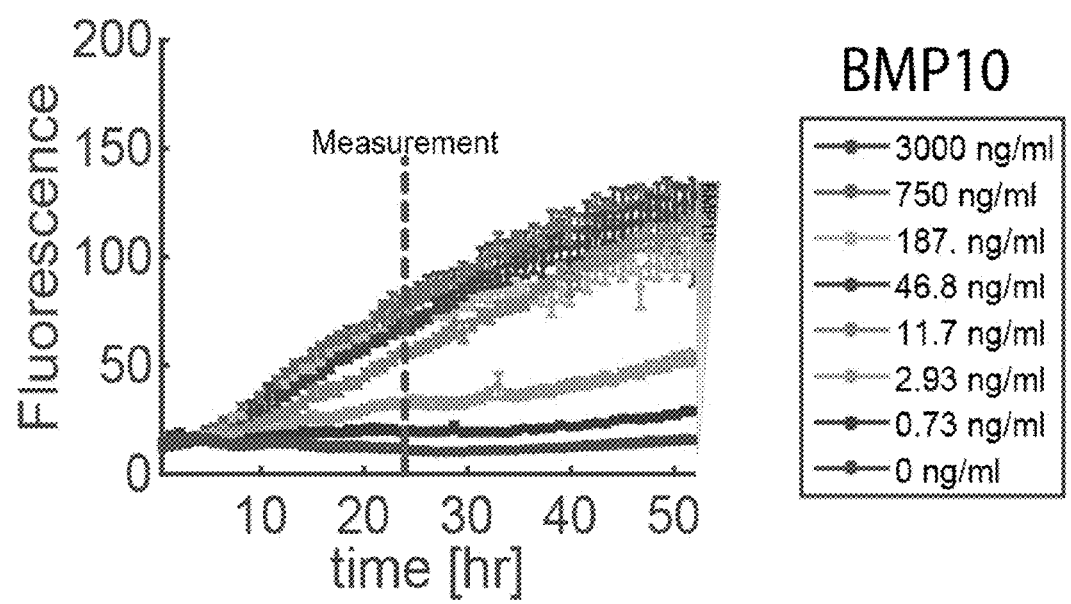

To quantitatively measure BMP pathway activity, a reporter cell line was constructed, by stably integrating a Histone 2B (H2B)-Citrine fluorescent reporter driven by a BMP response element (BRE) specific for SMAD1/5/8 into the NAMRU mouse mammary gland (NMuMG) epithelial cell line, in which the BMP pathway can be activated without inducing differentiation. Reporter expression correlated with phosphorylation of SMAD1/5/8 and with endogenous BMP target gene expression FIGS. 2A-2C and exhibited a unimodal distribution for each ligand concentration (FIG. 2D). After an elevated transient response to BMP addition, pSMAD levels reached a steady state within 90 min (FIG. 2E). The steady-state behavior was also reflected in reporter fluorescence, which accumulated at an approximately constant rate over time for up to 48h (FIG. 2F). (Since the fluorescent protein is stable and the cell cycle is greater than 24h in these conditions, linear accumulation indicates a constant rate of reporter expression.) Based on these dynamics, a 24h post-induction was selected as a time-point for subsequent analysis.

Example 4

Figure 3A:
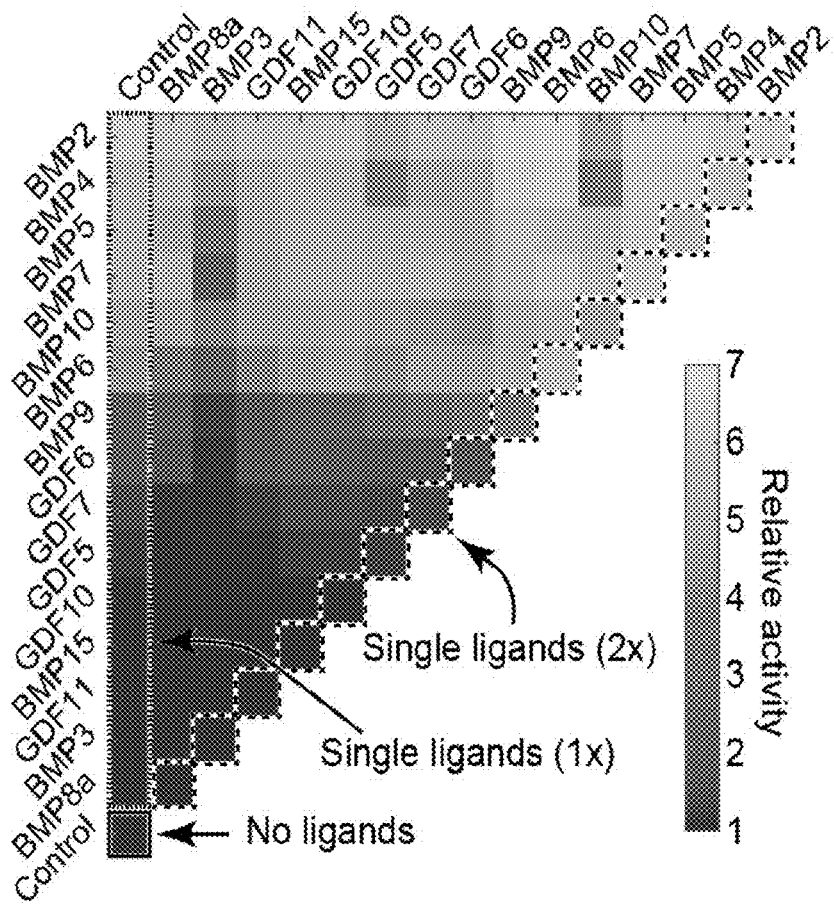
FIG. 3A is a ligand matrix of a low resolution ligand survey of reporter H2B-Citrine expression in NMuMG BMP reporter cells exposed to 136 different combinatorial pairings of 15 homodimeric BMP ligands, as indicated, in which the color scale indicates mean fluorescence level at 24 hours, normalized by the uninduced population ('relative activity'), with the relative activity of reporter H2B-Citrine expression shown in blue, green, orange, or yellow as indicated, according to embodiments of the present invention.
Figure 3B:
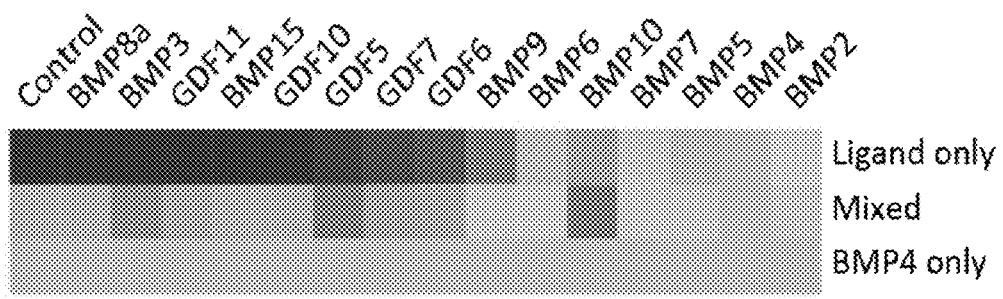
FIG. 3B is a ligand matrix showing the relative activity of the individual response as measured by reporter H2B-Citrine expression in NMuMG BMP reporter cells to each ligand (top row) compared to the response to BMP4 (bottom row) and to mixtures of each ligand with BMP4 (middle row) showing that specific ligands combine with BMP4 in different ways, both synergistically and antagonistically, with the relative activity of reporter H2B-Citrine expression shown in blue, green, orange, or yellow as indicated, according to embodiments of the present invention.

As a first step to classifying ligand integration behaviors, candidate ligand pairs were identified for subsequent higher resolution analysis. A coarse-grained survey was performed of 15 commercially available homodimeric ligands (FIG. 3A). Reporter expression was measured in response to each ligand individually, at a specific base concentration; each ligand at twice its base concentration (diagonal elements); and each pair of ligands at their base concentrations (other matrix elements). To quantify pathway activity, each measurement by basal activity was normalized with no added ligand (bottom).

Figure 2G:
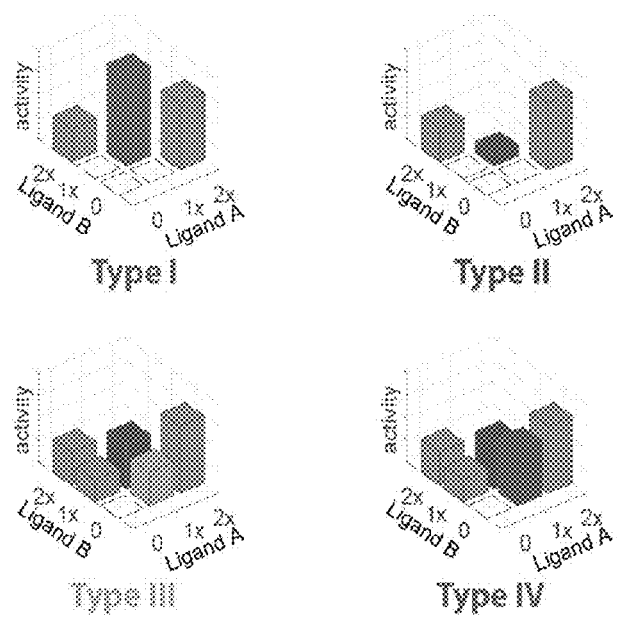
FIG. 2G is a schematic showing 4 modes of ligand integration, according to embodiments of the present invention, in which Type I is characterized by a strong response to mixed ligands (green), with weaker responses to the individual ligands (gray), Type II is characterized by a weak response to mixed ligands (red) in comparison to individual ligands, and where the mixed response is intermediate (dark blue), two additional integration modes can be realized: the type III integration mode is characterized by decreased activity in response to removal of one ligand (dark blue to light blue), and a type IV integration mode occurs when removal of one of the ligands causes an increase in the response (dark blue to purple).
Figure 2H:
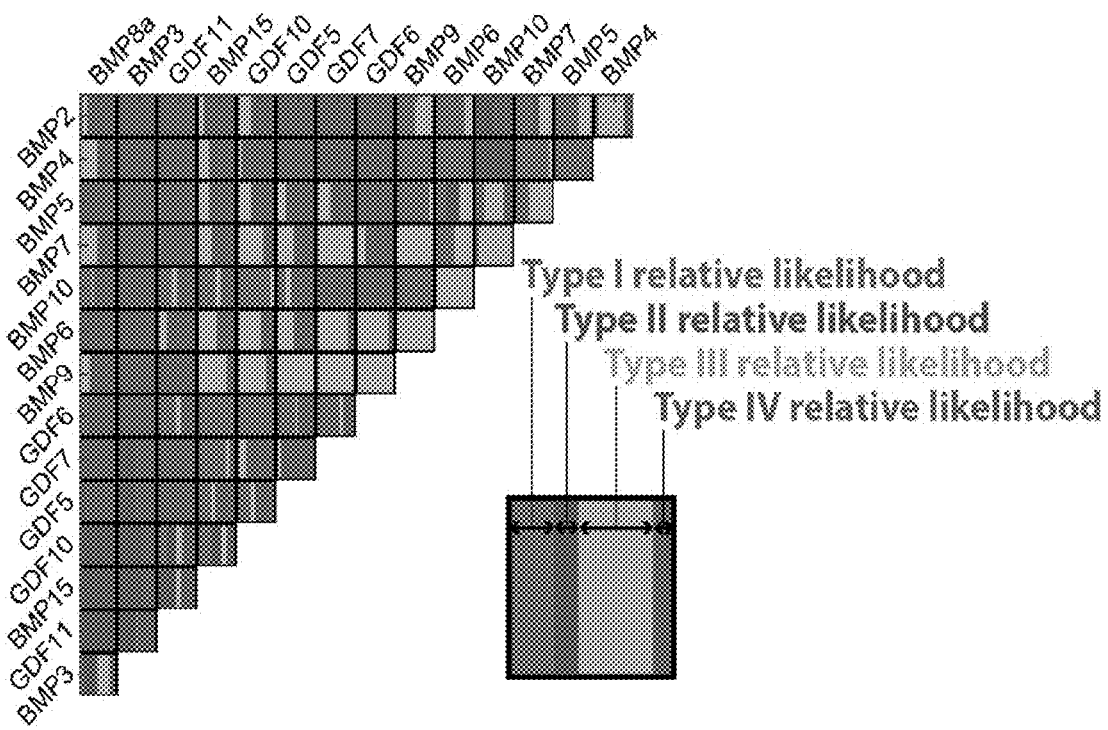
FIG. 2H is a ligand matrix using the low resolution ligand survey of FIG. 5A in which all pairs of ligands were classified across the 4 integration modes in FIG. 5G using the same representative colors, where for every pair, the likelihood of each mode was calculated as disclosed herein, and the corresponding square was colored by bands with widths proportional to the relative likelihood of each mode for which the appearance of multiple colors in the same square thus indicates uncertainty about the integration mode.

Many individual ligand pairs generated stronger or weaker responses than expected given their individual effects (FIGS. 3A, 2G, 2H). For example, BMP3 combined antagonistically with almost every other ligand. Furthermore, some individual ligands combined in qualitatively different ways with different ligands. For example, BMP7 and BMP4 each exhibited a mixture of antagonistic and synergistic interactions with other ligands. Overall, these results indicate that the effect of any given ligand on pathway activity can, in general, depend in complex ways on other ligands.

Figure 3C:
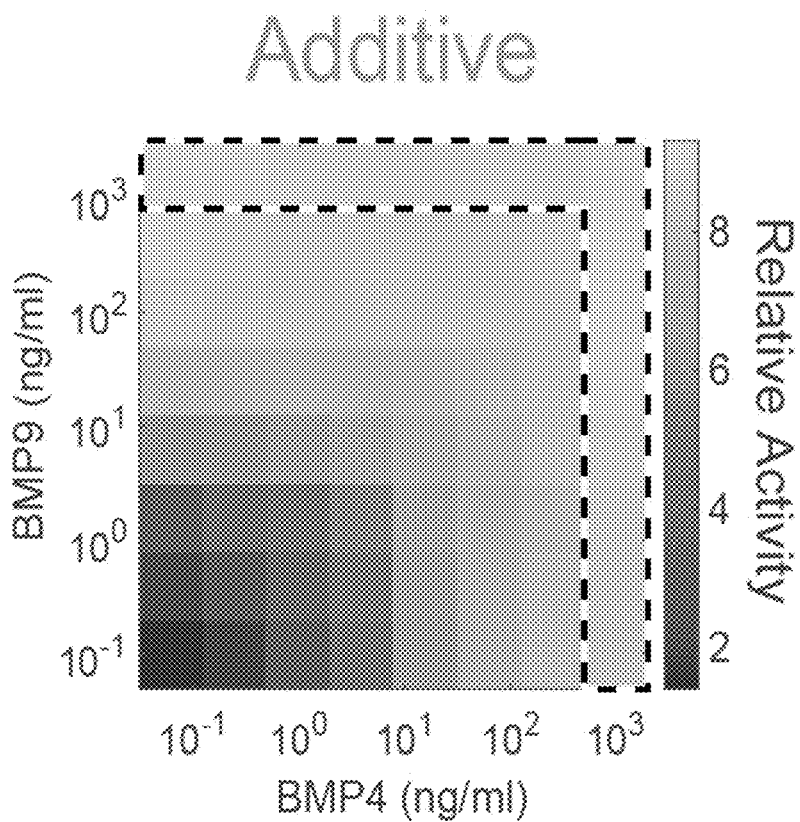
FIG. 3C is a ligand matrix of measurements of full input-output response profiles as measured by reporter H2B-Citrine expression in NMuMG BMP reporter cells for specific ligand pairs showing that BMP4 and BMP9 combine to increase pathway activity in an additive fashion, where the dashed outline in the matrix indicates a set of ligand concentrations varying from high concentration of one ligand (top left corner) to high concentration of the other ligand through intermediate states containing both ligands (e.g. top right), the bottom row and left column correspond to an absence of the indicated ligand with the relative activity of reporter H2B-Citrine expression shown in blue, green, orange, or yellow as indicated, according to embodiments of the present invention.
Figure 3D:
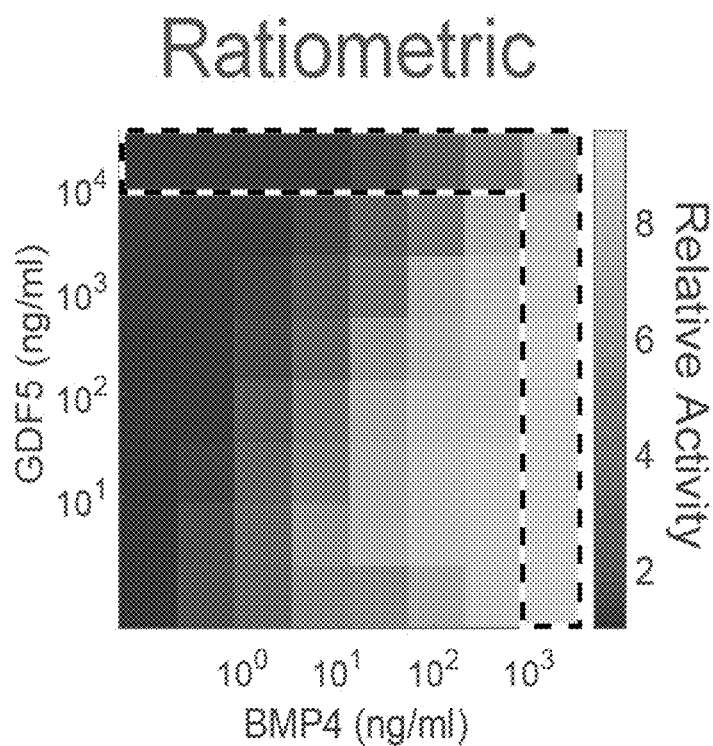
FIG. 3D is a ligand matrix of measurements of full input-output response profiles as measured by reporter H2B-Citrine expression in NMuMG BMP reporter cells for specific ligand pairs showing that BMP4 and GDF5 combine in a ratiometric manner, where the dashed outline in the matrix indicates a set of ligand concentrations varying from high concentration of one ligand (top left corner) to high concentration of the other ligand through intermediate states containing both ligands (e.g. top right), the bottom row and left column correspond to an absence of the indicated ligand with the relative activity of reporter H2B-Citrine expression shown in blue, green, orange, or yellow as indicated, according to embodiments of the present invention.
Figure 3E:
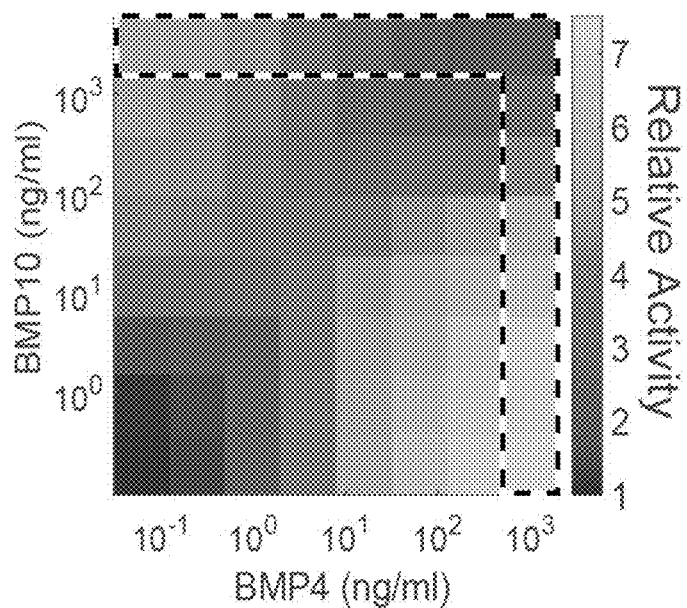
FIG. 3E is a ligand matrix of measurements of full input-output response profiles as measured by reporter H2B-Citrine expression in NMuMG BMP reporter cells for specific ligand pairs showing that the combination of BMP4 and BMP10 result in an 'imbalance detection' response, where the dashed outline in the matrix indicates a set of ligand concentrations varying from high concentration of one ligand (top left corner) to high concentration of the other ligand through intermediate states containing both ligands (e.g. top right), the bottom row and left column correspond to an absence of the indicated ligand with the relative activity of reporter H2B-Citrine expression shown in blue, green, orange, or yellow as indicated, according to embodiments of the present invention.
Figure 3F:
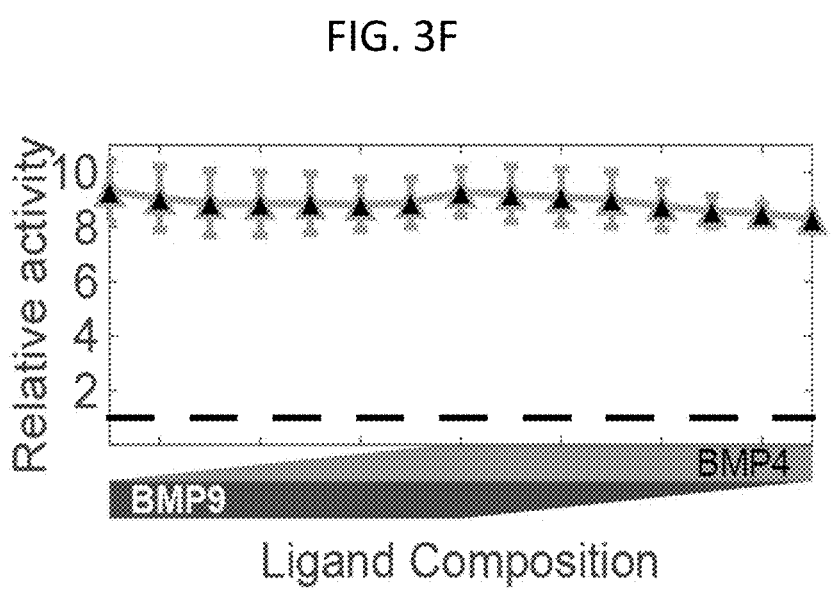
FIG. 3F is a graph of the relative activity responses as measured by reporter H2B-Citrine expression in NMuMG BMP reporter cells across a range of concentration ratios of BMP4 and BMP9 from 0:1 to 1:1 and 1:1 to 1:0 as indicated schematically on the x-axis with the logarithmic levels of each ligand across the range of ratios shown in green for BMP4 and blue for BMP9, and error bars indicate the standard deviation calculated from at least 3 experiments, according to embodiments of the present invention.
Figure 3G:
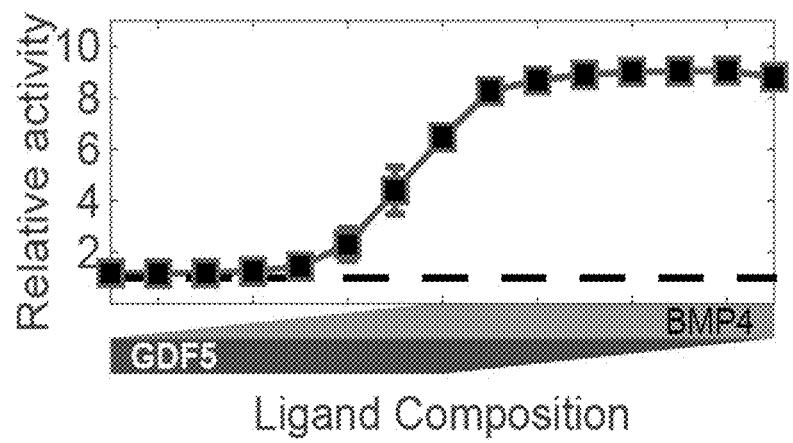
FIG. 3G is a graph of the relative activity responses as measured by reporter H2B-Citrine expression in NMuMG BMP reporter cells across a range of concentration ratios of BMP4 and GDF5 from 0:1 to 1:1 and 1:1 to 1:0 as indicated schematically on the x-axis with the logarithmic levels of each ligand across the range of ratios shown in green for BMP4 and blue for GDF5, and error bars indicate the standard deviation calculated from at least 3 experiments, according to embodiments of the present invention.

Higher resolution analysis reveals distinct multi-ligand response profiles. To gain a clearer view of multi-ligand responses, the diverse ways in which BMP4 (one of the best-studied BMP ligands) combines with other ligands was analyzed (FIG. 3B), particularly BMP9, GDF5, and BMP10 (FIGS. 3C-3E). To quantitatively characterize these interactions in a manner independent of the choice of base concentrations, we analyzed a 2-dimensional matrix of logarithmically spaced ligand concentrations (FIGS. 3C-3E). The broad (3 orders of magnitude) concentration range covers the full input dynamic range for each ligand pair in the NMuMG cell line, and overlaps ligand concentrations in circulating blood, as well as those used to induce BMP dependent responses in vitro.

Figure 4A:
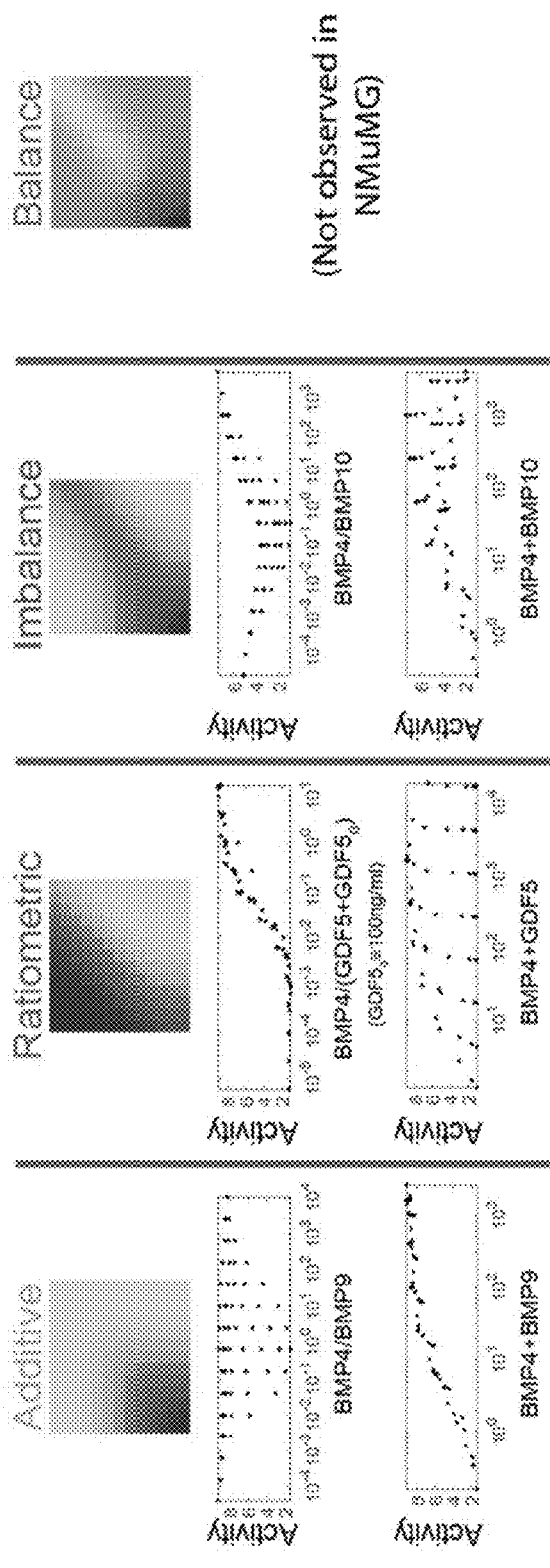
FIG. 4A shows the measured pathway activities of reporter H2B-Citrine expression in NMuMG BMP reporter cells plotted across all points in ligand matrices (with measured pathway relative activity shown in blue, green, orange, or yellow as indicated), adjusted ratio ligand concentration plots (upper plot), and summed ligand concentration plots (lower plot) for each indicated ligand pair (BMP4 and BMP9, BMP4 and GDF5, BMP4 and BMP10), where for most of the variation in activity in BMP4 and BMP9 can be explained by the sum of the two ligands, for BMP4 and GDF5 the data are better explained as a function of an adjusted ratio with the GDF5 concentration offset by a constant, representing the threshold above which the response becomes approximately ratiometric, and for BMP4 and BMP10, the response approximately follows a non-monotonic function of the ratio, according to embodiments of the present invention.
Figure 4B:
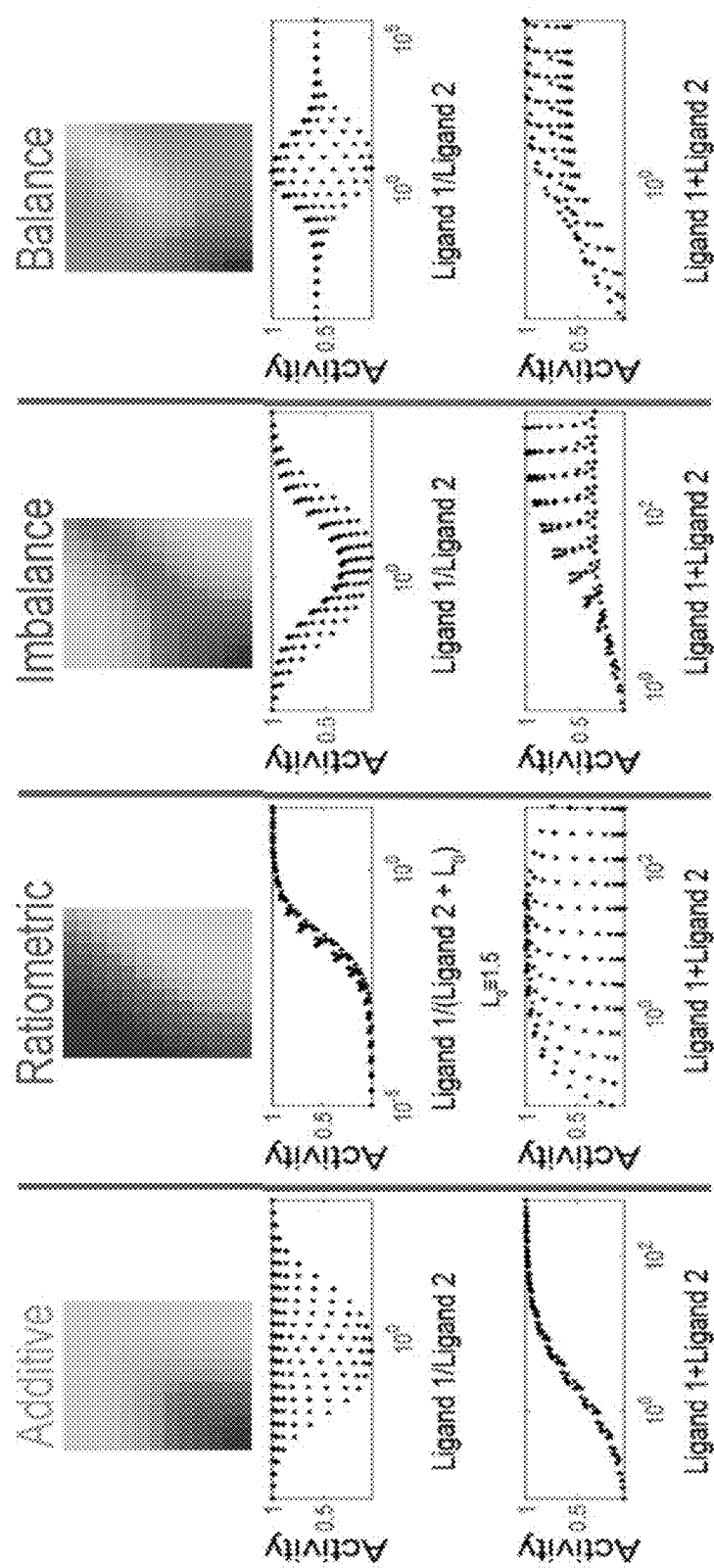
FIG. 4B shows similar activity plots as in FIG. 7A for archetypes generated in the model representing each type of activity (Additive, Ratiometric, Imbalance, and Balance), according to embodiments of the present invention.

Each of the three ligand pairs showed qualitatively distinct response profiles. BMP4 and BMP9 increased pathway activity both individually and in combination, exhibiting an additive response, with little dependence on ligand identity, as one would expect for ligands that function redundantly (FIGS. 3C, 4A). By contrast, GDF5 reduced activation by BMP4 in a dose-dependent fashion, such that pathway output approximated the ratio of the concentrations of the two ligands (FIGS. 3D, 4A). Similar ratiometric responses have been observed in other systems. Finally, and most intriguingly, BMP4 and BMP10 were potent activators individually, but each became inhibitory in the presence of high concentrations of the other ligand, resulting in a weaker response when both ligands were present (FIGS. 3E, 4A). Interestingly, in this mode, each ligand can play both activating and inhibitory roles. We termed this integration mode "imbalance detection" because it responds maximally to extreme ratios (imbalances) of the two ligand concentrations. We note that the same two-dimensional response profiles were observed using independently generated reporter cell lines, indicating that they do not reflect aspects of the chromatin configuration of a specific reporter integration site (FIG. 4C). The integration functions were also independent of the ligand supplier (FIG. 4D). Together, these results identify three distinct ways in which the BMP pathway can integrate ligand pairs.

Figure 3H:
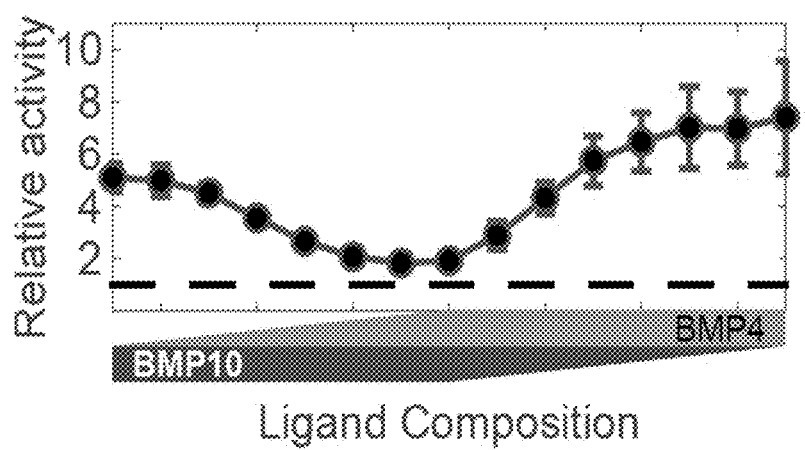
FIG. 3H is a graph of the relative activity responses and ligand ratio profile as measured by reporter H2B-Citrine expression in NMuMG BMP reporter cells across a range of concentration ratios of BMP4 and BMP10 from 0:1 to 1:1 and 1:1 to 1:0 as indicated schematically on the x-axis with the logarithmic levels of each ligand across the range of ratios shown in green for BMP4 and blue for BMP10, and error bars indicate the standard deviation calculated from at least 3 experiments, according to embodiments of the present invention.
Figure 5A:
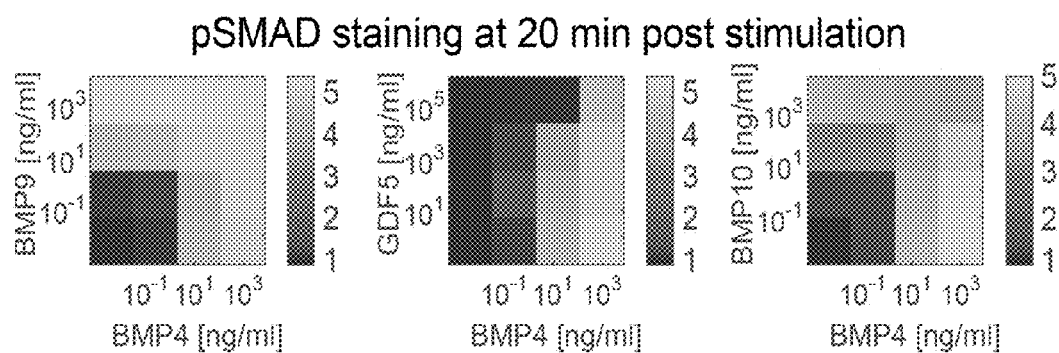
FIG. 5A shows ligand matrices representing the relative amount of phosphorylated SMAD (pSMAD) in response to the indicated ligand concentrations and combinations (left to right: BMP4 and BMP9, BMP4 and GDF5, and BMP4 and BMP10, as measured by phospho-SMAD immunostaining after 20 minutes after ligand addition, according to embodiments of the present invention.

Interestingly, these responses depend in distinct ways on the ligand composition, defined as the relative concentrations of the two ligands. To study this dependence, we plotted the response to varying relative ligand concentrations, at high total ligand concentration (FIGS. 3C-3E, dashed outline). These contours reveal that pathway activity is independent of ligand composition in the additive case (FIG. 3F), monotonically dependent in the ratiometric case (FIG. 5G), and non-monotonically dependent in the imbalance detection case, where pathway activity declines near a specific intermediate ligand ratio (FIG. 3H). Similar composition-dependence can be observed at lower ligand concentrations. The only exception is imbalance detection, which at ligand concentrations <10 ng/ml becomes indistinguishable from the additive response (FIG. 3C). These results indicate that the BMP pathway implements a diverse set of computations on multi-ligand inputs in NMuMG cells, and can be strongly controlled by ligand composition, as well as absolute ligand concentration.

Figure 4E:
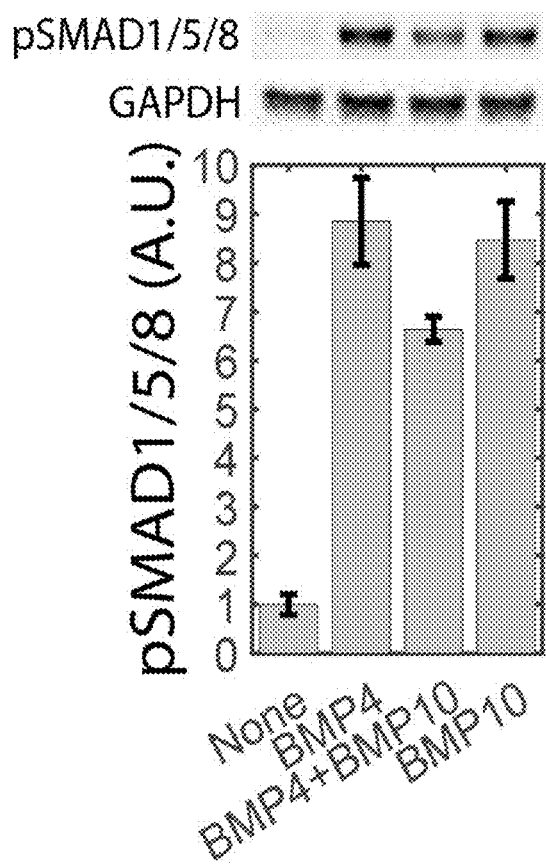
FIG. 4E shows an immunoblot and corresponding graph of the relative amounts of phosphorylated SMAD1/5/8 in cells exposed to a single ligand (BMP4 or BMP10), a ligand combination (BMP4 and BMP10), or no ligand (none), the results showing that BMP4 and BMP10 in combination exhibited imbalanced activity as indicated by the decrease in the amount of phosphorylated SMAD1/5/8, in which the results are normalized to the un-activated condition, and represent the mean and standard deviation of at least 3 independent repeats, according to embodiments of the present invention.
Figure 4F:
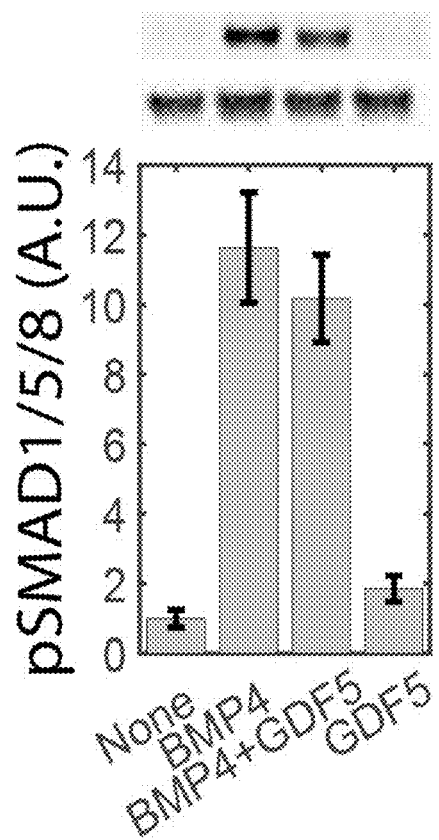
FIG. 4F shows an immunoblot and corresponding graph of the relative amounts of phosphorylated SMAD1/5/8 in cells exposed to a single ligand (BMP4 or GDF5), a ligand combination (BMP4 and GDF5), or no ligand (none), the results showing that BMP4 and GDF5 in combination exhibited a ratiometric response as indicated by the amount of phosphorylated SMAD1/5/8, in which the results are normalized to the un-activated condition, and represent the mean and standard deviation of at least 3 independent repeats, according to embodiments of the present invention.
Figure 4G:
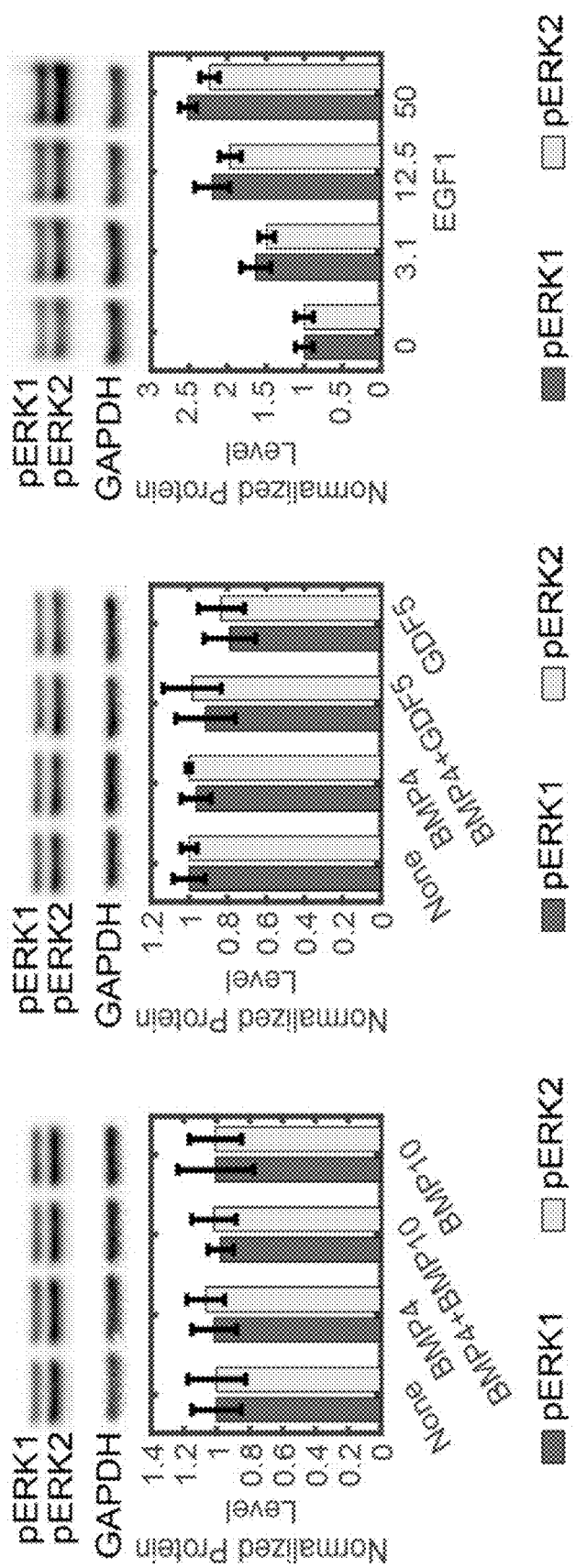
FIG. 4G shows immunoblots and corresponding graphs of the relative amounts of ERK phosphorylation by measuring the relative amounts of phosphorylation of ERK1 and ERK2 in response to BMP ligands where both ERK1 and ERK2 respond dose-dependently to epidermal growth factor 1 (EGF1) as shown on the right, and ERK1 and ERK2 show no change in phosphorylation in the presence of BMP4, BMP10, or GDF5 alone or in the indicated combinations as shown in the immunoblots and graphs on the left and middle, in which the results are normalized to the un-activated condition and represent the mean and standard deviation of at least 3 independent repeats, according to embodiments of the present invention.

Response profiles emerge rapidly and are stable. We next asked at what level and over what timescales these response profiles emerge. First, to access an earlier and more direct readout of pathway activity we measured SMAD1/5/8 phosphorylation at 20 minutes after stimulation with select ligand pairs, using immunostaining (FIG. 5A) and Western blots (FIGS. 4E-4F). Both measurements revealed qualitatively similar response profiles as the fluorescent reporter, indicating that computations emerge within 20 minutes, and can be observed at the level of SMAD phosphorylation. We note that ERK1/2, a non-canonical output did not respond to BMP stimulation in this cell context (FIG. 4G).

Figure 5B:
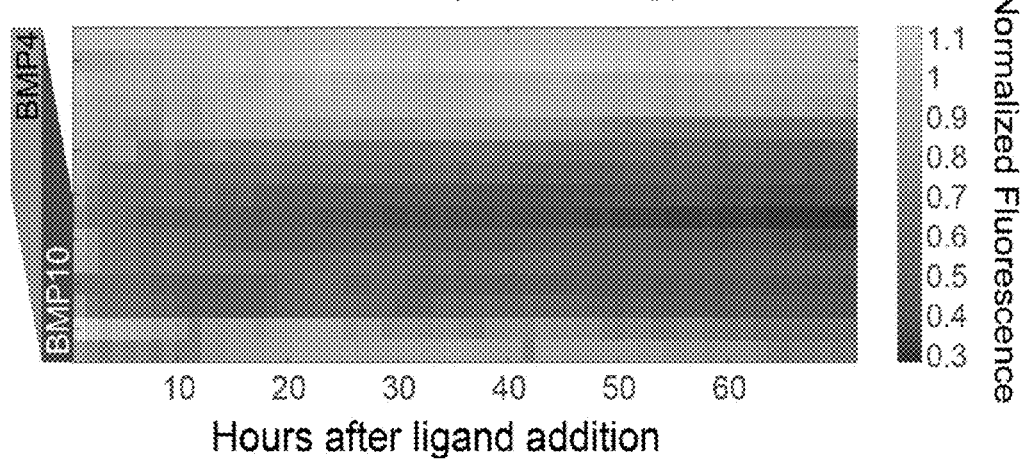
FIG. 5B is a ligand matrix representing the normalized fluorescence of reporter H2B-Citrine expression in NMuMG BMP reporter cells in response to mixtures of BMP4 and BMP10 plotted over 70 hours after addition of the ligands in which data is normalized at each time point to the response of cells treated with BMP4 only, according to embodiments of the present invention.
Figure 6A:
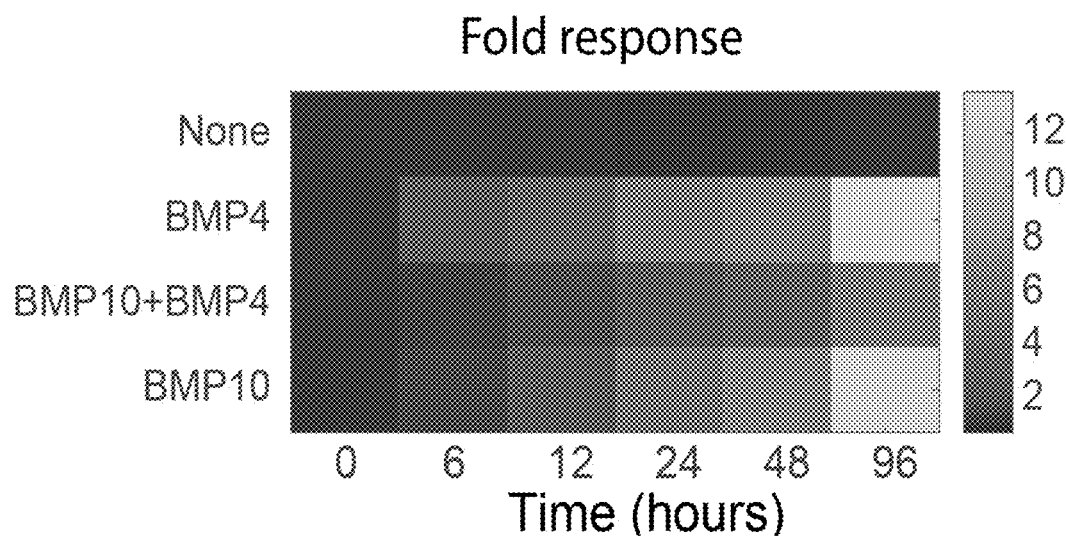
FIG. 6A is a ligand matrix representing the normalized fluorescence of reporter H2B-Citrine expression in NMuMG BMP reporter cells in response to mixtures of BMP4 and BMP10 with pathway responses (reporter H2B-Citrine expression) analyzed at different time points after ligand addition, with the results showing that while absolute fluorescence levels increased over time, the imbalance response is visible at all time points, from 6 to 96 hours after ligand stimulations, according to embodiments of the present invention.
Figure 6B:
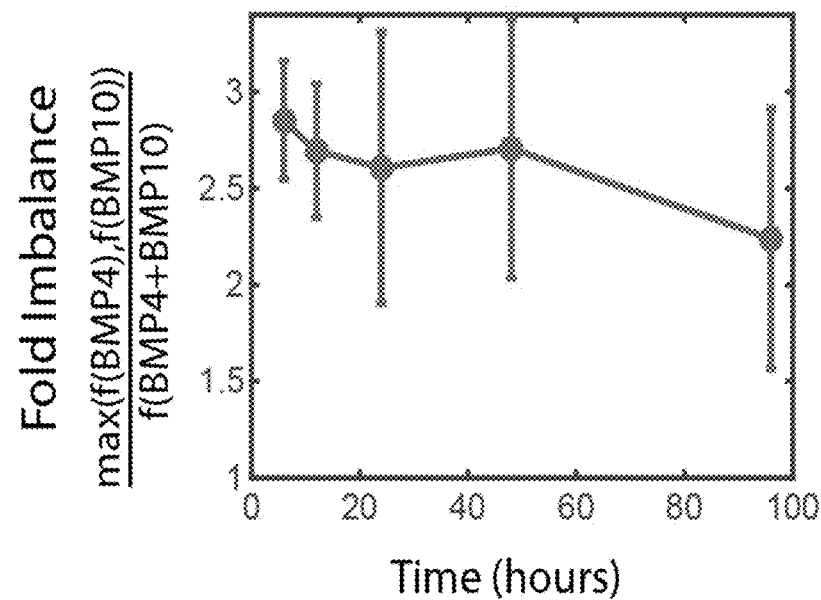
FIG. 6B is graph showing fold imbalance of BMP4 and BMP10 combination quantified as the ratio of the least active individual ligand to activation by both ligands, in which the measured activities were shown to be stable over the duration of the experiment, where error bars indicate the standard deviation calculated from 3 independent experiments, according to embodiments of the present invention.

Next, to better understand the dynamics of the BMP response, we used time-lapse imaging to track reporter expression over time in response to BMP4 and/or BMP10 (FIGS. 5B, 6A). The imbalance detection response could be identified by 6h and persisted for more than 96h. However, the relative level of activation caused by the combination of BMP4 and BMP10, compared to the individual ligands, remained constant (FIG. 6B), indicating that the imbalance detection response profile is stable over extended periods.

Figure 6C:
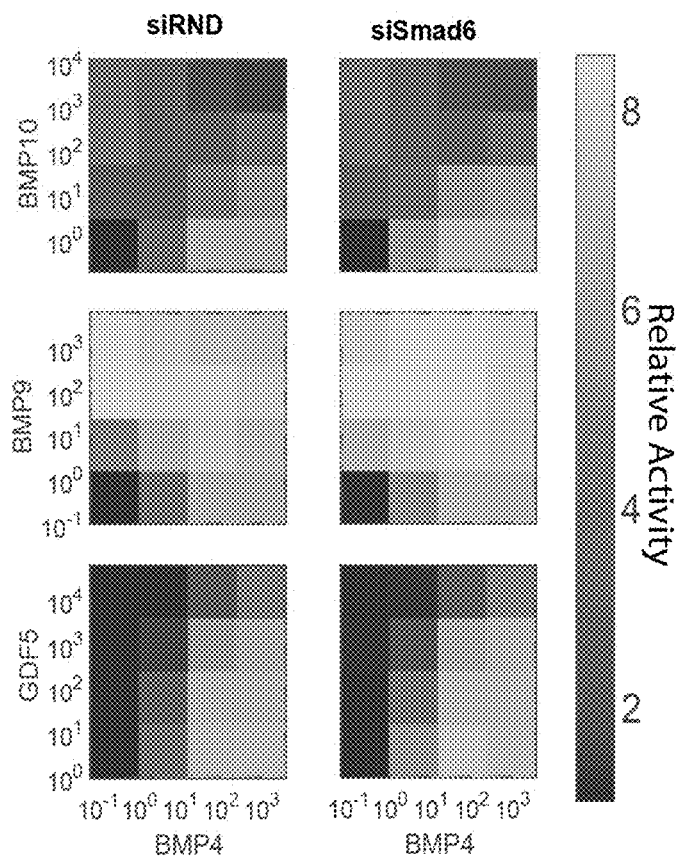
FIG. 6C is a ligand matrix representing the relative activity measured as fluorescence of reporter H2B-Citrine expression in NMuMG BMP reporter cells in response to mixtures of BMP4 with BMP10, BMP9, or GDF5 as indicated and treatment with siRNA against SMAD6 (siSmad6) or with a random sequence (siRND), the results showing that SMAD6 knockdown does not disrupt ligand integration, according to embodiments of the present invention.
Figure 6D:
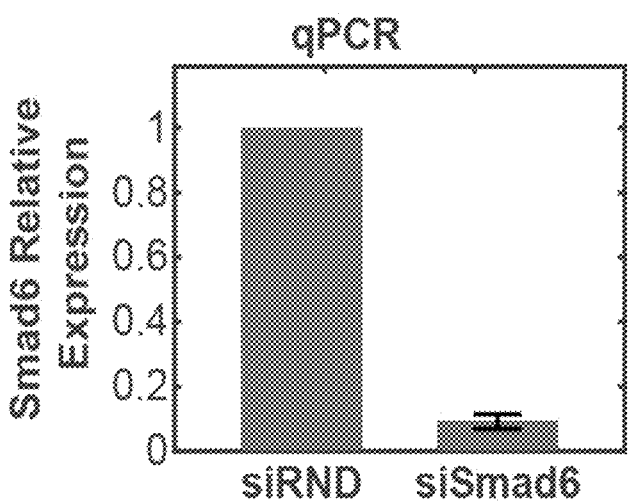
FIG. 6D is a graph of Smad6 relative expression quantified by qPCR showing that siRNA treatment reduced Smad6 transcript by approximately 90% where the error bars indicate standard deviation calculated from 3 independent experiments, according to embodiments of the present invention.
Figure 6E:
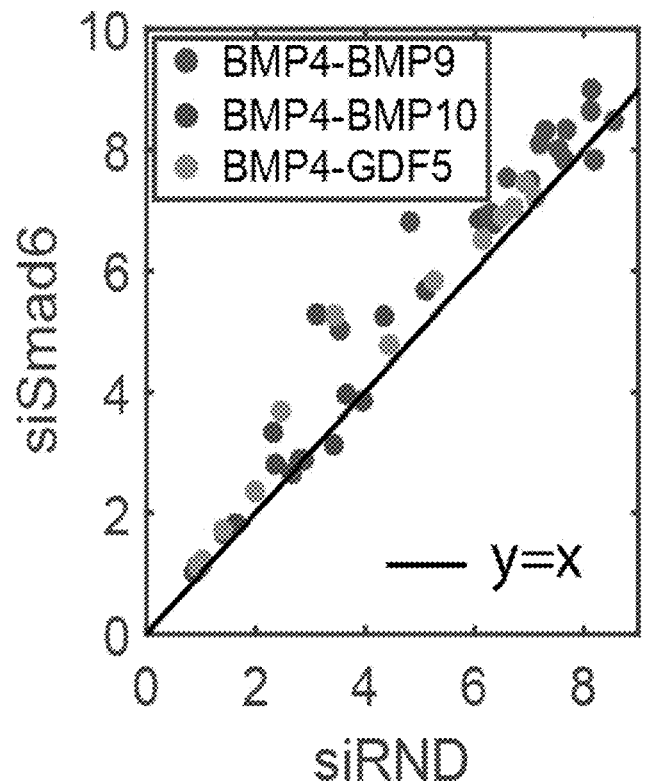
FIG. 6E is a graph plotting the results with siRNA for SMAD6 against those with a random siRNA sequence where each dot represents a single ligand combination where different colors (red, blue, or green) represent different ligand pairs as indicated and the black line represent the line y=x for reference, according to embodiments of the present invention.
Figure 6F:
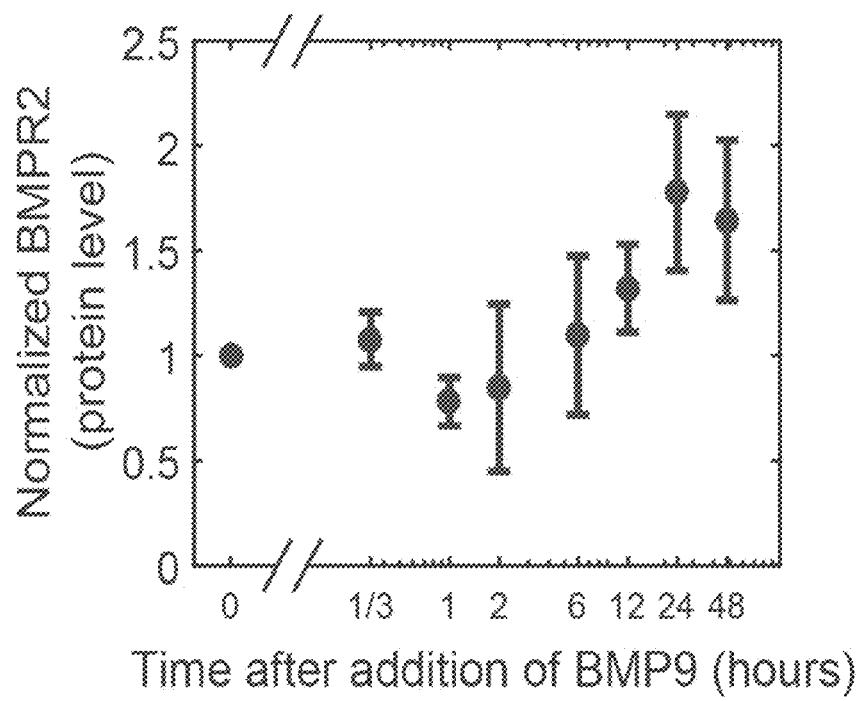
FIG. 6F is a graph of the normalized levels of BMPR2 protein (quantified by immunoblot analysis) over time (hours) after addition of BMP9 in NMuMG BMP reporter cells, where the BMPR2 protein levels were normalized by GAPDH protein levels, the fold change from t=0 was plotted, and the error bars represent standard deviation between 3 independent repeats, according to embodiments of the present invention.
Figure 6G:
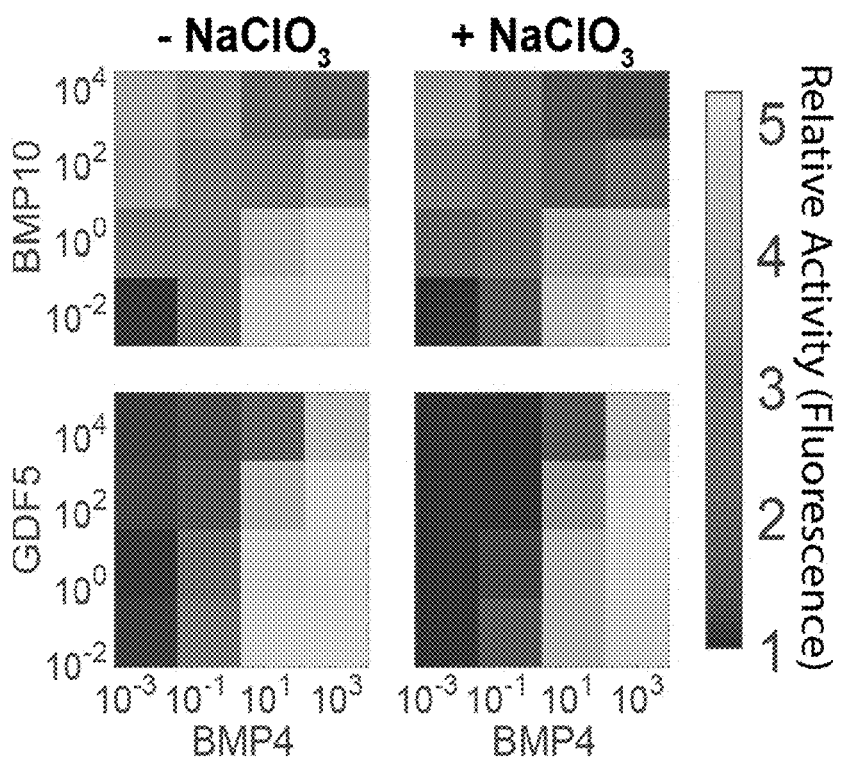
FIG. 6G is a ligand matrix representing the relative activity measured as fluorescence of reporter H2B-Citrine expression in NMuMG BMP reporter cells in response to mixtures of BMP4 with BMP10 or GDF5 as indicated in response to treatment with $NaClO_3$ to inhibit the biosynthesis of heparin sulfate proteoglycans (HSPGs), according to embodiments of the present invention.
Figure 6H:
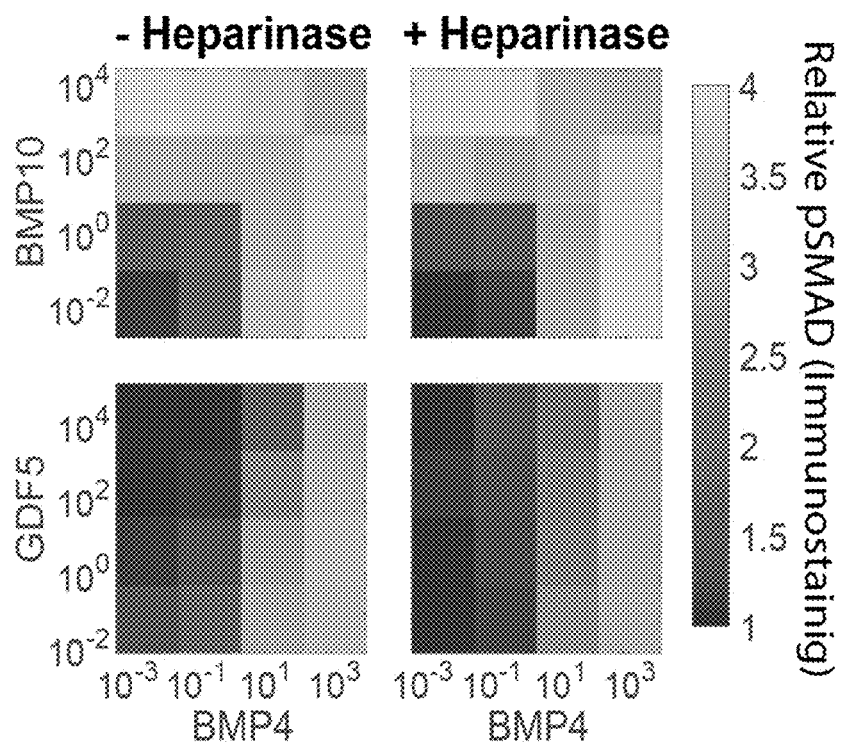
FIG. 6H is a ligand matrix representing the relative activity measured as fluorescence of reporter H2B-Citrine expression in NMuMG BMP reporter cells in response to mixtures of BMP4 with BMP10 or GDF5 as indicated in the presence or absence of heparinase to remove HSPG, according to embodiments of the present invention.
Figure 6I:
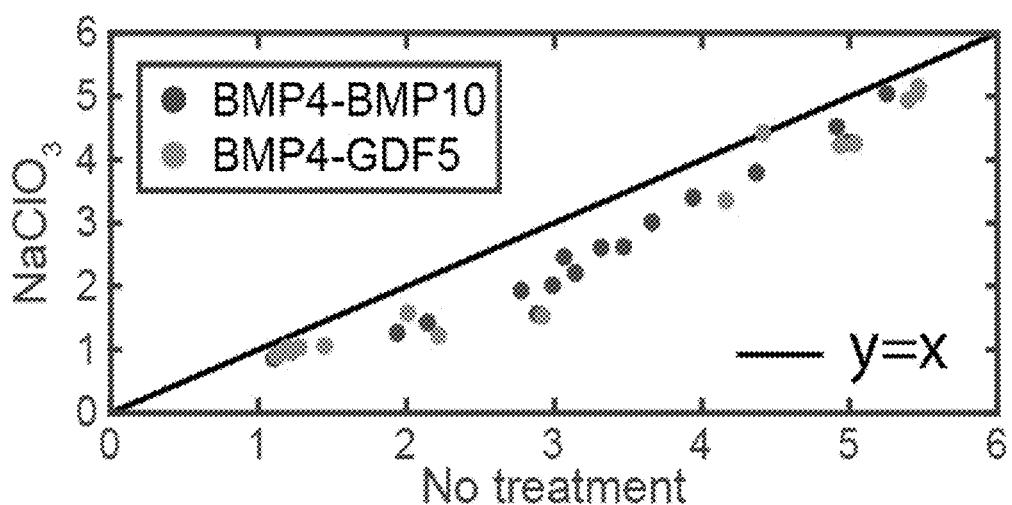
FIG. 6I is a graph plotting the results of the relative activity of the ligand pairs in FIG. 6G with NaClO3 treatment versus no treatment where each dot represents a ligand combination where different colors (blue or green) represent different ligand pairs as indicated and the black line represent the line y=x for reference showing a high level of correlation, according to embodiments of the present invention.
Figure 6J:
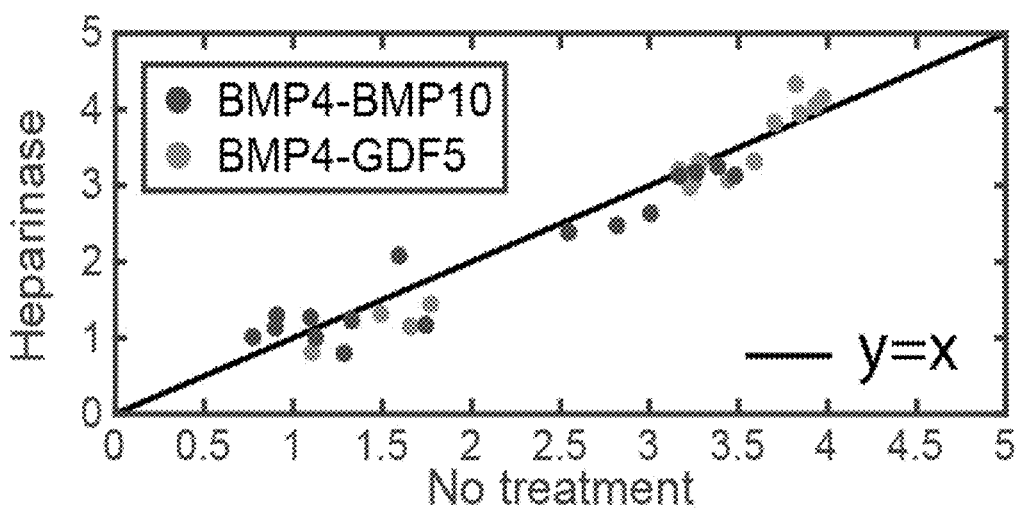
FIG. 6J is a graph plotting the results of the relative activity of the ligand pairs in FIG. 6H with heparinase treatment versus no treatment where each dot represents a ligand combination and the different colors (blue or green) represent different ligand pairs as indicated and the black line represent the line y=x for reference showing a high level of correlation, according to embodiments of the present invention.

Feedback loops and pathway modulators. We next asked whether known feedback loops in the BMP pathway were necessary for the observed computations. The negative pathway regulator SMAD6 is a downstream target of BMP (FIG. 2B). However, knock-down of SMAD6 did not qualitatively change the shape of the response profiles (FIGS. 6C-6E). Another reported feedback involves up-regulation of BMPR2 in response to BMP9 stimulation. Addition of 400 ng/ml BMP9 generated a 2-fold increase in BMPR2 expression (FIG. 6F). However, even this relatively modest effect appeared only at ~12 hours, consistent with the timescales of transcriptional regulation, and too late to explain the appearance of the computations at earlier time points. These results suggest that these feedback loops are not required for the computations observed here, although feedbacks may play other roles in enhancing the amplitude or dynamics of the pathway over longer timescales.

Figure 5C:
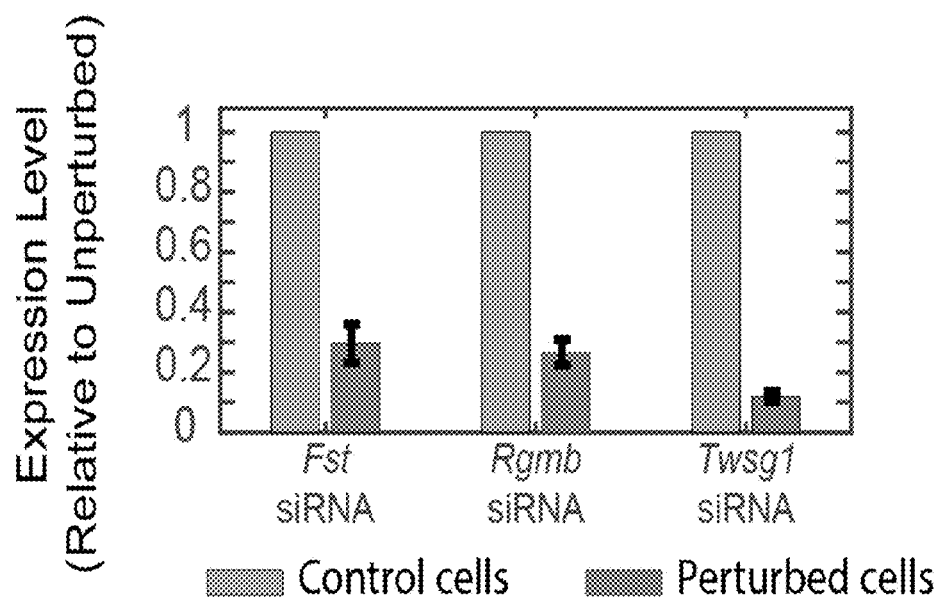
FIG. 5C is graph of the relative expression level of the indicated BMP modifier (Fst, RGMb, or Twsg1) in NMuMG cells in the presence Fst, RGMb, or Twsg1 siRNA, where the relative expression levels of Fst, RGMb and Twsg1 were measured using qPCR in cells transfected with the corresponding siRNA (blue) normalized to their levels in cells transfected with a random siRNA (grey), where error bars indicate standard deviation calculated from 3 independent experiments according to embodiments of the present invention.
Figure 5D:
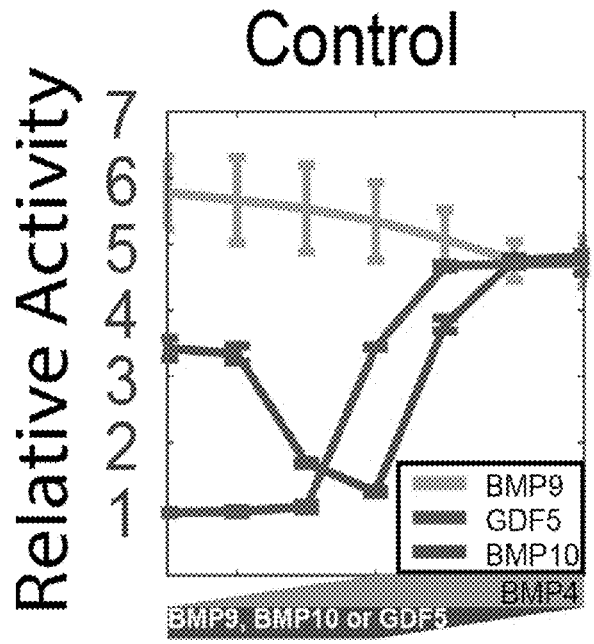
FIG. 5D is a graph of the relative activity of reporter H2B-Citrine expression in NMuMG BMP reporter cells treated with varying levels of BMP4 and the indicated ligand: BMP9 (blue), GDF5 (purple), or BMP10 (red) after depletion by random siRNA establishing control expression profile, where error bars indicate standard deviation calculated from 3 independent experiments according to embodiments of the present invention.
Figure 5E:
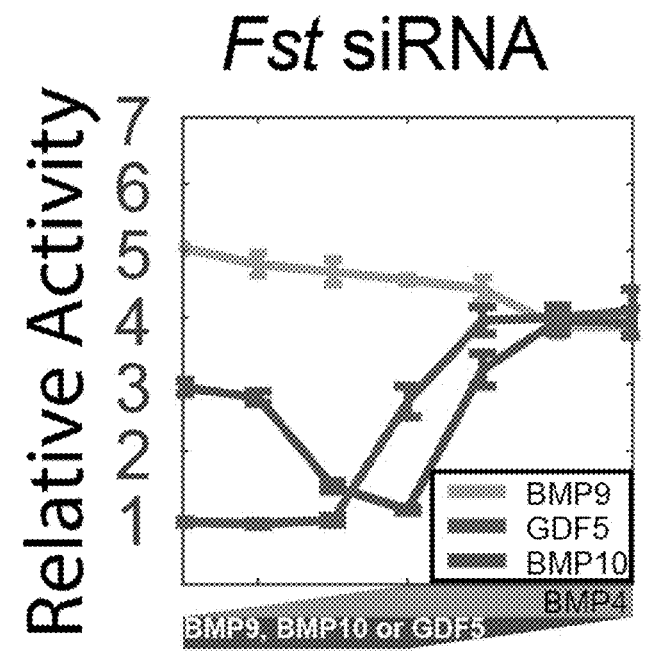
FIG. 5E is a graph of the relative activity of reporter H2B-Citrine expression in NMuMG BMP reporter cells treated with varying levels of BMP4 and the indicated ligand: BMP9 (blue), GDF5 (purple), or BMP10 (red) after depletion with Fst siRNA, where error bars indicate standard deviation calculated from 3 independent experiments according to embodiments of the present invention.
Figure 5F:
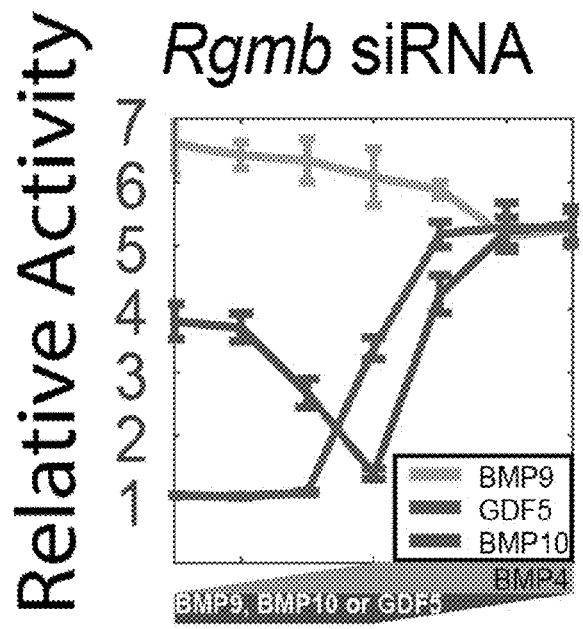
FIG. 5F is a graph of the relative activity of reporter H2B-Citrine expression in NMuMG BMP reporter cells treated with varying levels of BMP4 and the indicated ligand: BMP9 (blue), GDF5 (purple), or BMP10 (red) after depletion with RGMb siRNA, where error bars indicate standard deviation calculated from 3 independent experiments according to embodiments of the present invention.
Figure 5G:
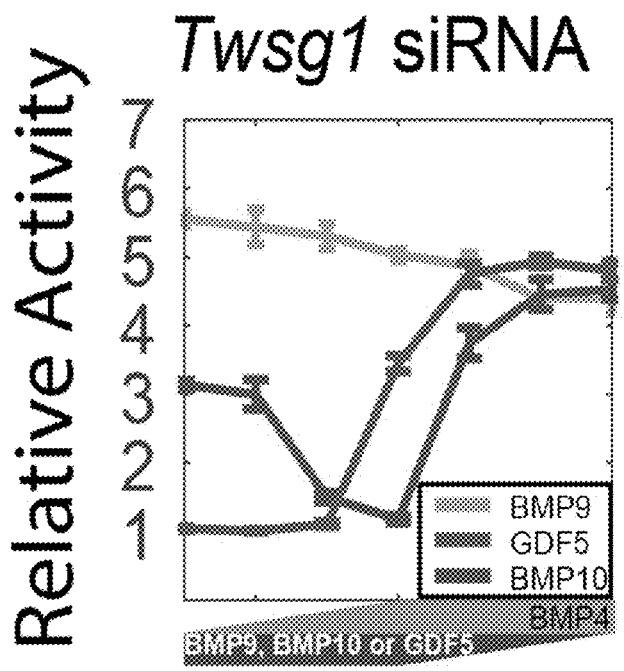
FIG. 5G is a graph of the relative activity of reporter H2B-Citrine expression in NMuMG BMP reporter cells treated with varying levels of BMP4 and the indicated ligand: BMP9 (blue), GDF5 (purple), or BMP10 (red) after depletion with Twsg1 siRNA, according to embodiments of the present invention.

The BMP pathway utilizes many secreted and surface-bound modulators to shape the spatial distribution of available ligands. To test whether these factors play a role in ligand integration, we first determined which ones were expressed in the NMuMG cell line. Individually depleting each of these factors using siRNAs (FIG. 5C) did not affect the type of response profile generated by BMP4 in combination with BMP9, BMP10, or GDF5 (FIGS. 5D-5G). In addition, BMPs could interact more generally with heparin sulfate proteoglycans (HSPGs). Enzymatically perturbing HSPGs with heparinase or inhibiting their biosynthesis with CaClO3 showed minimal effects on the response of the pathway to BMP combinations (FIGS. 6G-6J). Together, these results suggest that, while these modulators play key roles in other aspects of BMP signaling, they are not required for the observed multi-ligand computations. These results are, however, consistent with computations emerging directly from receptor-ligand interactions.

Figures 7A, 7B:
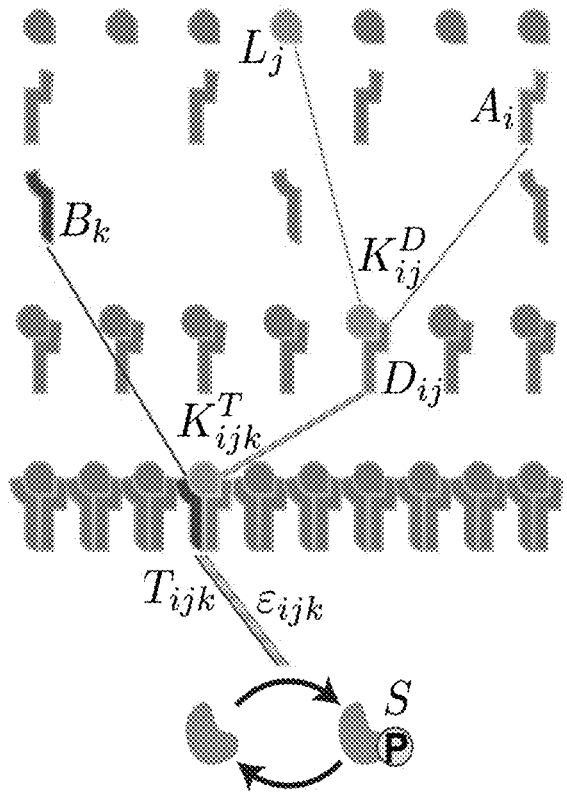
FIG. 7A is schematic representation of ligands (top row, green), type A receptors (second row, red), type B receptors (third row, purple), intermediate complexes (fourth row), and signaling complexes (fifth row), in which only a subset of possible complexes is shown for simplicity, colored lines highlight interactions involved in the formation of a single signaling complex, with corresponding parameters indicated, according to embodiments of the present disclosure.
FIG. 7B show reactions (left) and corresponding steady-state equations (right) for the model shown in FIG. 7A, according to embodiments of the present disclosure.

A minimal model of promiscuous receptor-ligand interactions. To understand how receptor-ligand interactions could generate the observed complex ligand integration modes, we constructed a simplified mathematical model that incorporates two key features of the BMP pathway: the bipartite structure of active BMP receptors complexes (i.e. the requirement for both type I and type II receptors), and promiscuous, competitive receptor-ligand interactions (FIGS. 7A, 7B). The model considers a set of ligands, denoted $L_j$, and two types of receptors, denoted $A_i$ and $B_k$, analogous to the BMP type I and type II receptor subunits, respectively. Each ligand can bind with affinity $K_{ij}^D$ to an A-type receptor to form a dimeric complex $D_{ij}$, which in turn can bind a B-type receptor with affinity $K_{ijk}^T$ to form an active trimeric complex, $T_{ijk}$. Because the affinity parameters can differ for each ligand-receptor combination, this model allows both receptor preferences as well as promiscuous interactions. Each trimeric complex phosphorylates SMAD proteins at a distinct rate, or activity, denoted $\varepsilon_{ijk}$, to produce an overall output signal S at steady state. The model considers the experimental regime of large extracellular volume, but similar conclusions occur at finite volume. Here, we focus on the minimal case of 2 ligands, 2 A-type receptors and 2 B-type receptors, whose behavior can be specified by 16 independent biochemical parameters and 4 receptor expression levels, and which is sufficient to explain the present experimental observations.

This simplified model omits several known features of the BMP pathway, such as variations in the sequence of binding reactions, the hexameric nature of actual signaling complexes, as well as the roles of other BMP regulatory factors. These features likely play important biological roles, e.g. in controlling the amplitude and spatio-temporal dynamics of signaling, that should be considered in models of specific biological processes. However, incorporation of these additional features in the model does not change the types of input-output computations examined here.

Figure 8A:
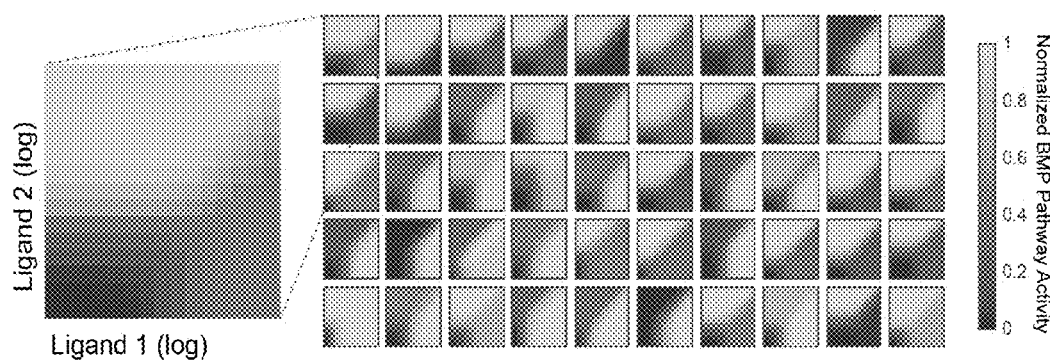
FIG. 8A shows a series of ligand matrices using the mathematical model where different biochemical parameter sets generate a range of 2-ligand integration functions in which the steady-state response for 50 randomly selected parameter sets (grid of heat maps) was plotted in which a broad range of behaviors and the general dependence on ratiometric features at high total ligand concentrations is noted and reflected by the diagonal contours, according to embodiments of the present disclosure.
Figure 8B:
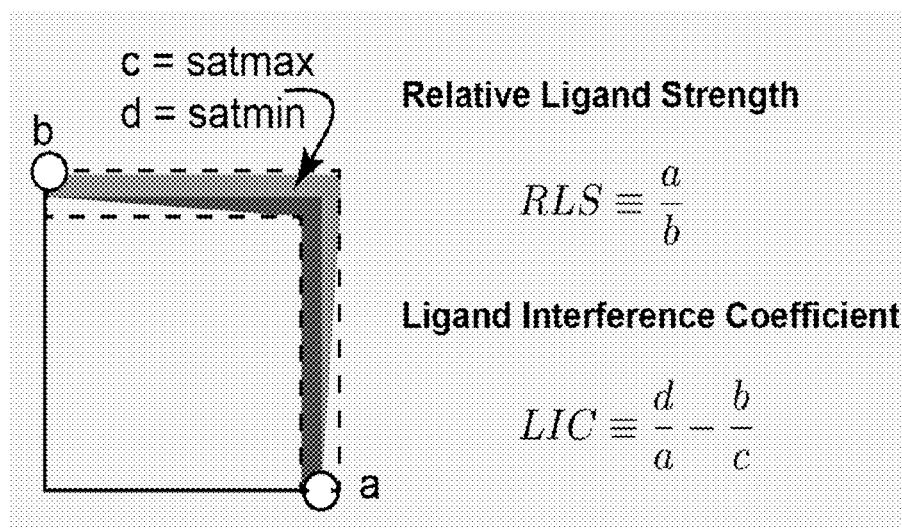
FIG. 8B shows analysis of 2 ligand response profiles parameterized by Relative Ligand Strength (RLS) and Ligand Interference Coefficient (LIC) in which these coefficients are determined by four activity levels that can be extracted from the high total ligand regime: the activity generated by the weaker (a) and stronger (b) ligands individually, as well as the maximal (c) and minimal (d) activity over the entire high ligand region, denoted by satmax and satmin, respectively, according to embodiments of the present disclosure.
Figure 8C:
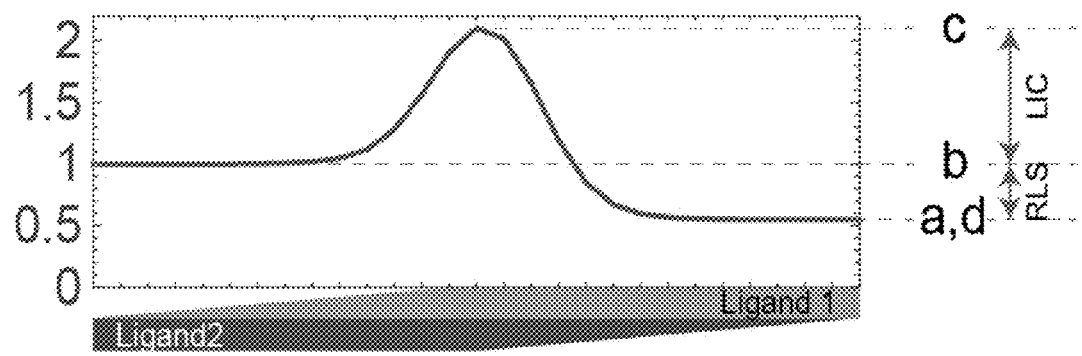
FIG. 8C shows determination of RLS and LIC for imbalance, according to embodiments of the present disclosure.
Figure 8D:
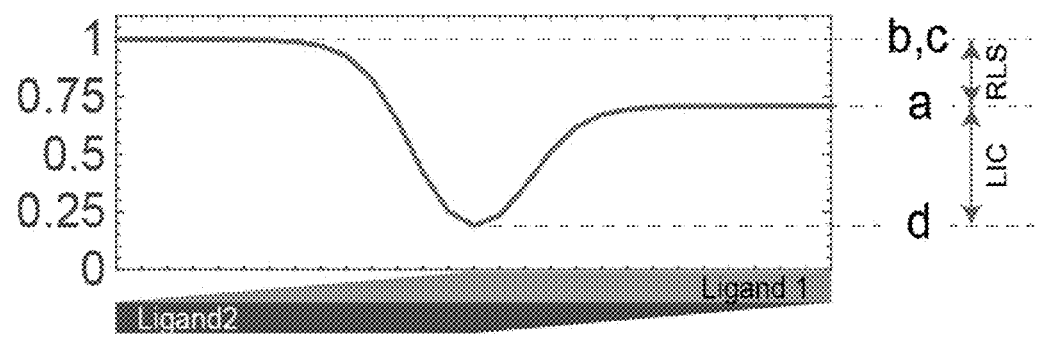
FIG. 8D shows determination of RLS and LIC for balance, according to embodiments of the present disclosure.

Archetypal functions define the range of response profiles. To explore the range of integration modes produced by the model, we computed the input-output behavior of the system for 100,000 random parameter sets (FIG. 8A). The model produced a repertoire of computational response profiles, which included additive, ratiometric, and imbalance detection. To more quantitatively characterize this repertoire, we defined two features that together capture key aspects of the shape of the response profiles (FIGS. 8B-8D). First, we defined the Relative Ligand Strength (RLS) to quantify the asymmetry in pathway activity generated by the ligands individually. The RLS is defined as the ratio of pathway activity produced by the weaker ligand to that produced by the stronger ligand. Second, we defined the Ligand Interference Coefficient (LIC) to quantify the degree to which the two ligands positively or negatively synergize (see Supplementary Text). The LIC is defined by the deviation of pathway activity in mixed ligand environments beyond the range of the responses in single ligand environments.

Figure 7C:
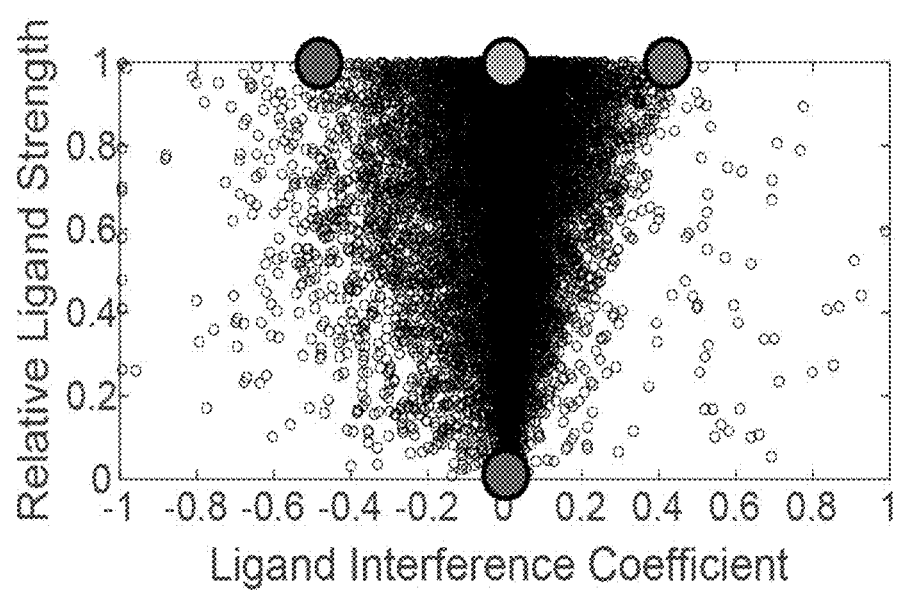
FIG. 7C is graph using 2 ligands and 2 variants of each receptor type, plotting the relative ligand strength versus the ligand interference coefficient (the type and strength of interference between the 2 ligands with antagonism have negative values and synergy having positive values, the plot showing that the model produces a variety of different signal processing behaviors, where each point represents the behavior of one randomly chosen parameter set, and most parameter sets generate computations that fall within a triangular region, while some show more extreme phenotypes, according to embodiments of the present disclosure.
Figure 7E:
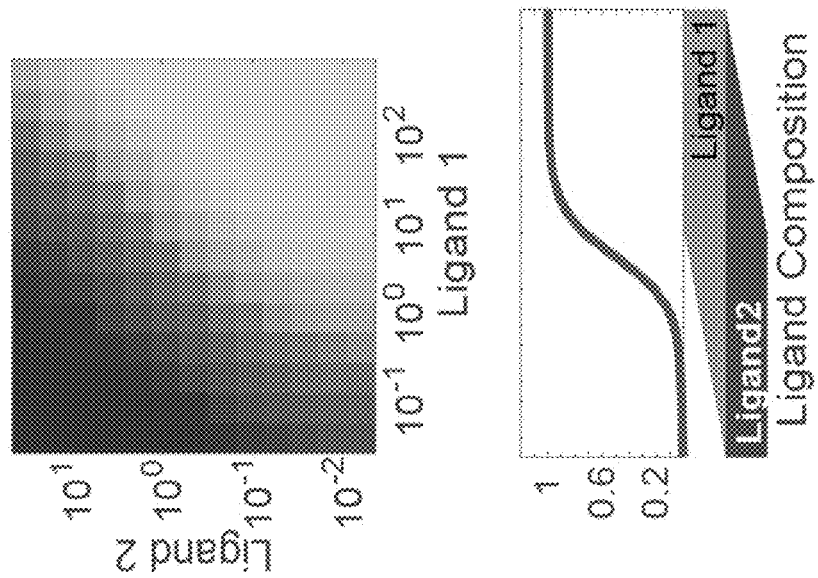
FIG. 7E shows a representative ligand matrix characterizing ligand-dependent response with each of Ligand 1 and Ligand 2 alone and in combination as a result of pathway activity as a function of ligand ratio in which Ligand 1 and Ligand 2 show a Ratiometric type response in combination, according to embodiments of the present disclosure.
Figure 7D:
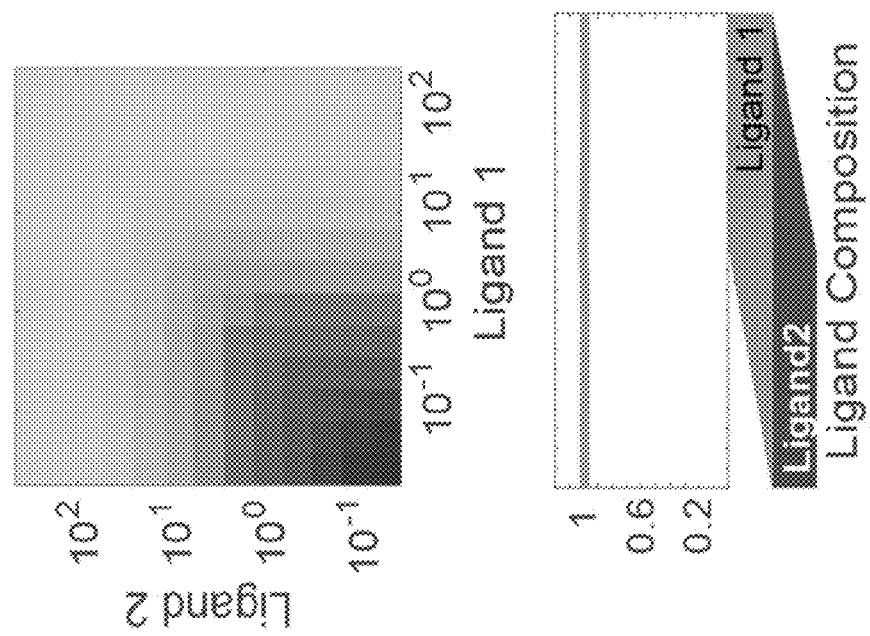
FIG. 7D shows a representative ligand matrix characterizing ligand-dependent response with each of Ligand 1 and Ligand 2 alone and in combination as a result of pathway activity as a function of ligand ratio in which Ligand 1 and Ligand 2 show an Additive type response in combination, according to embodiments of the present disclosure.
Figure 7F:
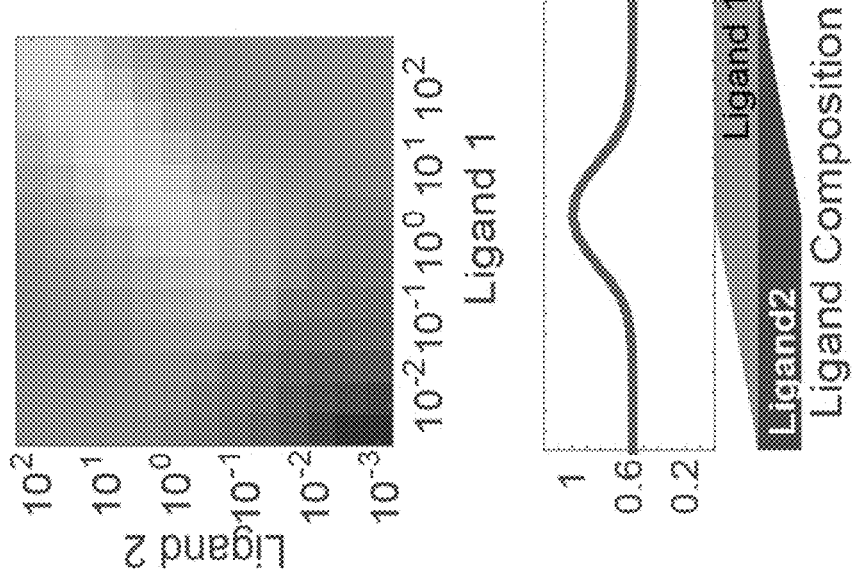
FIG. 7F shows a representative ligand matrix characterizing ligand-dependent response with each of Ligand 1 and Ligand 2 alone and in combination as a result of pathway activity as a function of ligand ratio in which Ligand 1 and Ligand 2 show an Imbalance type response in combination, according to embodiments of the present disclosure.
Figure 8E:
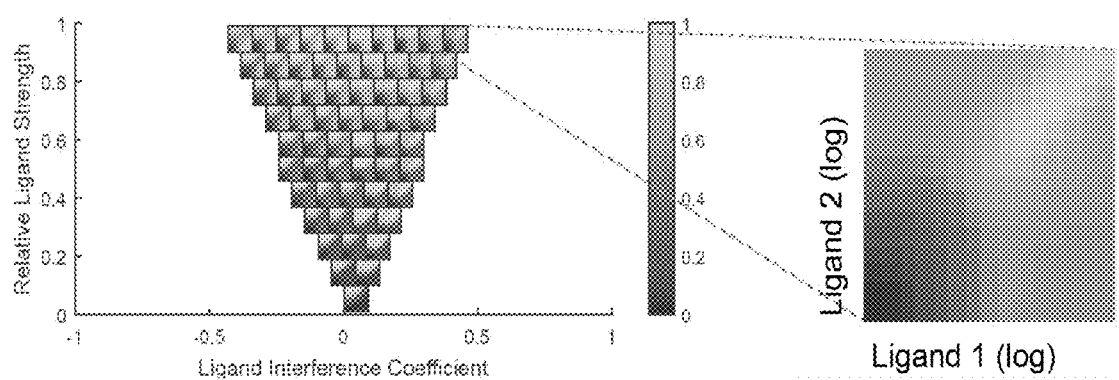
FIG. 8E graphically shows for each (LIC, RLS) coordinate pair the computed mean response functions for 5 biochemical parameter sets generating phenotypic parameters close to the indicated (LIC, RLS) point (location of heatmap) with inset zooms in one specific (RLS, LIC) point, according to embodiments of the present disclosure.
Figure 9A:
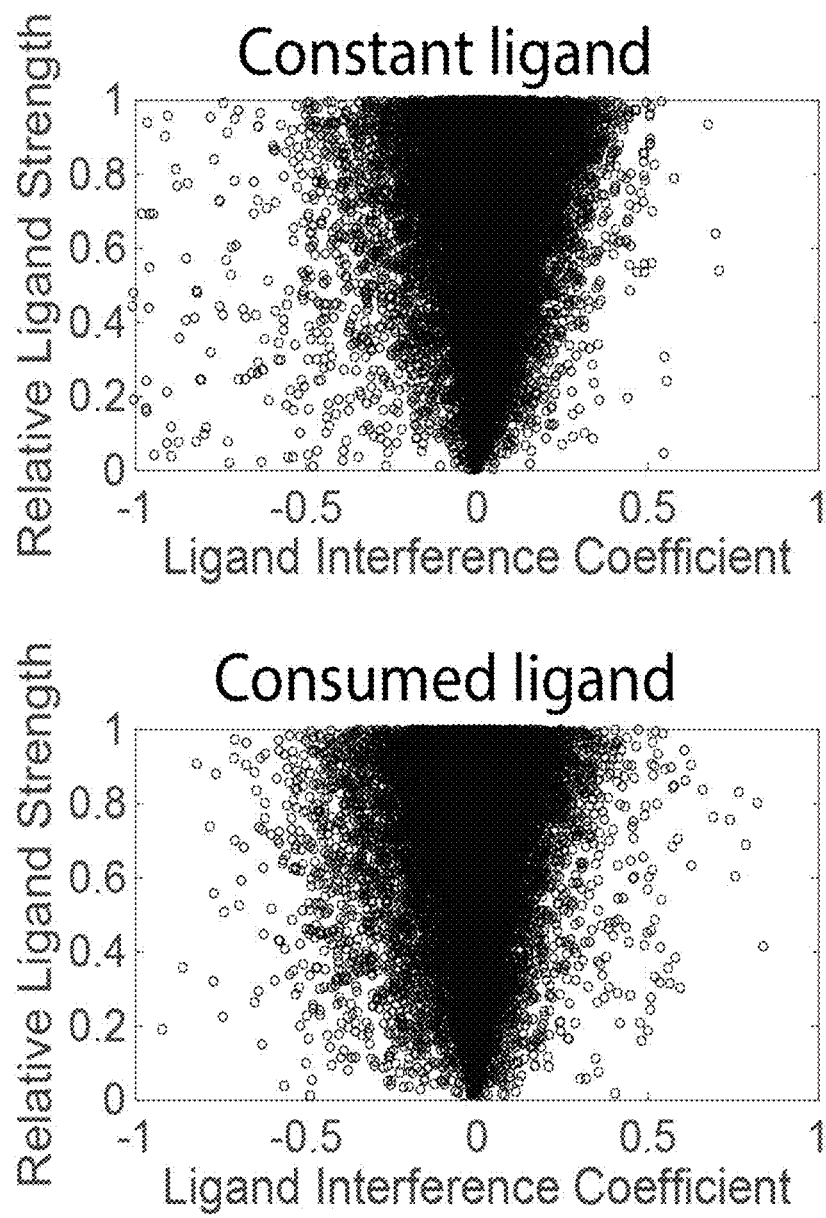
FIG. 9A is dot plot of 100,000 simulations performed on randomly chosen parameter sets with (lower) and without (upper) allowing for consumption of ligands by cells, in which the calculated ligand interference coefficient (LIC) and relative ligand strength (RLS) show similar distributions and produce all computations in both cases, according to embodiments of the present disclosure.
Figure 9B:
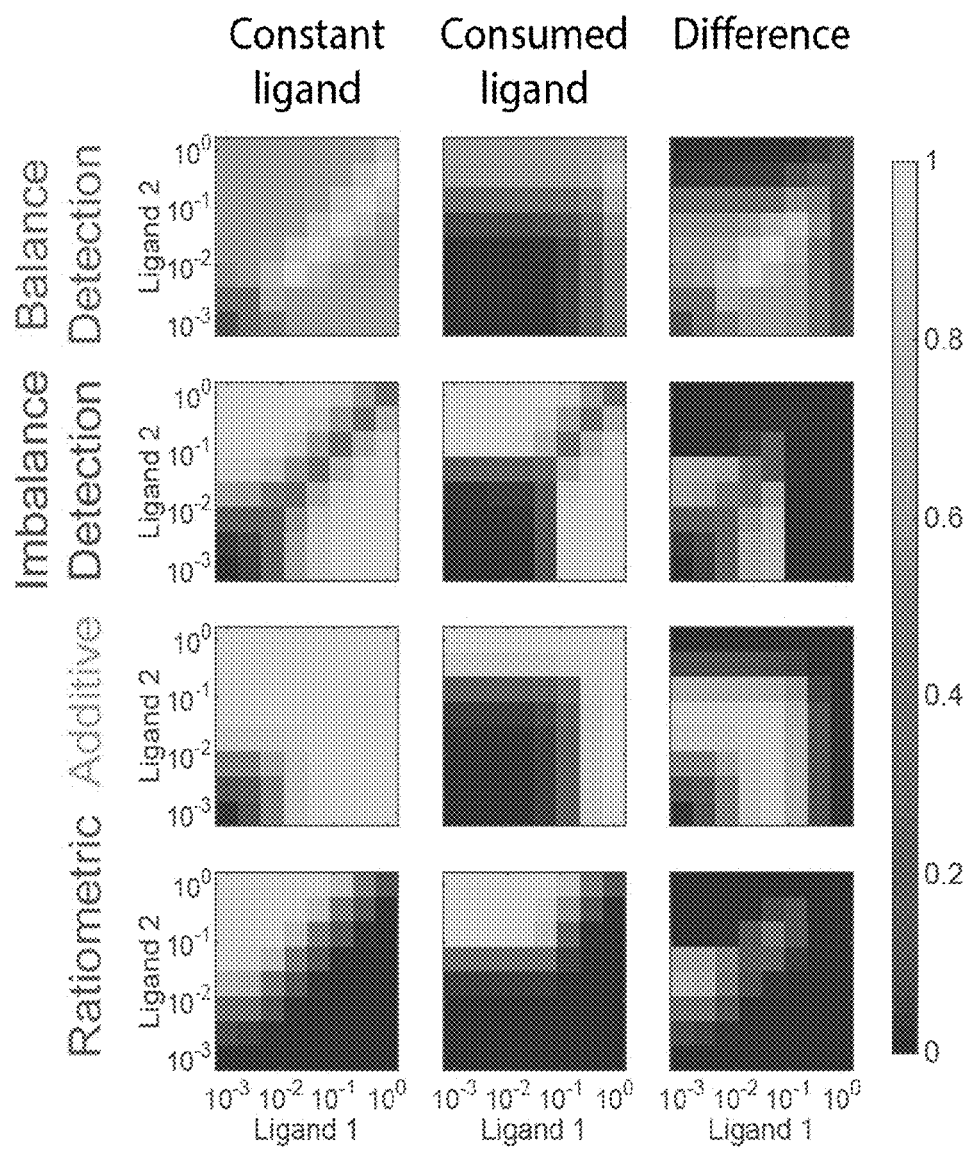
FIG. 9B shows full 2D input-output ligand matrices plotted for parameter sets corresponding to the 4 archetypes in which the models are with (center) and without (left) ligand consumption with the difference (right column) between the two models (constant ligand, left, vs. consumed ligand, middle) demonstrating that the effects of ligand consumption are most significant at intermediate ligand levels, giving rise to a sharper signal response, according to embodiments of the present disclosure.

When plotted in this two-parameter phenotypic space, the simulated systems occupied a continuous region that loosely conformed to an inverted triangle (FIGS. 7C, 8E). Two vertices of the triangle strikingly resembled the ratiometric and imbalance detection functions observed experimentally (FIGS. 3C-3E and FIGS. 7D-7F). The third vertex, occurring for ligands with a relative ligand strength of 1 and a positive ligand interference coefficient, represented a new predicted behavior, which we termed 'balance detection' because it shows a maximal response when both ligands are present at a specific ratio. All other functions, including the additive interaction at RLS=1, LIC=0 (top middle, FIG. 7C), interpolated between these three archetypal functions (FIG. 8E). The archetypal functions identified here differ from standard Boolean logic, since they depend asymptotically on ligand ratios, rather than absolute concentrations. These conclusions remain qualitatively similar if one considers a finite extracellular volume FIGS. 9A, 9B). This analysis provides an intuitive way to understand the distribution of response profiles.

Figure 9C:
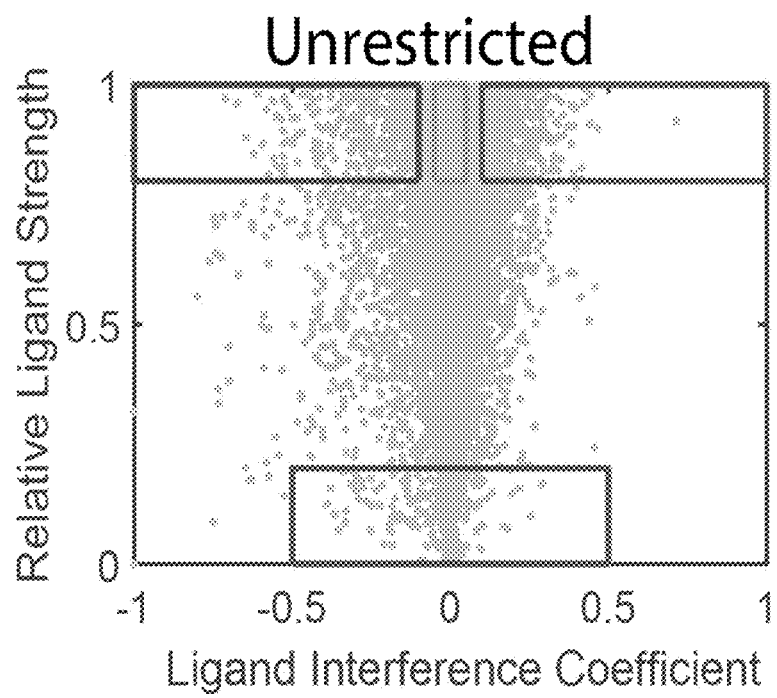
FIG. 9C is a dot plot graph using 100,000 parameter sets randomly selected either from the complete theoretically available parameter space, assuming a uniform distribution for the dimensional reduced parameters based on previously measured valued for BMP affinities, with specific regions in the neighborhood of each archetype boxed as indicated with the colored boxes, according to embodiments of the present disclosure.
Figure 9D:
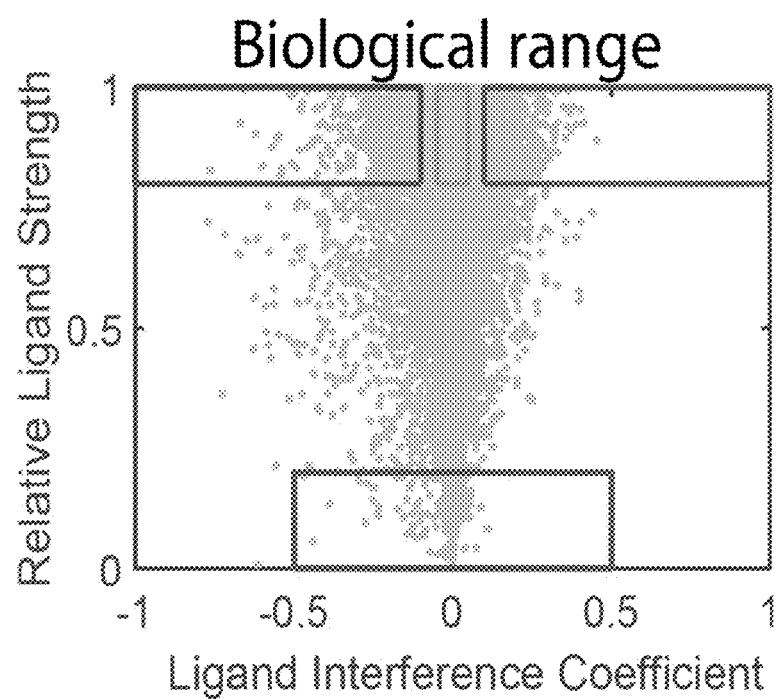
FIG. 9D is a dot plot graph using 100,000 parameter sets randomly selected either from the complete theoretically available parameter space, restricted to a biologically relevant range based on previously measured valued for BMP affinities, with specific regions in the neighborhood of each archetype boxed as indicated with the colored boxes, according to embodiments of the present disclosure.
Figure 9E:
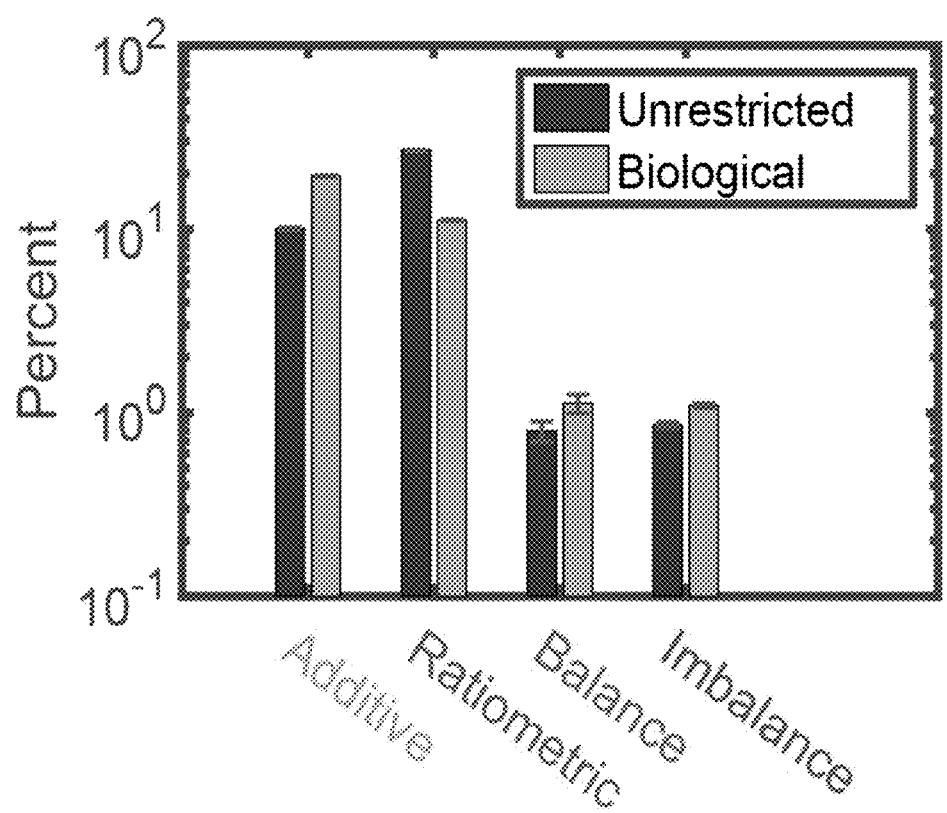
FIG. 9E is a graph showing the percent of parameter sets giving rise to each response type is shown for the unrestricted parameter selection (black) and for parameters restricted to the biologically relevant range (grey), in which the uncertainty was estimated by calculating a standard deviation between 10,000 bootstrapped samples of size 100,000, according to embodiments of the present disclosure.

To better characterize the distribution of response profiles, we quantified the percentage of occurrences of each response type in regions around each of the archetypal responses (FIGS. 9C, 9D). All archetypal behaviors occurred, whether parameters were chosen from a full range of values, or restricted to a biologically relevant range (Supplementary). However, parameters in the biological range showed an enrichment for the additive, balance detection, and imbalance detection response profiles (FIG. 9E). We further note that natural biological parameters could have been selected by evolution for functionality, including the ability to generate balance or imbalance detection. Together, these results show that this minimal model can generate the full range of observed response profiles for biologically reasonable parameter values.

Figure 10A:
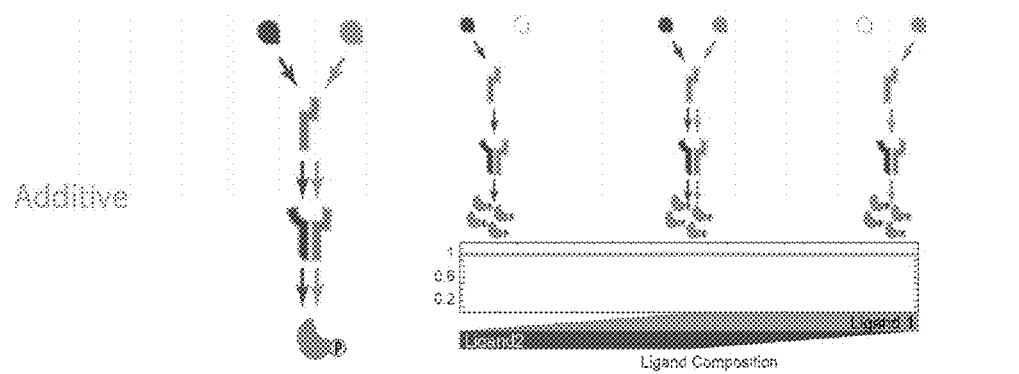
FIG. 10A shows a schematic representing an Additive computation in which the left-hand schematic represents a parameter regime sufficient for the computation corresponding to FIG. 11A, with arrow thicknesses represent the relative affinities or activities of indicated complexes, arrow color represents the identity of the ligand in a given complex, with the response profile across the ligand compositions is shown on the right, in which the behavior of the system is also indicated schematically above the plot for three ligand composition regimes: only one ligand present (left and right) or an equal mixture of ligands (center), with hollow ligands representing those not present in each case, where for each regime, some reactions don't occur (because a particular ligand is not present) or are disfavored (because of competition), and the total activity of the system in each of these three regimes is indicated by the number of copies of the phosphorylated second messenger, according to embodiments of the present disclosure.
Figure 10B:
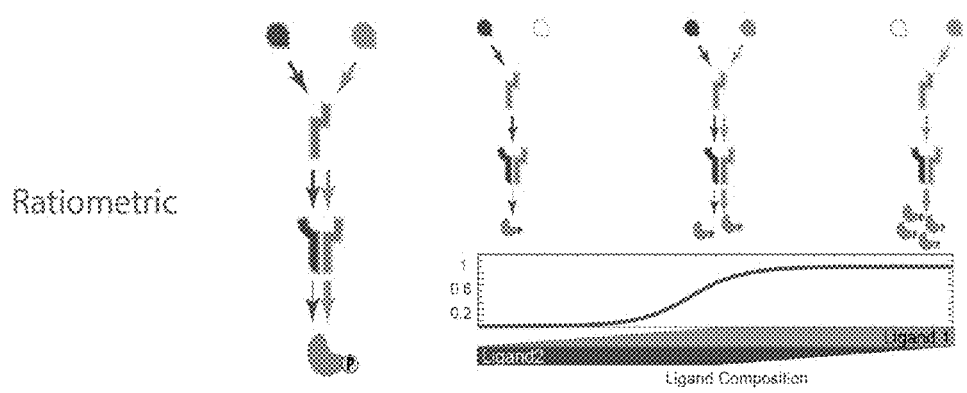
FIG. 10B shows a schematic representing a Ratiometric computation in which the left-hand schematic represents a parameter regime sufficient for the computation corresponding to FIG. 11A, with arrow thicknesses represent the relative affinities or activities of indicated complexes, arrow color represents the identity of the ligand in a given complex, with the response profile across the ligand compositions is shown on the right, in which the behavior of the system is also indicated schematically above the plot for three ligand composition regimes: only one ligand present (left and right) or an equal mixture of ligands (center), with hollow ligands representing those not present in each case, where for each regime, some reactions don't occur (because a particular ligand is not present) or are disfavored (because of competition), and the total activity of the system in each of these three regimes is indicated by the number of copies of the phosphorylated second messenger, according to embodiments of the present disclosure.
Figure 10C:
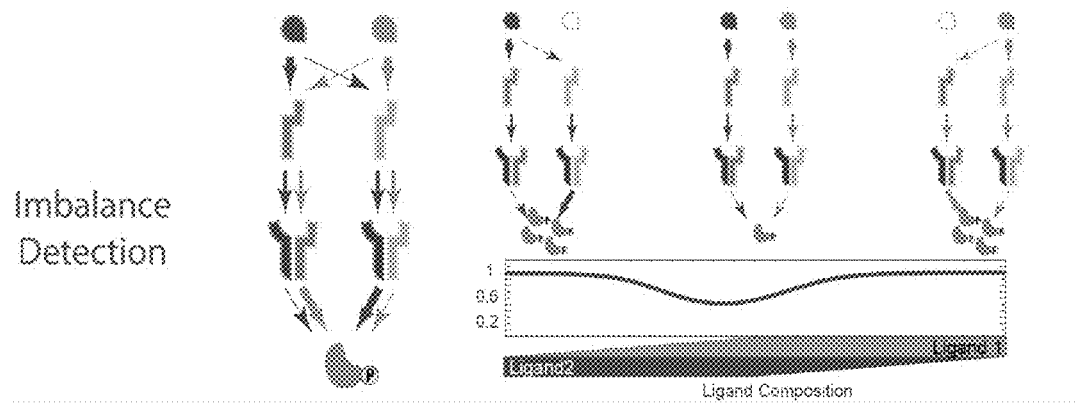
FIG. 10C shows a schematic representing an Imbalance Detection computation in which the left-hand schematic represents a parameter regime sufficient for the computation corresponding to FIG. 11A, with arrow thicknesses represent the relative affinities or activities of indicated complexes, arrow color represents the identity of the ligand in a given complex, with the response profile across the ligand compositions is shown on the right, in which the behavior of the system is also indicated schematically above the plot for three ligand composition regimes: only one ligand present (left and right) or an equal mixture of ligands (center), with hollow ligands representing those not present in each case, where for each regime, some reactions don't occur (because a particular ligand is not present) or are disfavored (because of competition), and the total activity of the system in each of these three regimes is indicated by the number of copies of the phosphorylated second messenger, according to embodiments of the present disclosure.
Figure 10D:
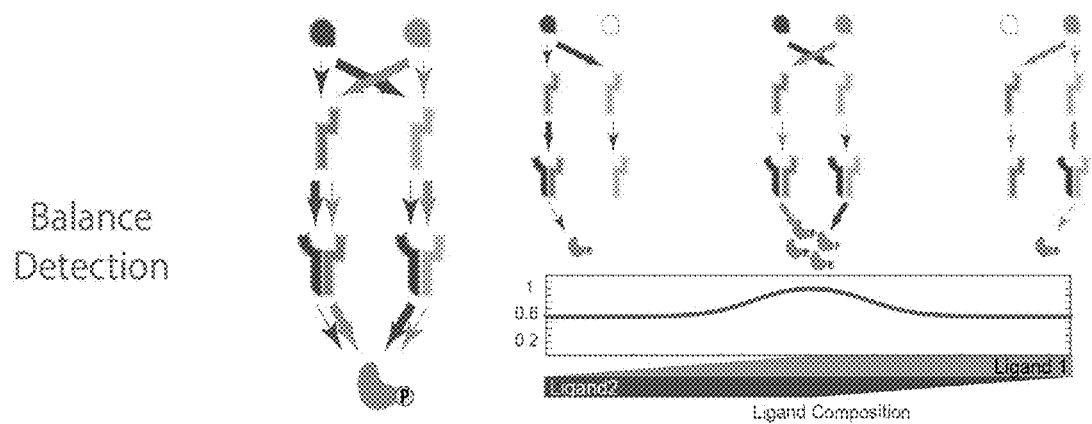
FIG. 10D shows a schematic representing a Balance Detection computation in which the left-hand schematic represents a parameter regime sufficient for the computation corresponding to FIG. 11A, with arrow thicknesses represent the relative affinities or activities of indicated complexes, arrow color represents the identity of the ligand in a given complex, with the response profile across the ligand compositions is shown on the right, in which the behavior of the system is also indicated schematically above the plot for three ligand composition regimes: only one ligand present (left and right) or an equal mixture of ligands (center), with hollow ligands representing those not present in each case, where for each regime, some reactions don't occur (because a particular ligand is not present) or are disfavored (because of competition), and the total activity of the system in each of these three regimes is indicated by the number of copies of the phosphorylated second messenger, according to embodiments of the present disclosure.
Figure 11E:
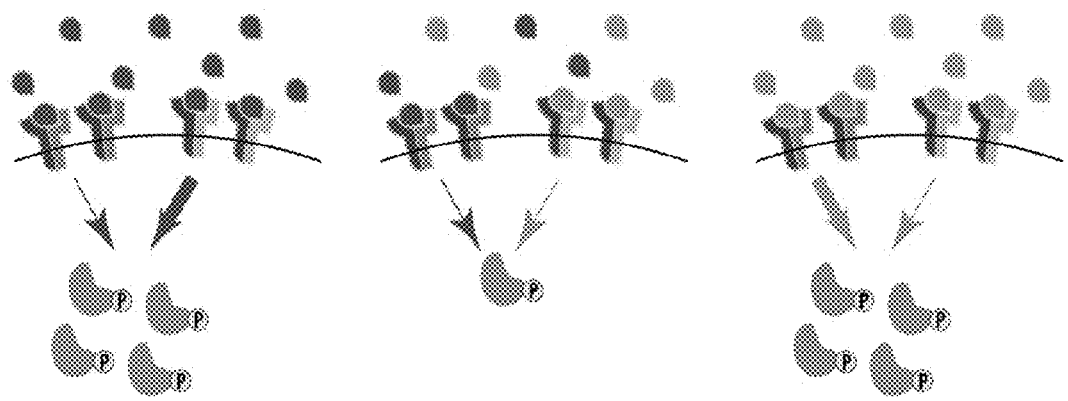
FIG. 11E is a schematic of the parameter regime corresponding to the imbalance detection, cells exposed only to a single ligand species (i.e. only blue or green ligands) produce a mixture of strong and weakly active complexes (left, right), but cells exposed to mixtures of the two ligands predominantly form weakly active complexes (middle), leading to the imbalance detection behavior, according to embodiments of the present disclosure.

Complex response profiles emerge from the interplay of receptor-ligand affinities and activities. We next asked how the archetypal ligand integration modes arise within the model. To do so, we analyzed the corresponding parameter regimes in more detail (FIGS. 10A-10D). As expected, additive responses occur when the two ligands are approximately equivalent, forming signaling complexes with similar phosphorylation activities ($\varepsilon_{i1k} \sim \varepsilon_{i2k}$, FIGS. 10A, 11A). By contrast, ratiometric behaviors occur when signaling complexes containing one ligand have higher activities than those containing the other ($\varepsilon_{i1k} \ll \varepsilon_{i2k}$), such that a weaker ligand competitively inhibits activation by the other, stronger ligand (FIGS. 10B, 11B). Imbalance detection occurs when each receptor preferentially binds to a distinct ligand with which it forms a less active signaling complex (FIGS. 10C, 11C). When only one type of ligand is present, it can bind both receptors, forming signaling complexes with both higher and lower activity. When both ligands are present, the affinity preferences cause ligands and receptors to self-sort, and predominantly form less active signaling complexes, reducing total pathway activity (FIG. 11E). Finally, balance detection occurs through a similar mechanism, except that the relative affinities are reversed, favoring formation of more active signaling complexes when both ligands are present (FIGS. 10D, 11D).

Figure 8F:
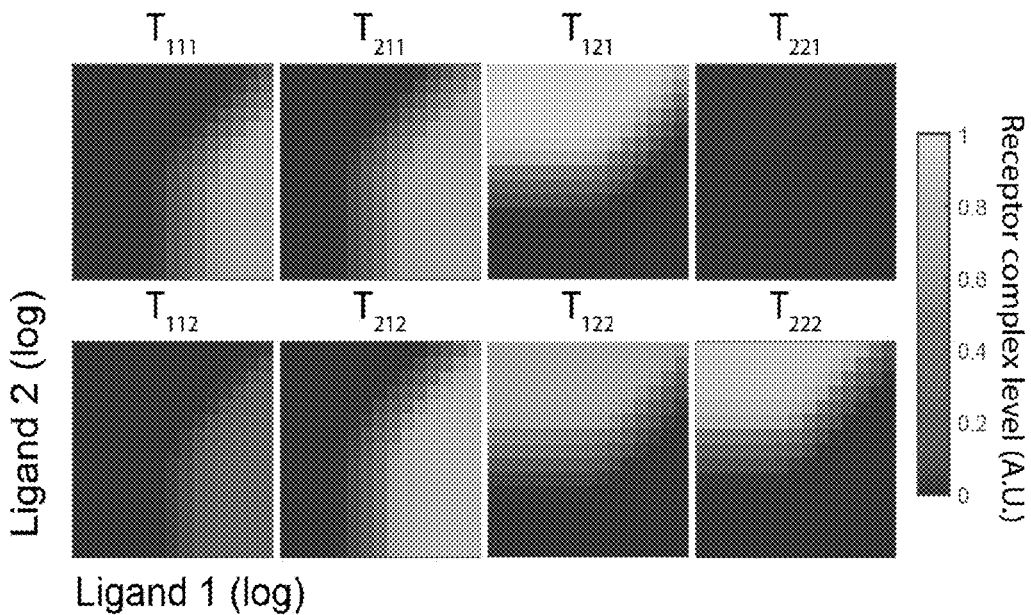
FIG. 8F shows ligand matrices for a specific set of $K_{ij}$, $K_{ijk}$ values as indicated, the level of each trimeric signaling complex, $T_{ijk}$, is plotted as a function of the concentrations of two ligands, according to embodiments of the present disclosure.
Figure 8G:
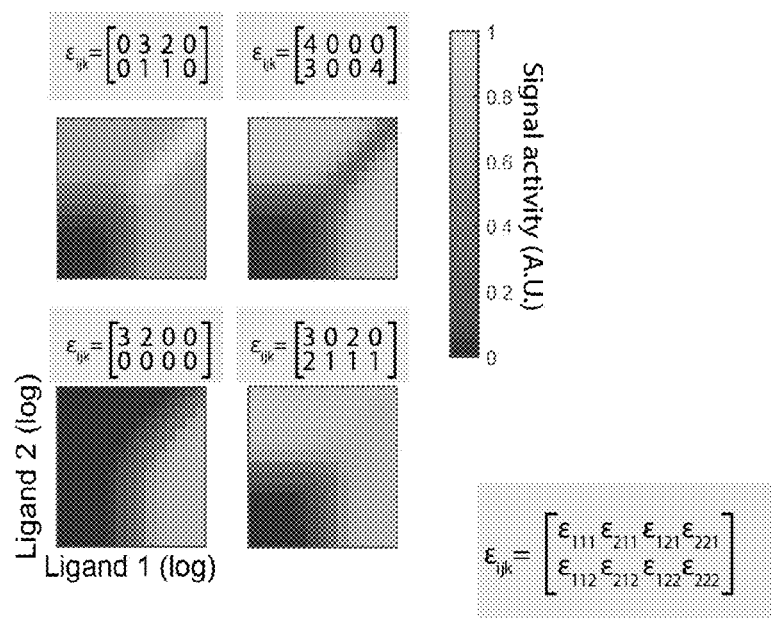
FIG. 8G shows ligand matrices for 4 specific sets of activities ($\varepsilon_{ijk}$), each of which generates a distinct response profile, despite using the same affinity parameters, showing that the total pathway response depends in general on the levels of all trimeric complexes, each multiplied by a corresponding activity parameter, according to embodiments of the present disclosure.

A critical feature of the model is that the overall activity of the pathway depends not only on how much of each ligand is complexed with receptors, but also on how that ligand is distributed across the range of distinct possible receptor complexes. In the model, simply changing the activities of the complexes can result in completely different response profiles (FIGS. 8F, 8G). As a result, addition of a second ligand can change not just the amount of the first ligand that is bound to receptors, but more importantly the distribution of that ligand across different potential signaling complexes with distinct activities. This could explain how two ligands can exhibit similar receptor preferences but still combine in qualitatively different ways with a third ligand.

Taken together, these results indicate that promiscuous receptor-ligand binding interactions are sufficient to produce a diverse repertoire of specific multi-ligand response profiles, including those observed experimentally. They reveal how the full functional repertoire can be understood as interpolating among three archetypal functions (ratiometric, imbalance detection, and the predicted balance detection function). Finally, they show how these functions arise through specific relations between the affinity parameters that control what receptor complexes will form, and the activity parameters that control how the resulting signaling complexes contribute to the cellular response. Thus, as suggested experimentally, the full spectrum of observed computations require only the ability of receptors and ligands to compete to form a variety of distinct signaling complexes, and differences in the relative activities of those complexes. Despite its simplicity, this system allows for remarkable computational diversity.

Receptor expression reprograms ligand response profiles. Within an organism, different cell types generally express receptors at different levels. Changes in receptor expression could in principle alter BMP responses in similar, or different, ways compared to changes in ligand concentrations. To gain insight into the possible role of receptor expression in pathway computations, we varied receptor expression levels in the model, while holding the biochemical parameter values ($K_{ij}^D$, $K_{ijk}^T$, $\varepsilon_{ijk}$) fixed. We repeated this analysis for different biochemical parameter sets. In these simulations, some biochemical parameter sets produced only a limited range of ligand integration modes (FIG. 12A, left), while others were more versatile, capable of generating a diverse range of computations as receptor expression levels were varied (FIG. 12A, right). The existence of such versatile parameter sets in the model suggests the hypothesis that different cell types, by expressing different receptor profiles, might compute different responses to the same ligands.

Figure 7G:
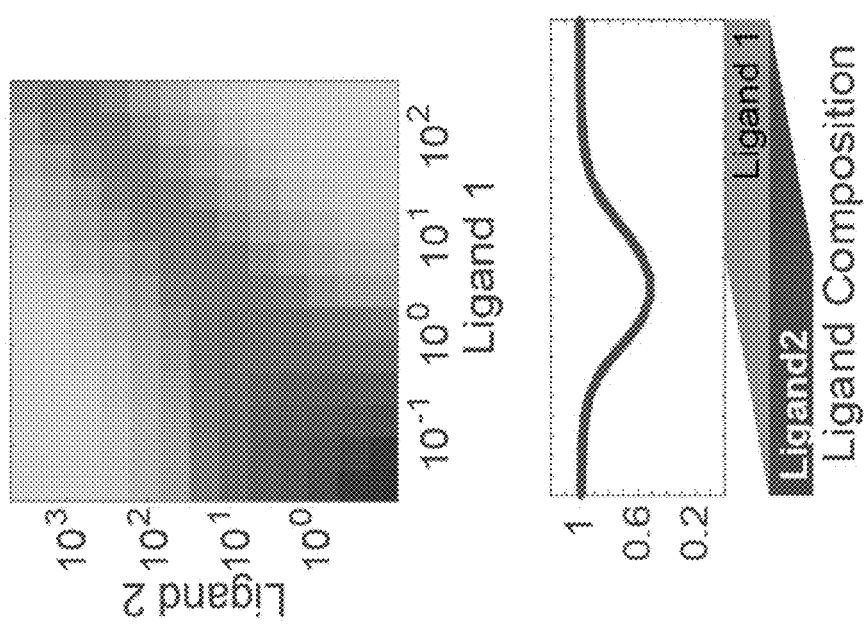
FIG. 7G shows a representative ligand matrix characterizing ligand-dependent response with each of Ligand 1 and Ligand 2 alone and in combination as a result of pathway activity as a function of ligand ratio in which Ligand 1 and Ligand 2 show a Balance type response in combination, according to embodiments of the present disclosure.

If the BMP pathway exhibits and utilizes such versatility, cell lines with different receptor expression profiles could show distinct response profiles for the same ligands. To test this hypothesis, we compared the response of NMuMG cells to E14 mouse embryonic stem (ES) cells, which express less BMPR2 and ACVR1 and more ACVR2B (FIG. 12B). As a control, we also analyzed NIH-3T3 fibroblasts, which had similar receptor expression to NMuMG cells (FIG. 12B). The ES cells indeed exhibited different response profiles compared to NMuMG for the same ligands (FIGS. 12C-12E, 13A). Most strikingly, BMP4 and BMP9 integrated in an additive fashion in NMuMG and NIH-3T3, but showed the balance detection archetype in ES cells (FIG. 12C). Other ligand pairs were also integrated similarly in NIH-3T3 and NMuMG, but differently in ES cells (FIGS. 12D-12E). Together, these results show that cell lines differ qualitatively in their ligand integration modes, in a manner that correlates with their receptor expression profiles, as predicted by the model. Furthermore, these results also validate the model prediction of balance detection (FIG. 7G).

Figure 12H:
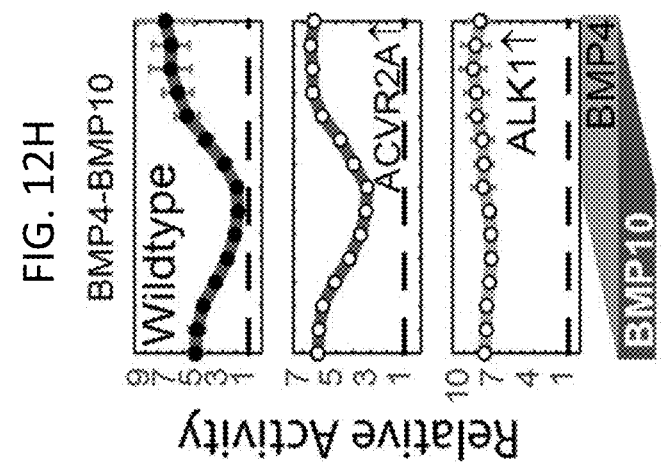
FIG. 12H shows computation correlates of perturbing receptor expression level reprograms computations in NMuMG cells for ligand pairs BMP4-BMP10, according to embodiments of the present disclosure.

Reprogramming response profiles by direct manipulation of receptor expression levels. Finally, to test whether changes in receptor expression are sufficient to reprogram computations, we directly perturbed receptor expression in NMuMG cells. Depletion of the most highly expressed type II receptor in this cell type, BMPR2, with siRNA, changed the BMP4-BMP9 response from additive to ratiometric (FIGS. 12F, 13C). This indicates that BMP4 activates the pathway predominantly through BMPR2. By contrast, BMP9 can activate through other type II receptors, but BMP4 can effectively inhibit such BMPR2-independent BMP9 signaling.

Figure 12G:
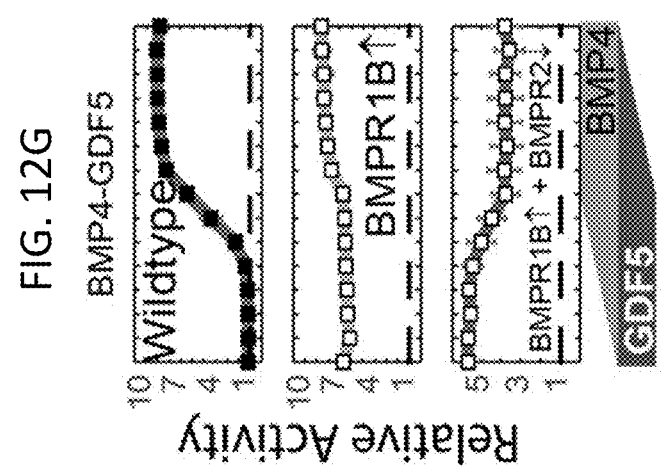
FIG. 12G shows computation correlates of perturbing receptor expression level reprograms computations in NMuMG cells for ligand pairs BMP4-GDF5, according to embodiments of the present disclosure.
Figure 12F:
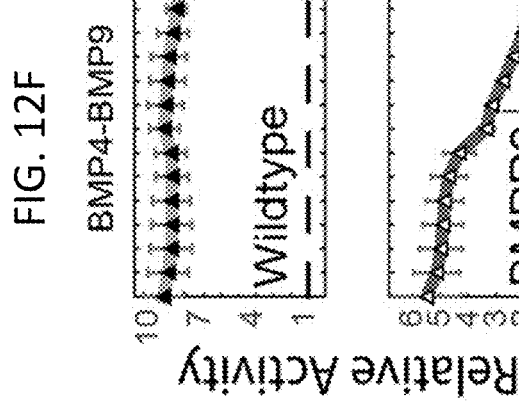
FIG. 12F shows computation correlates of perturbing receptor expression level reprograms computations in NMuMG cells for ligand pairs BMP4-BMP9, according to embodiments of the present disclosure.
Figure 12I:
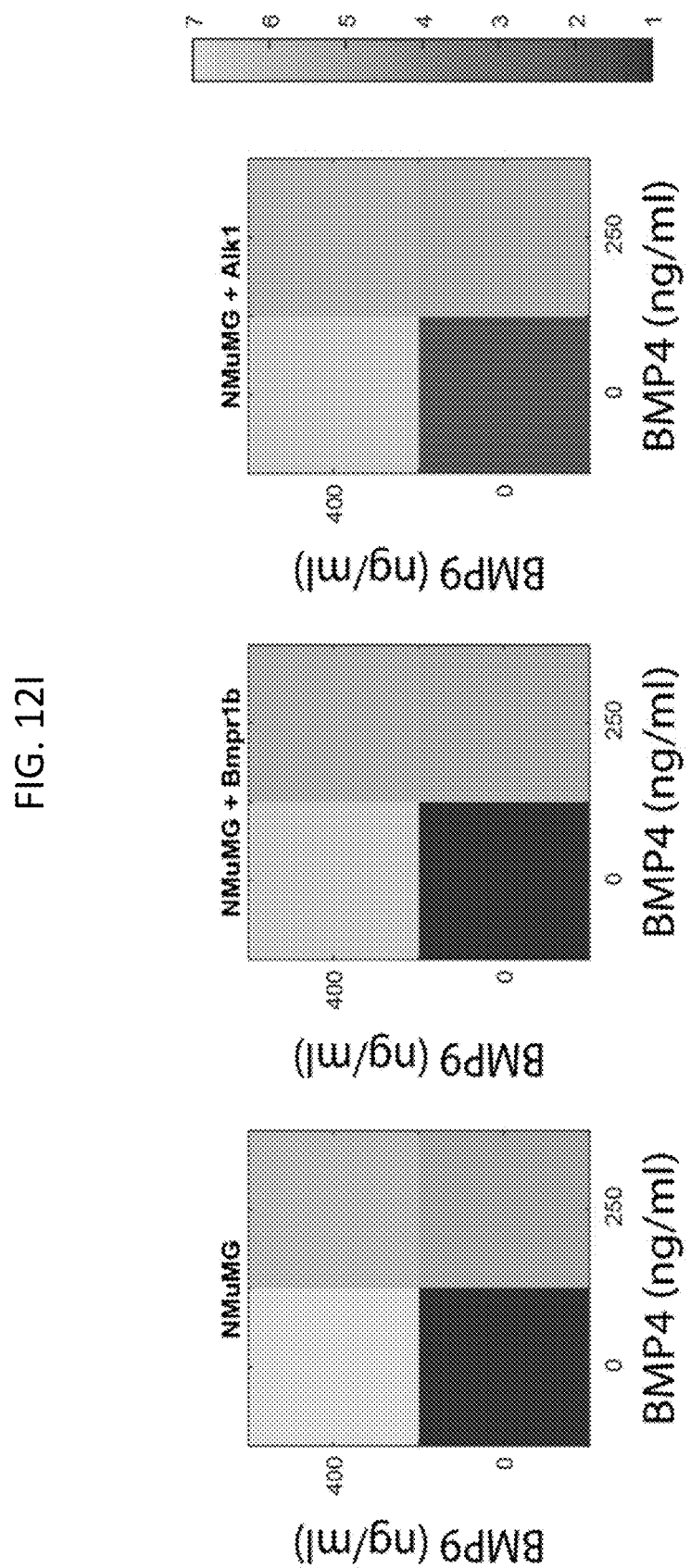
FIG. 12I shows a ligand matrix for NMuMG, NMuMG with overexpressed BMPR1B, and NMuMG with overexpressed ALK1 cells exposed in the indicated concentrations to BMP4 and BMP9.
Figure 12J:
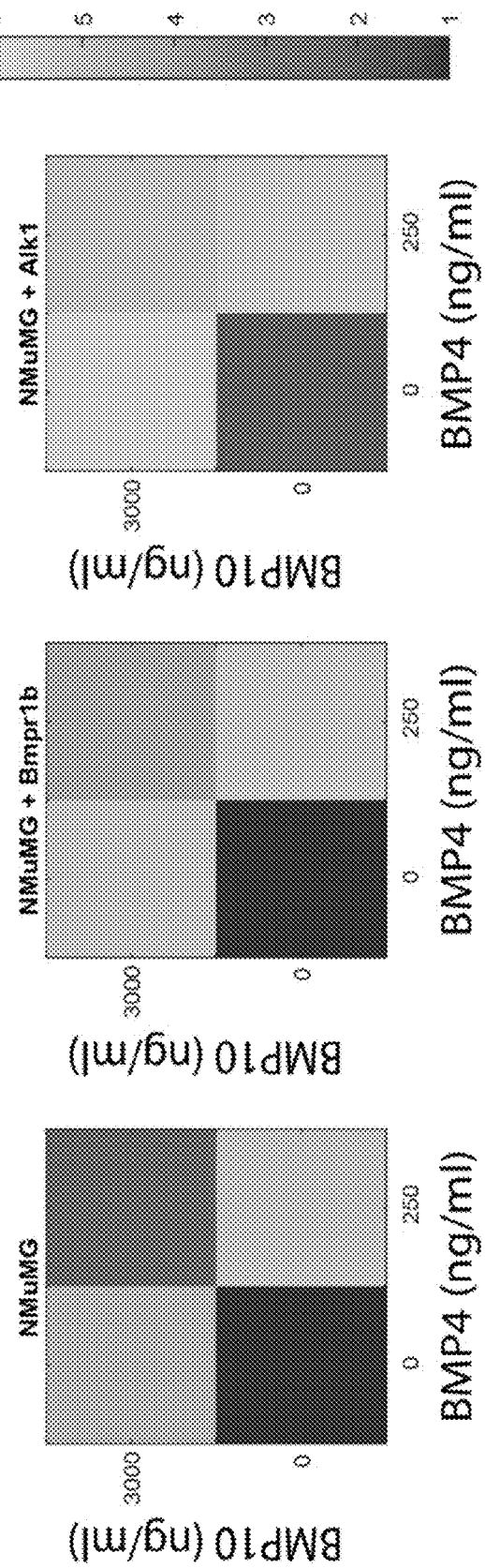
FIG. 12J shows a ligand matrix for NMuMG, NMuMG with overexpressed BMPR1B, and NMuMG with overexpressed ALK1 cells exposed in the indicated concentrations to BMP4 and BMP10.

As a second example, ectopically expressed BMPR1B, which is known to mediate GDF5 signaling enabled GDF5 to activate, rather than inhibit, the pathway, and thereby reprogrammed the ratiometric BMP4-GDF5 interaction to an additive one (FIGS. 12G, 13C). Furthermore, combining ectopic BMPR1B to enable GDF5 signaling with depletion of BMPR2 to reduce BMP4-dependent signaling inverted the ratiometric response (FIGS. 12G, 13C).

Third, we asked whether we could reprogram imbalance detection between BMP4 and BMP10 (FIG. 3D). In the model, imbalance detection results from ligand competition for receptors. To alleviate this competition, we ectopically expressed the ALK1 receptor, which is known to mediate BMP9 and BMP10 signaling. This perturbation indeed removed competition, generating the predicted additive response (FIGS. 12H, 13C).

Figure 13A:
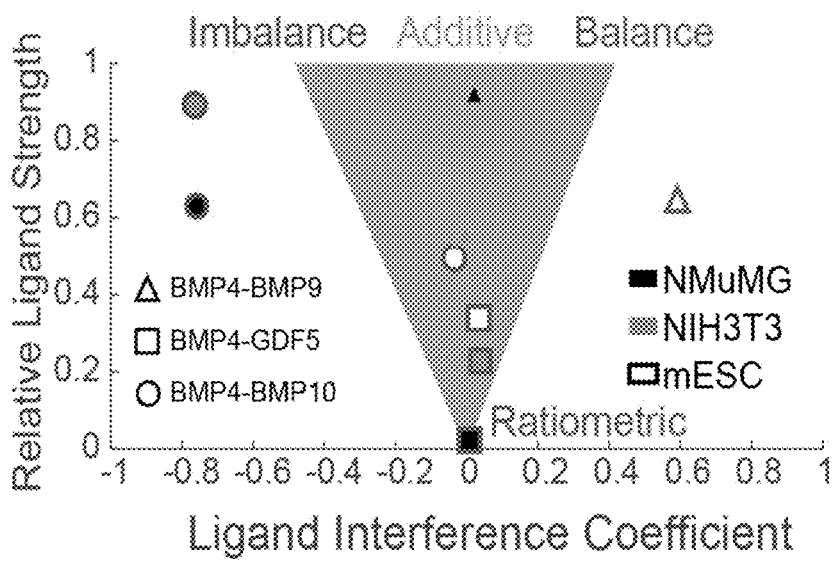
FIG. 13A shows the relative ligand strength (RLS) and ligand interference coefficient (LIC) are plotted for each ligand pair (shape), for different cell lines (fill style).
Figure 13B:
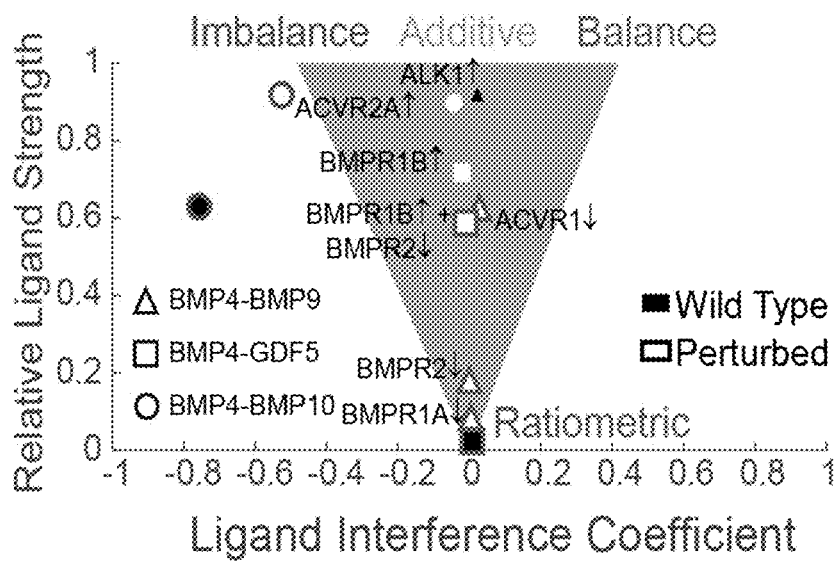
FIG. 13B shows RLS and LIC are plotted for each ligand pair (shape), for wild-type (filled), and each indicated receptor perturbation (hollow).
Figure 13C:
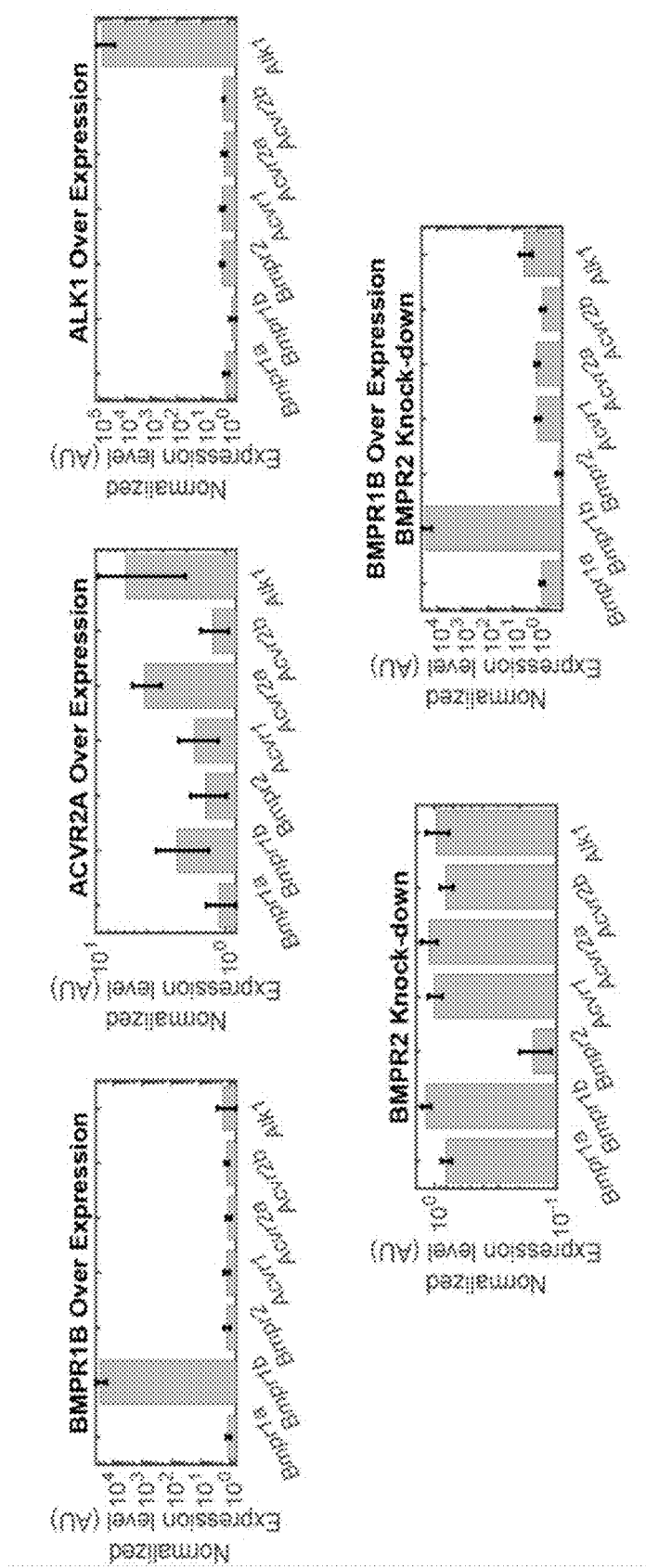
FIG. 13C shows expression levels of all 7 BMP receptors in NMuMG cells were measured using RT-qPCR, for each receptor perturbation (indicated) to quantify the effect size and specificity of knockdown or overexpression where the values represent fold expression relative to Sdha expression, relative to control cells, either wildtype (for receptor overexpression) or a non-specific siRNA (for receptor knock down).
Figure 13F:
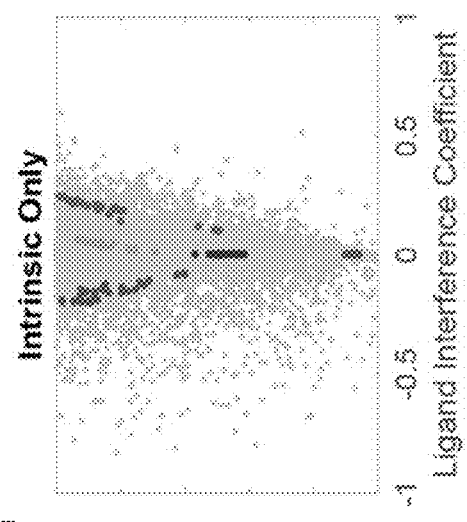
FIGS. 13D, 13E, and 13F show effects of noise in receptor expression on ligand integration mode with the effects of noise analyzed on 5 specific parameter sets representing different response profiles (colors), and for each parameter set, we analyzed 25 randomly perturbed receptor expression profiles chosen from a gamma distribution with a coefficient of variation (CV) of 0.25, with each resulting interaction profile is plotted in the LIC-RLS phenotypic space.
Figure 13E:
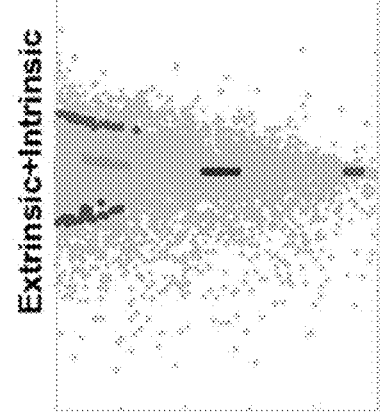
Figure 13D:
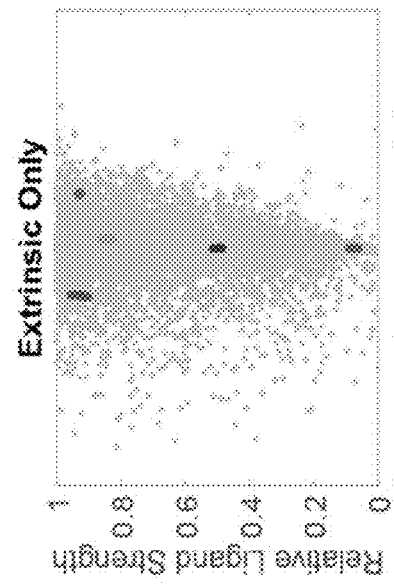
Figure 13G:
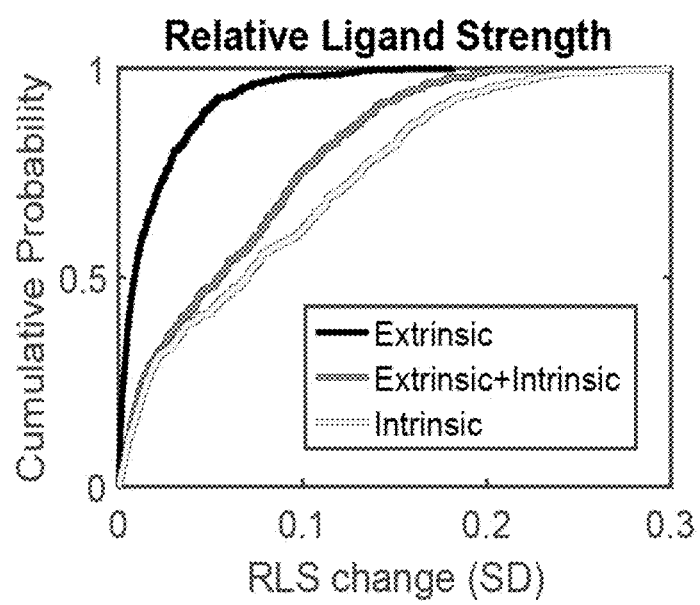
FIG. 13G shows the cumulative distribution function of the standard deviations in the RLS.
Figure 13H:
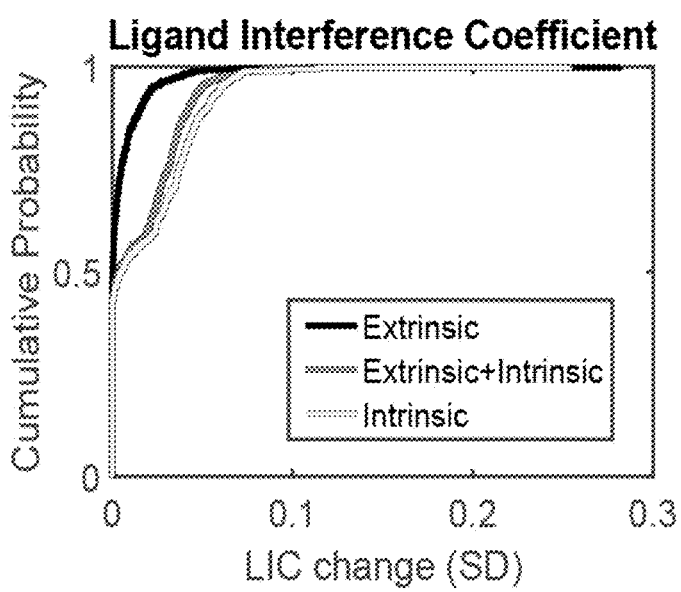
FIG. 13H shows that the LIC is shown to indicate the distribution of sensitivities of ligand integration behavior to each category of noise.

Taken together, these results show that receptor expression levels directly control computations, and demonstrate that this effect enables rational manipulation of ligand integration modes using insights from the model (FIG. 13B).

Figure 14:
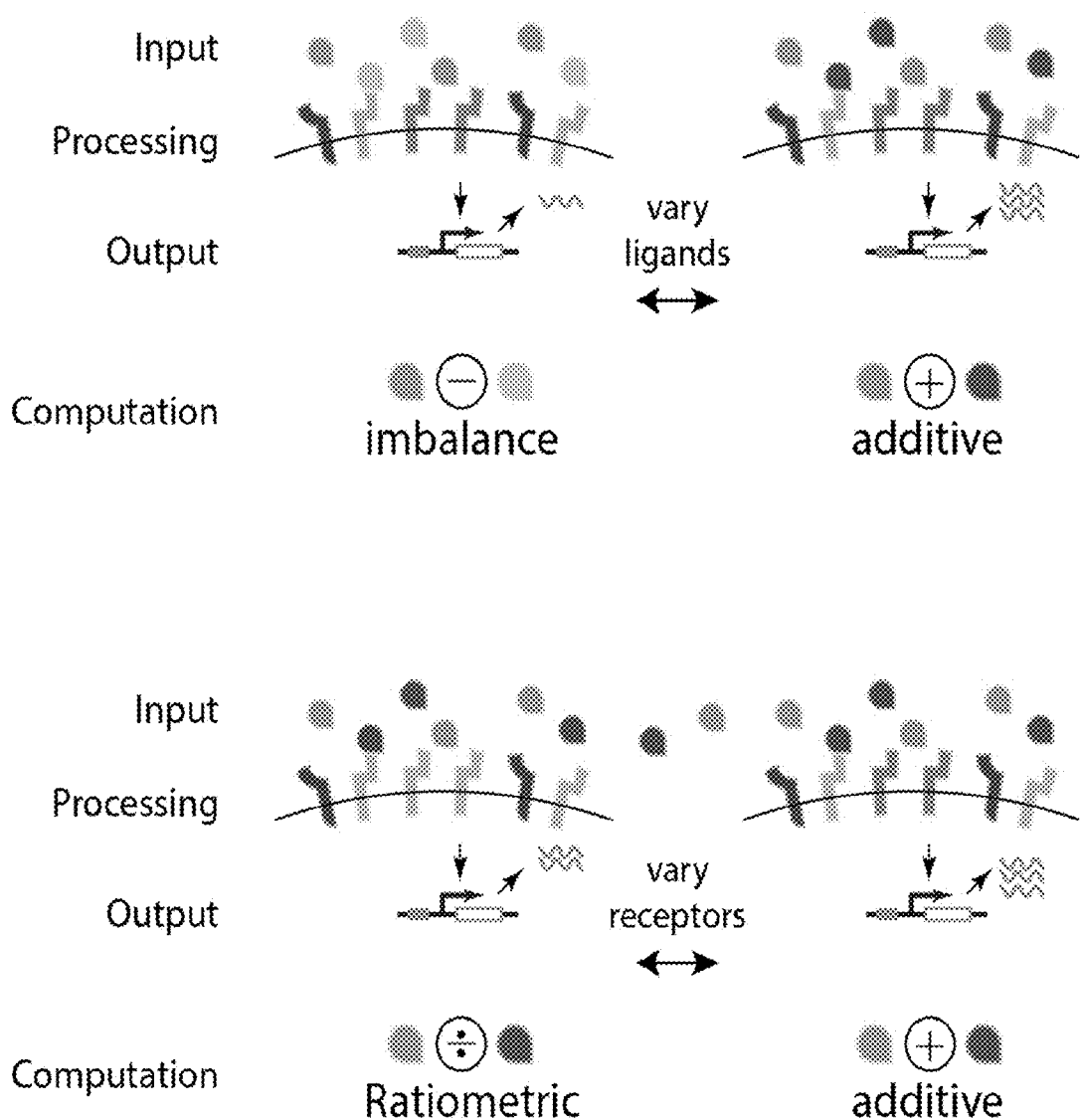
FIG. 14 is a schematic illustration of computational plasticity in the BMP signaling system where ligand combinations represent inputs to the pathway, which processes them through receptor-ligand interactions to control the expression level of downstream target genes. In this scheme, a given receptor configuration can perform different computations on different ligand combinations (e.g. additive and imbalance, top panel), whereas cells expressing different receptor profiles can perform distinct computations on the same combination of ligands (e.g. ratiometric and additive, lower panel).

Discussion. The results disclosed herein show that promiscuous BMP receptor-ligand interactions enable cells to perceive information encoded in combinations of ligands (FIG. 14). They do so through a specific set of computations over the multi-dimensional space of ligand concentrations, with the computations performed on a given set of ligands depending on the repertoire of receptors the cell expresses. These computations interpolate between archetypes loosely analogous to addition (additive), subtraction (imbalance detection), multiplication (balance detection), and division (ratiometric). This indicates that cells do not, in general, perceive ligand abundance, but rather perceive specific functions of ligand combinations.

This system provides several key capabilities for cells: First, it is sensitive to both absolute concentrations of individual ligands and their relative concentrations. Encoding signals in relative ligand concentrations can increase robustness to variations in ligand accessibility, cell surface area, and other properties that affect all ligands in a correlated way. Second, computation is integrated with sensing. The system performs computations on ligand concentrations directly through competitive binding interactions, at steady state, without requiring regulatory cascades or transcriptional feedback loops. The observed computations arise because affinities among components need not correlate with the activities of the resulting signaling complexes. This allows ligands to compete for receptors to form a variety of distinct signaling complexes with distinct efficiencies. Third, and most intriguingly, this system possesses computational plasticity. By controlling the abundance of different receptor variants, a cell can control which computations it performs, and thus what features of the ligand environment it responds to. These capabilities could enable non-intuitive operative modes. For example, the use of ligand combinations may offer the ability to selectively activate a given cell type, since different cell types may respond to specific ligand combinations. Temporal changes in the concentration of a single ligand could elicit different, or opposite, changes in signal perception in distinct cell types.

These results should improve our ability to understand and manipulate natural BMP-dependent processes. For example, efficient primordial germ cell differentiation was shown to require a combination of both BMP4 and BMP8B homodimers, provoking the question of whether these ligands are integrated through balance detection. Conversely, BMP2 and BMP7 show opposing effects on ureter branching in developing kidneys, suggesting they may operate in a ratiometric mode, and similar interactions were recently reported for BMP2 and GDF5 in multiple contexts. The framework described here can be used to analyze these and other specific biological processes that utilize multiple BMPs. In the context of disease, many therapeutic strategies have focused on using a single ligand to treat conditions such as bone injuries and abnormalities, arthritis, diabetes, vascular conditions, obesity, and cancer. Similarly, directed differentiation approaches in regenerative medicine often rely on a single BMP ligand. However, ligand combinations may provide more potent, and specific, control in these contexts.

Tissue Culture and Cell Lines

NMuMG (NAMRU Mouse Mammary Gland cells, female) and NIH3T3 (mouse fibroblast, male) cells were acquired from ATCC (CRL-1636 and CRL-1658, respectively). E14 cells (mouse embryonic stem cells, E14Tg2a.4, male) were obtained from Bill Skarnes and Peri Tate. All cells were cultured in a humidity controlled chamber at 37° C. with 5% CO2. NMuMG cells were cultured in DMEM supplemented with 10% FBS (Clonetech #631367), 1 mM sodium pyruvate, 1 unit/ml penicillin, 1 ug/ml streptomycin, 2 mM L-glutamine and 1×MEM non-essential amino acids. NIH-3T3 cells were cultured in DMEM supplemented with 10% CCS (Hyclone #SH30087), 1 mM sodium pyruvate, 1 unit/ml penicillin, 1 ug/ml streptomycin and 2 mM L-glutamine. ES cells were plated on tissue culture plates pre-coated with 0.1% gelatin and cultured in a standard pluripotency-maintaining conditions (Smith, 2001) using DMEM supplemented with 15% FBS (ES qualified, Gibco #16141), 1 mM sodium pyruvate, 1 unit/ml penicillin, 1 ug/ml streptomycin, 2 mM L-glutamine 1×MEM non-essential amino acids 55 mM β-mercaptoethanol and 1000 Units/ml leukemia inhibitory factor (LIF).

Sensor Cell Lines Construction

Construction of the reporter cell lines was carried out via random integration of a plasmid harboring the BMP response element (BRE) (Korchynskyi and ten Dijke, 2002) in the enhancer region of a minimal CMV driving the expression of an H2B-Citrine protein fusion. ES cells were transfected using the FugeneHD reagent. NMuMG and 3T3 cells were transfected using Lipofectamine LTX. After transfection, cells were selected with 100 ug/ml hygromycin. All experiments were performed with clonal populations, generated via colony picking (ES) or limiting dilutions (NMuMG, NIH3T3). To ensure results were not dependent on the specific reporter integration site, an independent BRE-reporter cell line was generated using Piggybac integration (SBI) (see FIG. 6A).

Methods

BMP response and flow cytometry. Sensor cell lines were plated at 40% confluency in 96 well plates and cultured under standard conditions (above) for 12h. Media was then replaced and ligand(s) were added at specified concentrations. 24h after ligand addition cells were prepared for flow cytometry in the following way: Cells were washed with PBS and lifted from the plate using either 0.05 ml Accutase (ES cells) or trypsin (NMuMG and 3T3 cells) for 5 minutes at 37° C. Protease activity was quenched by re-suspending the cells in HBSS with 1.0% Bovine Serum Albumin (BSA). Cells were then filtered with a 40 μm mesh and analyzed by flow cytometry (MACSQuant VYB, Miltenyi). All recombinant BMP ligands were acquired from R&D Systems with the exception that BMP4, BMP10 and GDF5 were acquired from Peprotech®.

Ligand integration survey. In order to identify non-additive ligand integration modes, cells were exposed to a matrix of ligands at predetermined concentrations. We selected concentrations that were sufficient to induce responses in cells already known to respond to those ligands, but not so high as to induce potential non-specific responses. For this reason, we based ligand concentrations on supplier data, and selected a concentration at the high end of the input dynamic range for a cell based system susceptible to each ligand). All BMP ligands used in the survey were acquired from R&D Systems SDS-PAGE and Immunoblotting.

Phoshpo-SMAD 1/5/8. For assessment of phoshpo-SMAD1/5/8 cells were plated at 40% confluency under standard conditions in 24 well plates. To reduce phospho-SMAD1/5/8 background activity, cells were transferred to reduced serum media containing 1.0% FBS for 12 hours. This media was then exchanged for DMEM and cells were incubated at 37° C. for another 6 hours. DMEM was then replaced and ligands were added in DMEM at the specified concentrations and incubated at 37° C. for 20 minutes. Cells were then treated with 50 µl lysis buffer (Cell Signaling 9803) with the following additions, 0.1M DTT, 50 mM NaF, 1 mM PMSF and additional protease inhibitors (Thermo 87785). Samples were immediately stored at −80° C. until processed for SDS-PAGE. SDS-PAGE was conducted using NuPAGE Bis-Tris Mini Gels 4-12% (Thermo). Approximately 10-20 µg of total protein, denatured by heat, was loaded per well. Samples were run at 50 mA for approximately 60 minutes. Protein was transferred from gels to nitrocellulose using the iBlot apparatus and iBlot reagents (Thermo) and program 2 for 8 minutes. Membranes were trimmed and blocked with 5% milk in Tris buffered saline with 0.1% Tween 20 (TBST) for at least 60 minutes at room temperature. Blocking buffer was removed and membranes were briefly washed with TBST. Antibodies against phospho-SMAD 1/5/8 (13820 Cell Signaling), phospho-p44/42 MAPK (4370 Cell Signaling), SMAD1 (6944 Cell Signaling), GAPDH (2118 Cell Signaling) were than applied at a dilution of 1:1000, 1:2000 for GAPDH, in 1.0% BSA TBST and incubated at 4° C. for 12 to 16 hours. After incubation with primary antibody, immunoblots were washed with TBST three times for 5 minutes at room temperature and a secondary antibody conjugated with horse radish peroxidase (7074 Cell Signaling) was applied to the blots at 1:1000 in 1.0% BSA TBST for 60 minutes at room temperature. After incubation with the secondary antibody, the immunoblots were washed with TBST three times for 5 minutes and developed using a luminol based substrate (7003 Cell Signaling). The immunoblots were imaged using a BioRad and exposure times that produced signal below saturation. Densitometry was performed using ImageJ (http://imagej.nih.gov).

BMPR2. For assessment of BMPR2 protein expression after addition of select BMP ligands, cells were plated at 40% confluency under standard conditions in 24 well plates. Media was replaced, with addition of BMP9 (400 ng/ml), and cells were then incubated at 37° C. for the specified times. Cells were then treated with 50 µl lysis buffer (see above). Samples were immediately stored at −80° C. until processed for SDS-PAGE. After electrophoresis, gels were incubated with 20% Ethanol in TBS for 5 minutes. Transfer of protein to nitrocellulose was performed with the iBlot apparatus using program 3 for 8 minutes. Antibodies against BMPR2 (6979 Cell Signaling) and GAPDH (2118 Cell Signaling) were than applied at 1:1000 and 1:2000, respectively, in 1.0% BSA TBST and incubated at 4° C. for 12 to 16 hours. Immunoblots were processed, developed and analyzed as described above.

BMP response with heparinase I/III. Cells were plated at 40% confluency in 96 well plates and cultured under standard conditions for 12 hours. Media was exchanged with media containing 2 units of Heparinase I/III (H3917 SIGMA) and cells were incubated at 37° C. for 3 hours. Media was then replaced with media containing ligands at the specified concentrations. The cells were then incubated with ligands at 37° C. for 20 minutes. After incubation for 20 minutes the cells were processed for phoshpo-SMAD 1/5/8 staining and flow cytometry as described above.

BMP response with NaClO3. Sensor cells were plated at 40% confluency under standard conditions including 20 mM NaClO3 (Sigma) and passaged 36 hours later at 40% confluency in 96 well plates under the same conditions and cultured for another 12 hours. Media was then replaced and ligands were added at the specified concentrations. The cells were then incubated with ligands at 37° C. for 24 hours and were processed for flow cytometry as previously described.

Receptor over-expression. Overexpression plasmids were constructed for each of the BMP receptors (BMPR1A, BMPR1B, BMPR2, ACVR1, ACVR2A, ACVR2B and ALK1) using the Gibson cloning method. Bmpr1b and Alk1 cDNA was purchased from Dharmacon (MMM1013-202858407 and MMM1013-202763719). All other receptor cDNAs were generated by RT-PCR from total RNA extracted from NMuMG cells. The receptor cDNA was concatenated with mTurquoise with an intervening T2A cleavage site and was expressed under the control of a constitutive PGK promoter integrated in the Pb510b plasmid backbone to enable PiggyBac integration. Stable integrations were then generated using the PiggyBac method. Cells were co-transfected with these overexpression plasmids and PB200A to express transposase, and selected with Geneticin. Experiments were performed with polyclonal populations resulting from PiggyBac integrations.

siRNA Induced Knock-Down.

Cells were plated at 40% confluency with 30 µM total siRNA (ThermoFisher silencer select #4390771) and 30 RNAiMAX (Life technologies). For every gene, a pool of two distinct siRNA were used. Cells were passaged after 24h and were used for the relevant experiments.

Quantitative PCR (qPCR)

Total RNA was harvested from cell lysate using the RNAeasy mini kit (Qiagen) and cDNA was generated from one microgram of RNA using the iScript cDNA synthesis kit (BioRad) following the manufacturer's instructions. Primers and probes for specific genes were purchased from IDT. Reactions were performed using 1:40 dilution of the cDNA synthesis product with either IQ SYBR Green Supermix or SsoAdvanced Universal probes Supermix (BioRad). Cycling was carried out on a BioRad CFX96 thermocycler using an initial denaturing incubation of 95° for 3 minutes followed by 39 cycles of (95° C. for 15 seconds, followed by 60° C. for 30 seconds). Each condition was assessed with two biological repeats and each reaction was run at least in triplicate.

Antibody Detection for Phospho-SMAD1/5/8.

Cells exposed to specified concentrations of BMP4 for 24 hours were harvested from single wells of a 24 well plate using either 0.05 ml Accutase (ES cells) or trypsin (NMuMG and 3T3 cells). Protease activity was quenched by re-suspending the cells in 0.45 ml HBSS with 1.0% Bovine Serum Albumin (BSA). The cells were then pelleted, washed with 0.5 ml PBS and fixed by re-suspension in 0.5 ml of 4.0% formaldehyde for 5 minutes at room temperature. Following fixation, the cells were washed in 0.5 ml PBS and re-suspended in 0.5 ml PBS with 1.0% Triton X-100 for permeabilization. The cells were then washed with 0.5 ml PBS and re-suspended in blocking solution (PBS with 1.0% BSA and 0.1% Tween 20). Blocking was carried out for 30 minutes at room temperature. The cells were then pelleted and re-suspended in binding solution (PBS with 1.0% BSA) containing a 1:100 dilution of a primary antibody against the phosphorylated form of SMAD1/5/8 complex (Cell Signaling Technologies Cat#13820). The staining proceeded for 12-16 hours at 4° C. with constant rocking. Afterwards, cells were washed with 0.5 ml PBS and re-suspended in binding solution containing a 1:500 dilution of a secondary antibody labeled with Alexa 594 (#A21207, ThermoFisher). Secondary detection proceeded for 60 minutes at room temperature with constant rocking. Finally, cells were then pelleted, washed with 0.5 ml PBS filtered with a 40 µm mesh and analyzed by flow cytometry.

Time lapse imaging. Fluorescent reporter cells were first mixed with an excess of non-fluorescent parental cells at a 1:9 ratio to simplify image segmentation and data extraction. Cells were then plated at 1.6-104 cells/well in a 96 well plate equivalent roughly to 15-20% confluency. Cells were grown for 12 hours prior to ligand addition. Each position was imaged every hour starting from the addition of ligands until cells became confluent after about 60h. Images were then analyzed for the number of fluorescent cells and fluorescent signal level.

Mathematical Model for promiscuous interactions. Many signaling pathways comprise multiple ligand and receptor variants that interact promiscuously with one another, with varying affinities, to form many distinct signaling complexes. BMP provides a canonical example of this architecture. However, other pathways, including TGF-β (SMAD2/3) signaling, FGF, Wnt, and JAK/STAT, also exhibit similar features. Here we develop a general mathematical model that captures essential aspects of receptor-ligand promiscuity in signaling pathways, and analyze it to understand the functional capabilities this architectural feature provides for cellular signal processing. This model focuses on several features of the natural BMP pathway: promiscuous ligand-receptor interactions, heterodimeric receptors (a simplified version of the natural Type I-Type II receptor tetramers), and variation in the activities of different signaling complexes. To focus on the signal processing capabilities at the level of receptor-ligand interactions, we neglect other known features of the pathway including preliminary enzymatic processing of ligands, non-canonical signaling, downstream feedback loops (e.g. through SMAD6/7), and crosstalk with other signaling pathways. We specifically point out that while this model focuses on mixture of ligand species, each ligand type is composed of two subunits. Thus the model can be used equally well for mixtures of homodimers, heterodimers, or combinations thereof. Finally, we note that while the model applies most directly to the BMP pathway, variants of it could also describe other systems that similarly form multi-part signaling complexes, including receptor aggregates, such as those listed above.

We consider a system with $n_L$ ligands, $L_j$, each of which can bind to one of $n_A$ type A receptor sub-units, $A_i$, to form $n_L \cdot n_A$ intermediate dimeric ligand-type A receptor complexes, $D_{ij}$. These complexes can in turn bind to one of $n_B$ type B receptor sub-units, $B_k$, to form $n_L \cdot n_A \cdot n_B$ different trimeric signaling complexes, $T_{ijk}$. We assume that the reactions are reversible and follow first-order reaction kinetics with forward reaction rates given by $k_{f_{ij}}^D$ and $k_{f_{ijk}}^T$ for the formation of dimeric and trimeric complexes, respectively, and with reverse reaction rates similarly given by $k_{r_{ij}}^D$ and $k_{r_{ijk}}^T$. These reactions can be summarized as follows $$A_i + L_j \underset{k_{r_{ij}}^D}{\overset{k_{f_{ij}}^D}{\rightleftarrows}} D_{ij} \qquad (1)$$

$$D_{ij} + B_k \underset{k_{r_{ijk}}^T}{\overset{k_{f_{ijk}}^T}{\rightleftarrows}} T_{ijk}. \qquad (2)$$

Next, the dynamical equations that describe these reactions are:

$$\frac{dL_j}{dt} = \frac{1}{V}\sum_{i=1}^{n_A} \left(-k_{f_{ij}}^D A_i L_j + k_{r_{ij}}^D D_{ij}\right) \qquad (3)$$

-continued $$\frac{dA_i}{dt} = \sum_{j=1}^{n_L} \left(-k_{f_{ij}}^D A_i L_j + k_{r_{ij}}^D D_{ij}\right) \qquad (4)$$

$$\frac{dD_{ij}}{dt} = k_{f_{ij}}^D A_i L_j - k_{r_{ij}}^D D_{ij} + \sum_{k=1}^{n_B} \left(-k_{f_{ijk}}^T D_{ij} B_k + k_{r_{ijk}}^T T_{ijk}\right) \qquad (5)$$

$$\frac{dB_k}{dt} = \sum_{i=1}^{n_A}\sum_{j=1}^{n_L} \left(-k_{f_{ijk}}^T D_{ij} B_k + k_{r_{ijk}}^T T_{ijk}\right) \qquad (6)$$

$$\frac{dT_{ijk}}{dt} = k_{f_{ijk}}^T D_{ij} B_k - k_{r_{ijk}}^T T_{ijk}. \qquad (7)$$

Here, $L_j$ denotes the concentration of the ligand in a volume V, and $A_i$, $B_k$, $D_{ij}$ and $T_{ijk}$ are the absolute number of receptors and complexes on the cell surface. We assume here that production and consumption are in steady-state, enabling us to neglect the consumption of receptors and ligands by endocytosis. Subunits combine to form various complexes, however the principle of conservation of mass requires that the total number of each type of molecule remain constant:

$$L_j^0 = L_j + \frac{1}{V}\left(\sum_{i=1}^{n_A} D_{ij} + \sum_{i=1}^{n_A}\sum_{k=1}^{n_B} T_{ijk}\right) \qquad (8)$$

$$A_i^0 = A_i + \sum_{j=1}^{n_L} D_{ij} + \sum_{j=1}^{n_L}\sum_{k=1}^{n_B} T_{ijk} \qquad (9)$$

$$B_k^0 = B_k + \sum_{i=1}^{n_A}\sum_{j=1}^{n_L} T_{ijk}, \qquad (10)$$

where $L_j^0$ is the total ligand concentration and $A_i^0$ and $B_i^0$ are the total receptor levels. Finally, each complex $T_{ijk}$ induces phosphorylation of the intracellular signal, S, at some rate $\in_{ijk}$ so that the rate of change of the total signal is given by $$\frac{dS}{dt} = \sum_{i=1}^{n_A}\sum_{j=1}^{n_L}\sum_{k=1}^{n_B} \in_{ijk} T_{ijk} - \gamma S. \qquad (11)$$

We consider the case where the volume for the ligand is large such that there are significantly more ligand molecules than receptors, which can be expressed by V→∞. This reflects our experimental conditions where the ligands are dissolved within a large excess of cell culture media. With this assumption equations (3) and (8) decouple and become $$L_j = L_j^0. \qquad (12)$$

Additionally, since binding and unbinding occur on fast timescales (minutes (Heinecke et al., 2009)) compared to the timescales of reporter expression, we focused on the behavior of this system at steady state. In this regime, all time derivatives in equations (4-7) vanish and the system can be solved to give $$D_{ij} = K_{ij}^D A_i L_j \qquad (13)$$

$$T_{ijk} = K_{ijk}^T D_{ij} B_k \qquad (14)$$

where we define $K_{ijk}^T \equiv k_{f_{ijk}}^T / k_{r_{ijk}}^T$, and $K_{ij}^D \equiv k_{f_{ij}}^D / k_{r_{ij}}^D$. Stronger affinity thus corresponds to larger values of the K's. Similarly, setting equation (11) to zero we get $$S = \sum_{i=1}^{n_A} \sum_{j=1}^{n_L} \sum_{k=1}^{n_B} \varepsilon_{ijk} T_{ijk}, \quad (15)$$

with $\varepsilon_{ijk} \equiv \in_{ijk}/\gamma$. Therefore, the final system of equations describing our model is given as follows $$A_i^0 = A_i + \sum_{j=1}^{n_L} D_{ij} + \sum_{j=1}^{n_L} \sum_{k=1}^{n_B} T_{ijk} \quad (16)$$

$$B_k^0 = B_k + \sum_{i=1}^{n_A} \sum_{j=1}^{n_L} T_{ijk} \quad (17)$$

$$D_{ij} = K_{ij}^D A_i L_j \quad (18)$$

$$T_{ijk} = K_{ijk}^T D_{ij} B_k \quad (19)$$

$$S = \sum_{i=1}^{n_A} \sum_{j=1}^{n_L} \sum_{k=1}^{n_B} \varepsilon_{ijk} T_{ijk}. \quad (20)$$

This system comprises a set of $N_v = n_A + n_B + n_A(1+n_B)n_L + 1$ variables and $N_p = n_A + n_B + n_A(1+2*n_B)n_L$ parameters.

Solving the Steady State Equations

In order to find the total signal, S, we first need to solve the system of equations to find $T_{ijk}$. Plugging (18) into (16) we find $$A_i \left(1 + \sum_{j'=1}^{n_L} K_{ij'}^D L_{j'}\right) = A_i^0 - \sum_{j'=1}^{n_L} \sum_{k'=1}^{n_B} T_{ij'k'} \quad (21)$$

$$A_i = \frac{A_i^0 - \sum_{j'=1}^{n_L} \sum_{k'=1}^{n_B} T_{ij'k'}}{1 + \sum_{j'=1}^{n_L} K_{ij'}^D L_{j'}}.$$

This can be used to solve for $D_{ij}$ $$D_{ij} = K_{ij}^D \frac{A_i^0 - \sum_{j'=1}^{n_L} \sum_{k'=1}^{n_B} T_{ij'k'}}{1 + \sum_{j'=1}^{n_L} K_{ij'}^D L_{j'}} L_j \quad (22)$$

which we can plug into (19) to get a coupled set of $N = n_A \cdot n_L \cdot n_B$ quadratic equations for $T_{ijk}$ $$T_{ijk} = K_{ijk}^T K_{ij}^D \left(\frac{A_i^0 - \sum_{j'=1}^{n_L} \sum_{k'=1}^{n_B} T_{ij'k'}}{1 + \sum_{j'=1}^{n_L} K_{ij'}^D L_{j'}}\right) L_j \left(B_k^0 - \sum_{i'=1}^{n_A} \sum_{j'=1}^{n_L} T_{i'j'k}\right). \quad (23)$$

From (23) we can obtain the signal S, using equation (20).

The error function and least square minimization.

In order to solve Eq. 23, we minimize an error function, defined as follows:

$$E(T_{ijk}) \equiv \sum_{i=1}^{n_A} \sum_{j=1}^{n_L} \sum_{k=1}^{n_B} \quad (24)$$

$$\left[K_{ijk}^T K_{ij}^D \left(\frac{A_i^0 - \sum_{j'=1}^{n_L} \sum_{k'=1}^{n_B} T_{ij'k'}}{1 - \sum_{j'=1}^{n_L} K_{ij'}^D L_{j'}}\right) L_j \left(B_k^0 - \sum_{i'=1}^{n_A} \sum_{j'=1}^{n_L} T_{i'j'k}\right) - T_{ijk}\right]^2.$$

Here, E is a function of the complete set of $T_{ijk}$'s. It is always positive, being a sum of squares, and vanishes if and only if $T_{ijk}$ is a solution to equation (23), which can now be written as $$E(T_{ijk}) = 0.$$

(25)

This equation is now in a form that can be solved numerically for any given set of parameters via standard optimization methods such as MATLAB's fmincon and lsqnonlin functions.

Dimensional Reduction

The system of equations describing our model can be simplified by dimensional reduction, in which we redefine the variables to reduce the number of parameters and make the remaining parameters dimensionless.

First, we change the units of signal strength using a scaling factor, $\alpha$.

$$S \to \alpha \cdot S$$

$$\varepsilon_{ijk} \to \alpha \cdot \varepsilon_{ijk}. \quad (26)$$

By choosing a value of $\alpha = (\Sigma_{i,j,k} \varepsilon_{ijk})^{-1}$, we can obtain units such that the phosphorylation rate constants for all complexes sum to 1:

$$\sum_{i,j,k} \varepsilon_{ijk} = 1. \quad (27)$$

Similarly, changing the receptor units by rescaling with a factor $\beta$ gives rise to the following transformation:

$$A_i \to \beta \cdot A_i$$

$$BB_k \to \beta \cdot B_k$$

$$D_{ij} \to \beta \cdot D_{ij}$$

$$T_{ijk} \to \beta \cdot T_{ijk}$$

$$S \to \beta \cdot S$$

$$K_{ijk}^T \to \beta^{-1} \cdot K_{ijk}^T \cdot D \quad (28)$$

By choosing $\beta = \Sigma_{i,j,k} K_{ijk}^T$ we effectively obtain units for the receptors and receptor complexes in which the $K_{ijk}^T$ sum to 1:

$$\sum_{i,j,k} K_{ijk}^T = 1. \quad (29)$$

Finally, we can also independently choose new units for each individual ligand species:

$$L_j \to \gamma_j \cdot L_j$$

$$K_{ij}^D \to \gamma_j^{-1} K_{ij}^D \quad (30)$$

We can make these dimensionless by choosing $\gamma_j = \Sigma_i K_{ij}^D$, such that for every j, $$\sum_i K_{ij}^D = 1. \quad (31)$$

Using these re-scaled variables and parameters, we can explore the complete parameter space by examining only parameter values satisfying equations (27), (29), and (31). These constraints reduce the number of independent parameters, $N_p$, by $3+n_L$.

The (2,2,2) Model and Parameter Selection

In order to see what behaviors arise from the model of promiscuous interactions, we focused on a specific instantiation of the model with $N_L=2$ ligands, $N_A=2$ A-type receptors and $N_B=2$ B-type receptors, which we describe as the (2,2,2) model. In this case there are 20 independent biochemical parameters, $K_{ij}^P K_{ijk}^T$ and $\varepsilon_{ijk}$, restricted by equations (27, 29, 31), and 4 receptor expression level parameters $A_i^o$ and $B_k^o$. In order to study all possible behaviors, random sets of parameters were chosen. We chose random biochemical parameters distributed uniformly over the bounded domains defined by equations (27, 29, 31), while the receptor parameters were chosen from a log-uniform distribution in the range $[10^{-3}, 10^3]$. Simulations were performed for 100,000 random parameter sets, and an entire 2D input-output function, across 15×15 log-uniform ligand concentrations, was numerically computed for each set. Results are plotted in FIGS. 9A-9E.

While the present invention has been illustrated and described with reference to certain exemplary embodiments, those of ordinary skill in the art will understand that various modifications and changes may be made to the described embodiments without departing from the spirit and scope of the present invention, as defined in the following claims.

What is claimed is:

1. A method of inducing a bone morphogenetic protein (BMP)-dependent response in a cell comprising an overexpressed BMPR1B NMuMG-like BMP receptor profile, or an overexpressed ALK1 NMuMG-like BMP receptor profile, the method comprising:
   exposing the cell comprising the overexpressed BMPR1B NMuMG-like BMP receptor profile to one or more heterologous BMPs selected from the group consisting of BMP4, BMP9, BMP10, GDF5, a mixture of BMP4 and BMP9, and a mixture of BMP4 and GDF5; or
   exposing the cell comprising the overexpressed ALK1 NMuMG-like BMP receptor profile to one or more heterologous BMPs selected from the group consisting of BMP4, BMP9, BMP10, a mixture of BMP4 and BMP9, and a mixture of BMP4 and BMP10.

2. The method of claim 1, wherein exposing the cells comprising the NMuMG-like BMP receptor profile to heterologous BMPs comprises a mixture of BMP4 and BMP9;
   wherein exposing the cell comprising the overexpressed BMPR1B NMuMG-like BMP receptor profile to heterologous BMPs comprises exposing the cell to a mixture of BMP4 and BMP9, or a mixture of BMP4 and GDF5; and
   wherein exposing the cell comprising the overexpressed ALK1 NMuMG-like BMP receptor profile to heterologous BMPs comprises exposing the cell to a mixture of BMP4 and BMP9, or a mixture of BMP4 and BMP10.

3. The method of claim 1, wherein exposing the cell comprising the overexpressed ALK1 NMuMG-like BMP receptor profile to the one or more heterologous BMPs comprises exposing the cell to a mixture of BMP4 and BMP10.

4. The method of claim 1, wherein exposing the cell comprising the overexpressed BMPR1B NMuMG-like BMP receptor profile to the one or more heterologous BMPs comprises exposing the cell to a mixture of BMP4 and GDF5.

5. The method of claim 1, comprising exposing the cell comprising the overexpressed BMPR1B NMuMG-like BMP receptor profile, and/or the overexpressed ALK1 NMuMG-like BMP receptor profile to heterologous BMP4 or BMP9.

6. A method of inducing a bone morphogenetic protein (BMP)-dependent response in a cell comprising a mouse mammary gland (NMuMG-like) BMP receptor profile, the method comprising exposing the cell to heterologous homodimers of BMP4, BMP9, or BMP10 at about 10 to about 1,000 ng/ml, or a mixture of BMP4 and BMP9 comprising homodimers of BMP4 at about 10 to about 1000 ng/ml and homodimers of BMP9 at about 10 to about 1,000 ng/ml.

7. A method of inducing a bone morphogenetic protein (BMP)-dependent response in a cell comprising an embryonic stem cell (ESC)-like BMP receptor profile, the method comprising exposing the cell to a mixture of BMP4 and BMP9 that comprises homodimers of BMP4 at about 10 to about 1000 ng/ml and homodimers of BMP9 at about 10 to about 1,000 ng/ml with a ratio of BMP4:BMP9 of about 1.0:0.4 to about 1.0:100.

8. The method of claim 1, wherein exposing the cell comprising the overexpressed BMPR1B-like BMP receptor profile to the one or more heterologous BMPs comprises exposing the cell to
   homodimers of BMP4, BMP9, BMP10, or GDF5 at about 10 to about 1,000 ng/ml, or
   the mixture of BMP4 and BMP9, wherein the mixture comprises homodimers of BMP4 at about 10 to about 1000 ng/ml and homodimers of BMP9 at about 10 to about 1,000 ng/ml, or
   the mixture of BMP4 and GDF5, wherein the mixture comprises homodimers of BMP4 at about 10 to 1,000 ng/ml and homodimers of GDF5 at about 10 to 1,000 ng/ml.

9. The method of claim 1, wherein exposing the cells comprising the overexpressed ALK1 NMuMG-like BMP receptor profile to heterologous BMPs comprises exposing the cells to
   homodimers of BMP4, BMP9, or BMP10 at about 10 to about 1,000 ng/ml, or
   the mixture of BMP4 and BMP9, wherein the mixture comprises homodimers of BMP4 at about 10 to about 1,000 ng/ml and homodimers of BMP9 at about 10 to about 1,000 ng/ml, or
   the mixture of BMP4 and BMP10, wherein the mixture comprises homodimers of BMP4 at about 10 to about 1,000 ng/ml and homodimers of BMP10 at about 10 to about 1,000 ng/ml.

* * * * *